(12) United States Patent
Thompson et al.

(10) Patent No.: US 8,545,996 B2
(45) Date of Patent: Oct. 1, 2013

(54) ION-PAIRING SOFT SALTS BASED ON ORGANOMETALLIC COMPLEXES AND THEIR APPLICATIONS IN ORGANIC LIGHT EMITTING DIODES

(75) Inventors: Mark E. Thompson, Anaheim, CA (US); Chao Wu, Nanjing (CN); Hsiao-Fan Chen, Taipei County (TW)

(73) Assignee: The University of Southern California, Los Angeles, CA (US)

( * ) Notice: Subject to any disclaimer, the term of this patent is extended or adjusted under 35 U.S.C. 154(b) by 333 days.

(21) Appl. No.: 12/916,913

(22) Filed: Nov. 1, 2010

(65) Prior Publication Data

US 2011/0101856 A1    May 5, 2011

Related U.S. Application Data

(60) Provisional application No. 61/280,338, filed on Nov. 2, 2009.

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/E51.044; 546/4; 546/10

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |

(Continued)

FOREIGN PATENT DOCUMENTS

| EP | 0650955 | 5/1995 |
|---|---|---|
| EP | 1725079 | 11/2006 |

(Continued)

OTHER PUBLICATIONS

Kuwabara, Yoshiyuki et al., Thermally Stable Multilayered Organic Electroluminescent Devices Using Novel Starburst Molecules, 4,4',4"-Tri(*N*-carbazolyl)triphenylamine (TCTA) and 4,4',4"-Tris(3-methylphenylphenyl-amino)triphenylamine (*m*-MTDATA), as Hole-.

(Continued)

*Primary Examiner* — Michael H Wilson

(74) *Attorney, Agent, or Firm* — Morgan, Lewis & Bockius, LLP

(57) ABSTRACT

Organometallic soft salt compounds are provided. In particular, the compounds comprise mononuclear Ir-based soft salts. The compounds may be used in organic light emitting diodes (OLED) and light emitting cells (LEC).

9 Claims, 7 Drawing Sheets

C1A1

C1A2

C2A3

(56) References Cited

U.S. PATENT DOCUMENTS

| | | | |
|---|---|---|---|
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 2034538 | 3/2009 |
| EP | 2223986 | 9/2010 |
| JP | 200511610 | 1/2005 |
| JP | 2007123392 | 5/2007 |
| JP | 2007254297 | 10/2007 |
| JP | 2008074939 | 10/2009 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009050290 | 4/2009 |
| WO | WO 2009021126 | 5/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |
| WO | WO 2010/037667 | 4/2010 |
| WO | WO 2010/089393 | 8/2010 |

OTHER PUBLICATIONS

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral Ru$^{II}$ PHosphorescent Emitters," *Adv. Mater.*, 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(/) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865- 867 (1999).

Baldo, M.A. et al., "Very High-Efficiency Green Organic Light-Emitting Devices Based on Electrophosphorescence," *Appl. Phys. Lett.*, 75(1):4-6 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing NΛCΛN-Co-ordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Iridium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on π-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Wu C et al: "Study of ion-paired iridium complexes (soft salts) and their application in organic light emitting diodes", Journal of the American Chemical Society, vol. 132, No. 9, Mar. 10, 2010, pp. 3133-3139.

Mauro et al: "Complex Iridium(III) Salts: Luminescent Porous Crystalline Materials", Angewandte Chemie, International Edition, vol. 49, No. 7, Feb. 8, 2010, pp. 1222-1226.

Chen F-F et al: "Synthesis, crystal structure and photoluminescence properties of an organometallic Ir complex containing 2,2'-bipyrimidine as ancillary ligand", Chinese Journal of Inorganic Chemistry, vol. 24, No. 8, 2008, pp. 1219-1223.

Oster S S et al: "Synthesis, structure and reactivity of [Ir(dippe)(mu-Cl)]2, [Ir(dippe)2][Ir(dippe)C12] and [Ir(dippe)2]Cl", Polyhedron, vol. 23, No. 17, Nov. 11, 2004, pp. 2959-2965.

Chiswell B et al: "Complexes of iridium(III) with 1:10-phenanthroline", Journal of Inorganic and Nuclear Chemistry, vol. 26, No. 1, Jan. 1, 1964, pp. 47-51.

Kwong, R. et al., Efficient saturated red organic light emitting devices based on phosphorescent platinum(II) porphyrins. Chemistry of Materials 1999, 11 (12),3709-3713.

Adachi, C. et al., High-Efficiency Organic Electrophosphorescent Devices with Tris(2-phenylpyridine)iridium Doped into Electron Transporting Materials. Appl. Phys. Lett. 2000, 77 (6), 904-906.

Markham, J. P. J. et al., High-efficiency green phosphorescence from spin-coated single-layer dendrimer light-emitting diodes. Applied Physics Letters 2002, 80 (15), 2645-2647.

Sajoto, T. et al., Temperature Dependence of Blue Phosphorescent Cyclometallated Ir(III) Complexes. Journal of the American Chemical Society 2009, 131 (28), 9813-9822.

Sajoto, T. et al., Blue and Near-UV Phosphorescence from Iridium Complexes with Cyclometallated Pyrazolyl or N-Heterocyclic Carbene Ligands. Inorg. Chem. 200S, 44 (22), 7992-8003.

Lamansky, S. et al., Highly Phosphorescent Bis-Cyclometallated Iridium Complexes: Synthesis, Photophysical Characterization, and Use in Organic Light Emitting Diodes. J. Am. Chem. Soc. 2001, 123 (18), 4304-4312.

Lowry, M. S. et al., Accelerated luminophore discovery through combinatorial synthesis. Journal of the American Chemical Society 2004, 126 (43), 14129-14135.

Lo, K. K. W. et al., Novel luminescent cyclometallated iridium(III) diimine complexes that contain a biotin moiety. Organometallics 2004, 23 (13), 3108-3116.

Tang, C. W. et al., Electroluminescence of doped organic thin films. J. Appl. Phys. 1989,65 (9), 3610-3616.

Slinker, J. D. et al.., Green electroluminescence from an ionic iridium complex. Applied Physics Letters 200S, 86 (17), 173506.

Tamayo, A. B. et al., Cationic Bis-cyclometallated Iridium(III) Diimine Complexes and Their Use in Efficient Blue, Green, and Red Electroluminescent Devices. Inorg. Chern. 200S, 44 (24),8723-8732.

Graber, S. et al., A Supramolecularly-Caged Ionic Iridium(III) Complex Yielding Bright and Very Stable Solid-State Light-Emitting Electrochemical Cells. Journal of the American Chemical Society 2008,130 (4S), 14944-14945.

Su, U. C. et al., Decreased Turn-On Times of Single Component Light-Emitting Electrochemical Cells by Tethering an Ionic Iridium Complex with Imidazolium Moieties. Chemistry-an Asian Journal 2008, 3 (11), 1922-1928.

Green, M. L. H.et al., New Organometallic solids—synthesis and solid-state properties of salts of redoxactive organometallic clusters, J. Chern. Soc. Chem. Commun. 1987, (24),1811-1814.

Basolo, F., Stabilization of metal complexes by large counter-ions, Coord. Chern. Rev. 1968,3 (2), 213-223.

Braga, D.; Grepioni, F., Crystal construction and molecular interplay in solid ferrocene, nickelocene, and ruthenocene. Organometallics 1992, 11 (2), 711-718.

Li, J. et al., Synthetic control of excited-state properties in cyclometallated Ir(III) complexes using ancillary ligands. Inorganic Chemistry 2005, 44 (6), 1713-1727.

Colombo, M.G. et al., Facial Tris Cyclometallated Rh3+ and Ir3+ Complexes—Their Synthesis, Structure, and Optical Spectroscopic Properties. Inorganic Chemistry 1994,33 (3), 545-550.

Colombo, M.G. et al., Competition Between Ligand Centered and Charge-Transfer Lowest Excited-States in Bis Cyclometallated Rh3+ and Ir3+ Complexes. Electronic and Vibronic Spectra of Transition Metal Complexes I, 1994; vol. 171, pp. 143-171.

Turro, N. J., Modern Molecular Photochemistry. Benjamin/Cummings: Menlo Park, CA, 1978.

Ma, B.; Djurovich, P. I.; Thompson, M. E., Excimer and electron transfer quenching studies of a cyclometallated platinum complex. Coord. Chern. Rev. 2005,249,1501-1510.

D'Andrade, B. W. et al., Relationship between the ionization and oxidation potentials of molecular organic semiconductors. Organic Electronics 2006, 6(1), 11-20.

Djurovich, P. I. et al., Measurement of the lowest unoccupied molecular orbital energies of molecular organic semiconductors. Organic Electronics, 2009,10 (3), 515-520.

Pei, Q. et al., Polymer Light-Emitting Electrochemical-Cells. Sciellce 1995, 269 (5227),1086-1088.

Pei, Q. B. et al., Polymer light-emitting electrochemical cells: In situ formation of a light-emitting p-n junction. Journal of the American Chemical Society 1996, 118 (16), 3922-3929.

Hung, L. S.; Chen, C. H., Recent progress of molecular organic electroluminescent materials and devices. Materials Science & Engineering R-Reports 2002, 39 (5-6), 143-222.

Sprouse, S.; King, K. A.; Spellane, P. .I.; Watts, R.I., Photophysical Effects of MetalCarbon Sigma-Bonds in Ortho-Metalated Complexes of Ir(III) and Rh(III). *Journal of the American Chemical Society 1984*,106 (22),6647-6653.

Nazeeruddin, M. K.; Humphry-Baker, R.; Berner, D.; Rivier, S.; Zuppiroli, L.; Graetzel, M., Highly phosphorescence iridium complexes and their application in organic light-emitting devices. *Journal of the American Chemical Society* 2003, 125 (29), 8790-8797.

Di Censo, D.; Fantacci, S.; De Angelis, F.; Klein, e.; Evans, N.; Kalyanasundaram, K.; Bolink, H. J .; Gratzel, M.; Nazeeruddin, M. K., Synthesis, characterization, and DFT-TD-DFT calculations of highly phosphorescent blue light-emitting anionic iridium complexes. *Inorganic Chemistry* 2008, 47 (3), 980-989.

Toan, T., Teo, B. K.; Ferguson, J. A.; Meyer, T. J.; Dahl, L. F., Electrochemical synthesis and structure of tetrameric cyclopentadienyliron sulfide dication, [FE4(ETA-5-C5H5)4(MU-3-S)4]2+—metal cluster bonding description of electrochemically reversible [FE4(ETA-5-C5H5)4(MU-3-S)4]N system (N =−1 to +3). *Journal o fthe American Chemical Society* 1977, 99 (2), 408-416.

Pasynskii, A. A.; Eremenko, I. L.; Rakitin, Y. V.; Novotortsev, V. M.; Ellert, O. G.; Kalinnikov, V. T.; Shklover, V. E.; Struchkov, Y. T.; Lindeman, S. V.; Kurbanov, T. K.; Gasanov, G. 26 S., Anti-ferromagnetic complexes with metal metal bonds .9. Synthesis and molecular-structures of methylcyclopentadienylchromium(jij) sulfide diamagnetic tetramer and the anti-ferromagnetic copper(IJ) bromide adduct of the tetranuclear cluster (MEC5H4)4CR4(MU3-0)(MU3S) 3TH. *J. Orgnomet. Chem.* 1983,248 (3), 309-320.

Bandy, J. A.; Davies, C. E.; Green, M. L. H.; Green, J. c.; Prout, K.; Rodgers, D. P. S., Synthesis, crystal-structures, and bonding of the molybdenum cubane compounds [MO(MU-C5H4PRI)(MU-3-S)]4N+, where N = 0,1, and 2. J. Chern. Soc.-Chern. Commun. 1983, (23),1395-1397.

McQueen, A. E. D.; Blake, A. J.; Stephenson, T. A.; Schroder, M.; Yellowlees, L. J., Intra-molecular and inter-molecular stacking in tetracyanoethylene (tcne) complexes of platinum metal dithio acids—the structures and electrochemistry of [OS(S2PME2)2(PPH3)(TCNE)] [OS(S2PPH2)2(PPH3)(TCNE)]. *J. Chem. Soc.-Chem. Commun.* 1988, (23),1533-1535.

International Search Report corresponding to the PCT/US2010/055040 application.

ION-PAIRING SOFT SALTS BASED ON ORGANOMETALLIC COMPLEXES AND THEIR APPLICATIONS IN ORGANIC LIGHT EMITTING DIODES

This application claims priority to U.S. Provisional Application Ser. No. 61/280,338, filed on Nov. 2, 2009, which is herein expressly incorporated by reference in its entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to a new class of materials which can be used in organic light emitting diodes (OLED) and light emitting cells (LEC). In particular, the invention related to mononuclear Ir-based soft salts and their use in OLEDs and LECs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the structure:

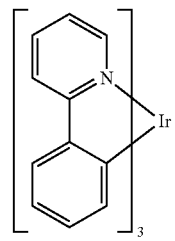

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

Organometallic soft salt compounds are provided, the compounds comprise the formula:

$$\sum_{i=1}^{m} C_i^{ai+} \sum_{j=1}^{n} C_j^{bj-}.$$

$C_i^{ai+}$ is an organometallic cation having formula $C_i$ with $a_i$ positive charge.

$C_j^{bj-}$ is an organometallic anion having formula $C_j$ with $b_j$ negative charge.

$C_i$ is $(L_i)_f M_i X_i$; formula $C_j$ is $(L_j)_g m_j X_j$. Each of $M_i$ and $M_j$ is independently a transition metal or a lanthanide. Each of $L_i$ and $L_j$ is independently a mono-, di-, tri- or polydentate ligand. Each of f and g may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

In one aspect, the compound has the formula $$\sum_{i=1}^{m} C_i^{ai+} \sum_{j=1}^{n} C_j^{bj-},$$

as described above.

In one aspect, each of $M_i$ and $M_j$ are Ir. In another aspect, each of $M_i$ and $M_j$ are Ir(III).

In one aspect, the organometallic cation has the formula:

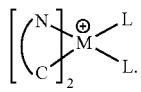

In another aspect, the organometallic anion has the formula:

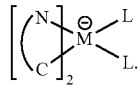

Each

independently represents a bonded pair of aromatic or heteroaromatic rings coordinated to the metal via a nitrogen atom and an $sp^2$ hybridized carbon atom.

In one aspect,

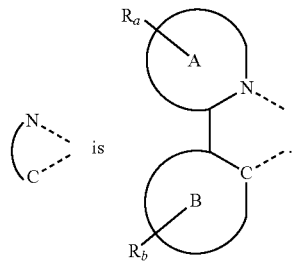

A and B are each independently a 5 or 6-membered aromatic or heteroaromatic ring. A-B represents a bonded pair of aromatic or heteroaromatic rings coordinated to the metal via a nitrogen atom on ring A and an $sp^2$ hybridized carbon atom on ring B. Each of $R_a$ and $R_b$ may represent mono, di, tri, or tetra substituents. Each of $R_a$ and $R_b$ substituent are independently selected from a group consisting of hydrogen, deuterium, alkyl, heteroalkyl, aryl, or heteroaryl. Two adjacent substituents may form into a ring.

Each

is independently selected from the group consisting of:

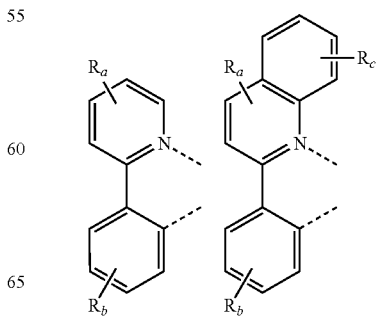

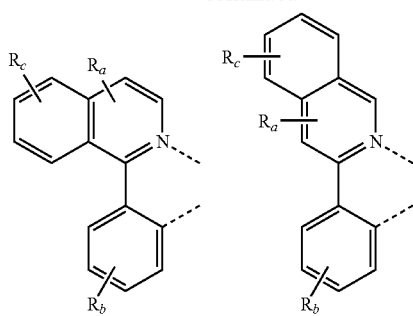
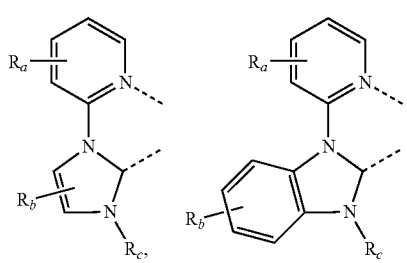
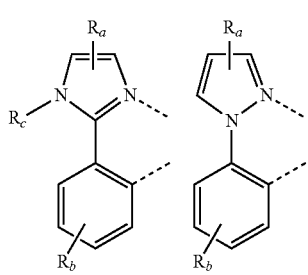
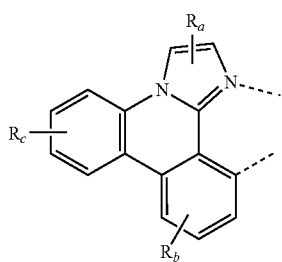
Each of $R_a$, $R_b$ and $R_c$ may represent mono, di, tri, or tetra substituents. Each of $R_a$, $R_b$ and $R_c$ substituent are independently selected from a group consisting of hydrogen, deuterium, alkyl, heteroalkyl, aryl, or heteroaryl. Two adjacent substituents may form into a ring.
Each of $L_i$ and $L_j$ are independently selected from the group consisting of:
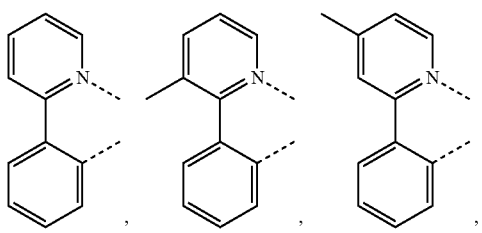
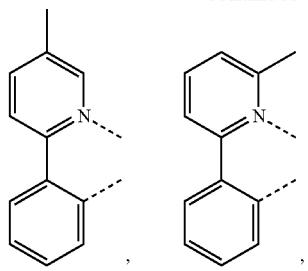
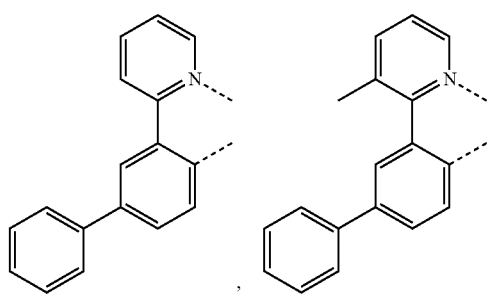
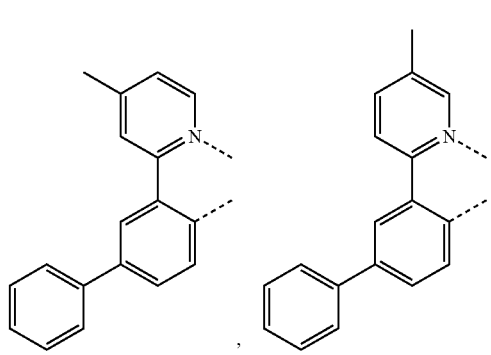
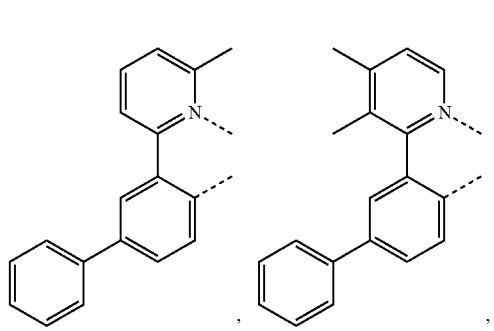
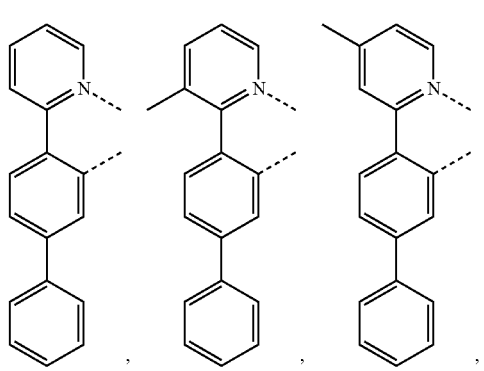

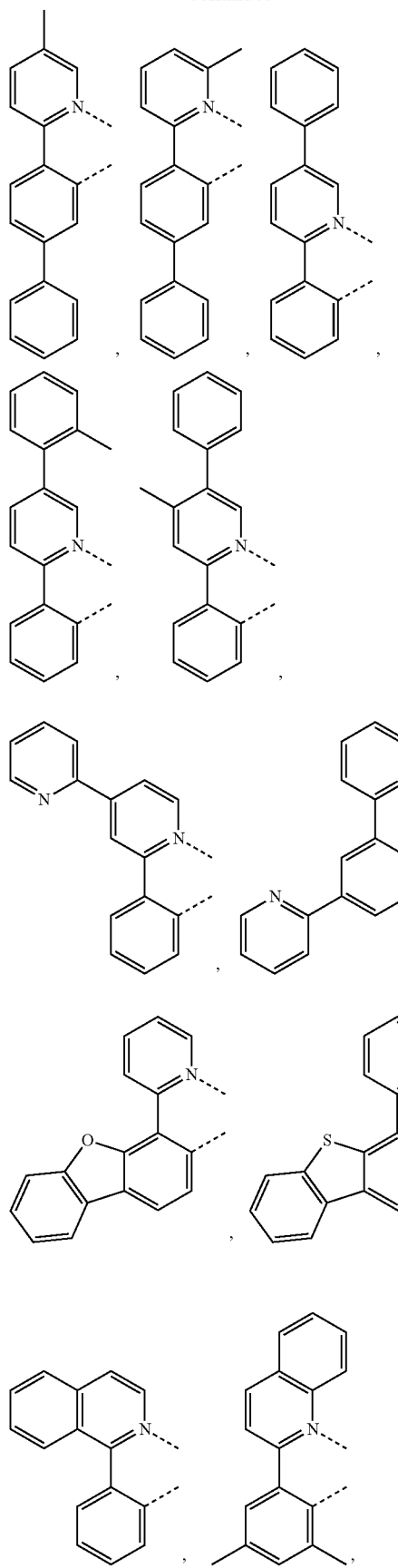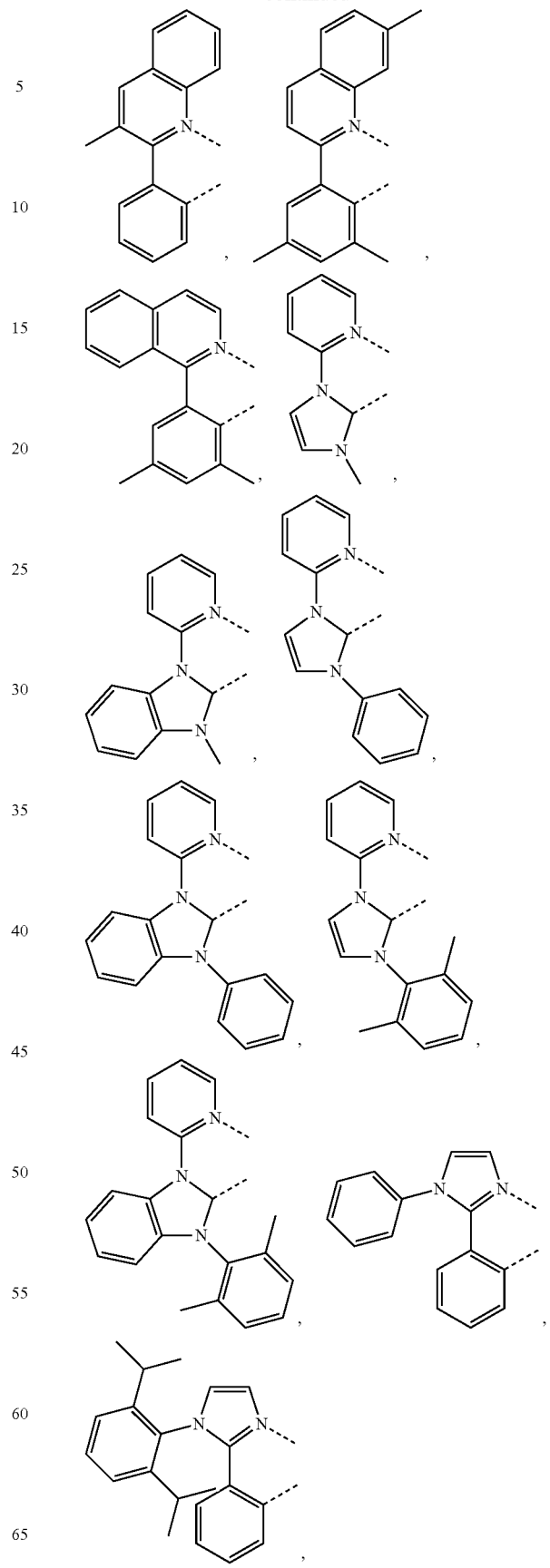

-continued
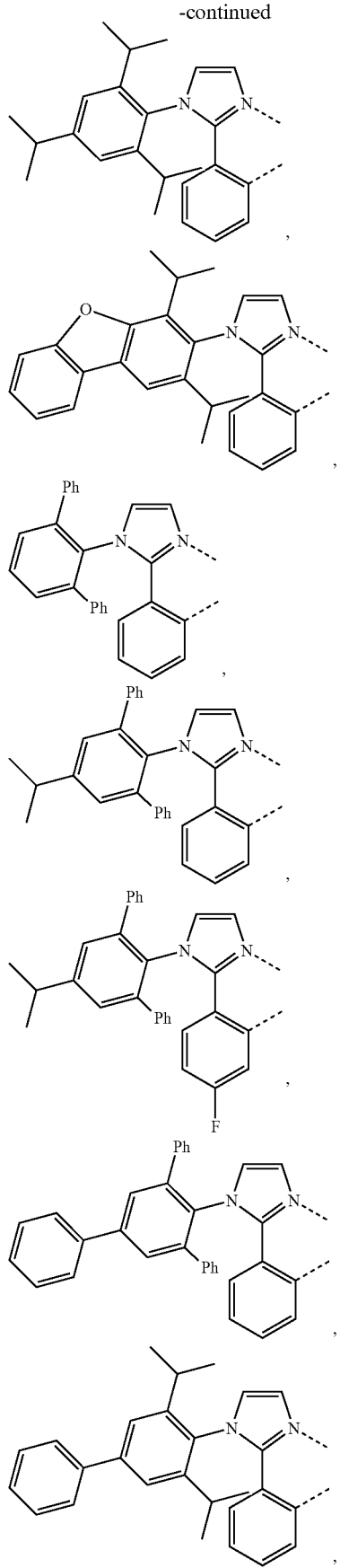
-continued
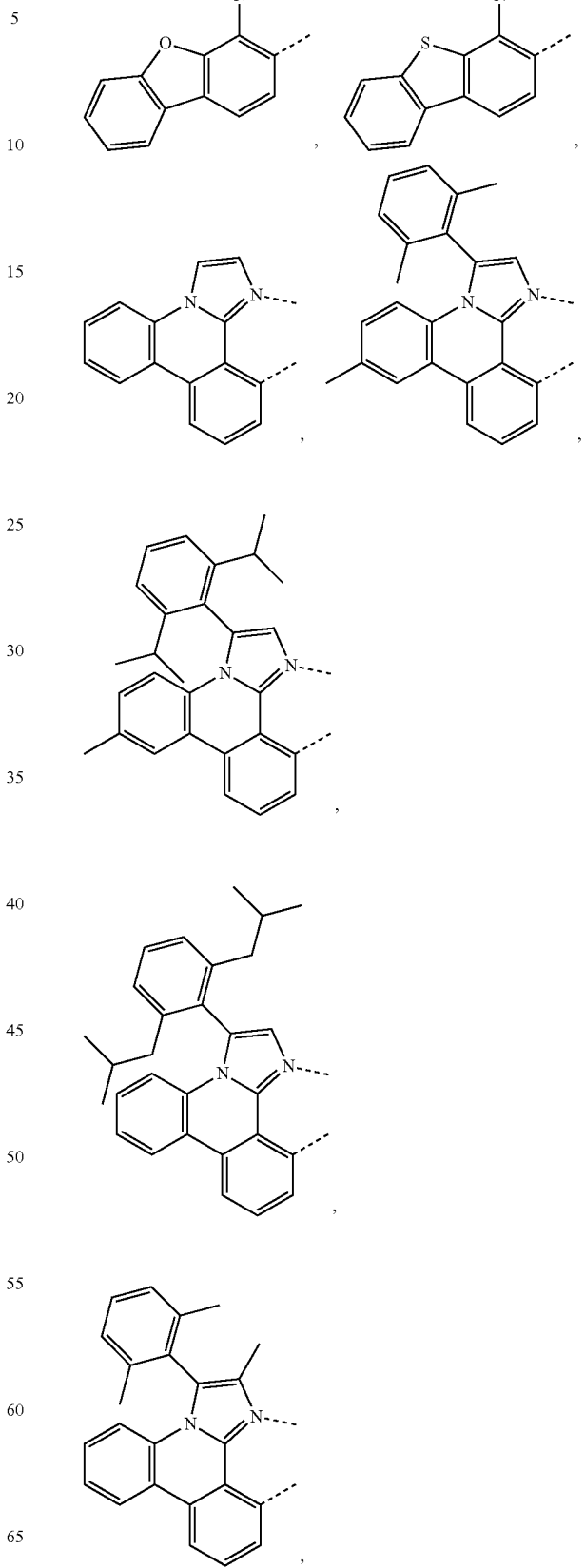

-continued

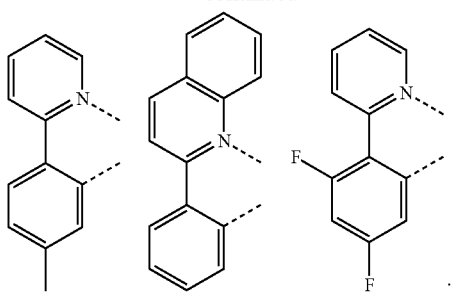

Preferably, each of $L_i$ and $L_j$ are independently selected from the group consisting of:

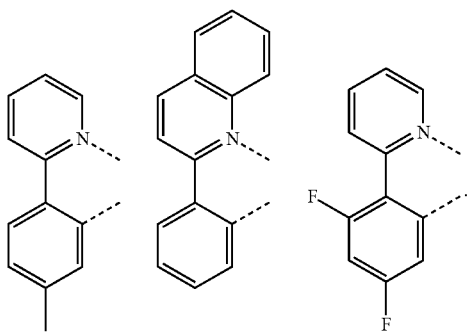

In one aspect, all of the organometallic cations and all of the organometallic anions in the complex are the same.

In yet another aspect, the organometallic anion is selected from the group consisting of:

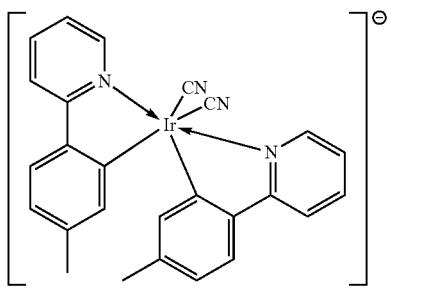

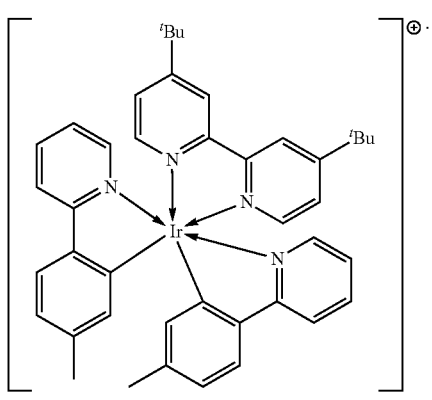

In a further aspect, organometallic cation is selected from the group consisting of:

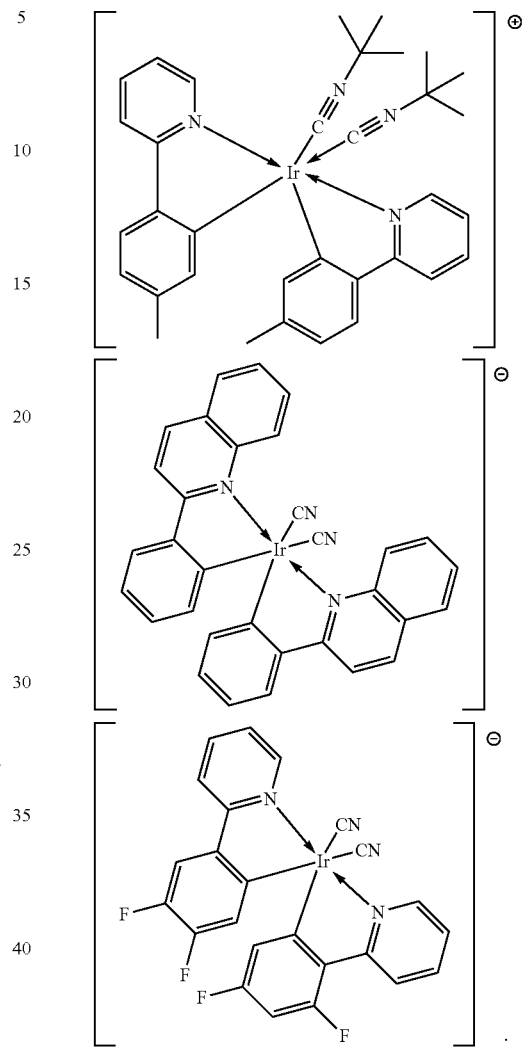

Specific examples of the compounds are provided. In one aspect, the compound is selected from the group consisting of:

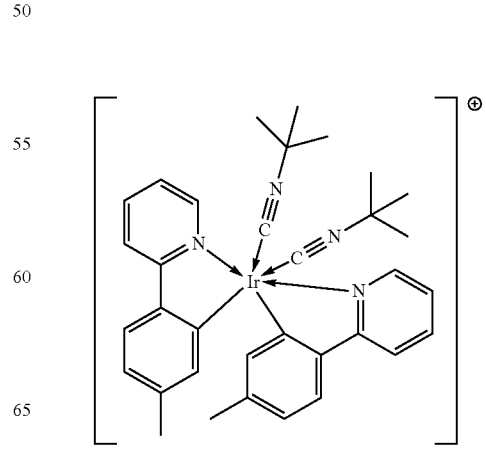

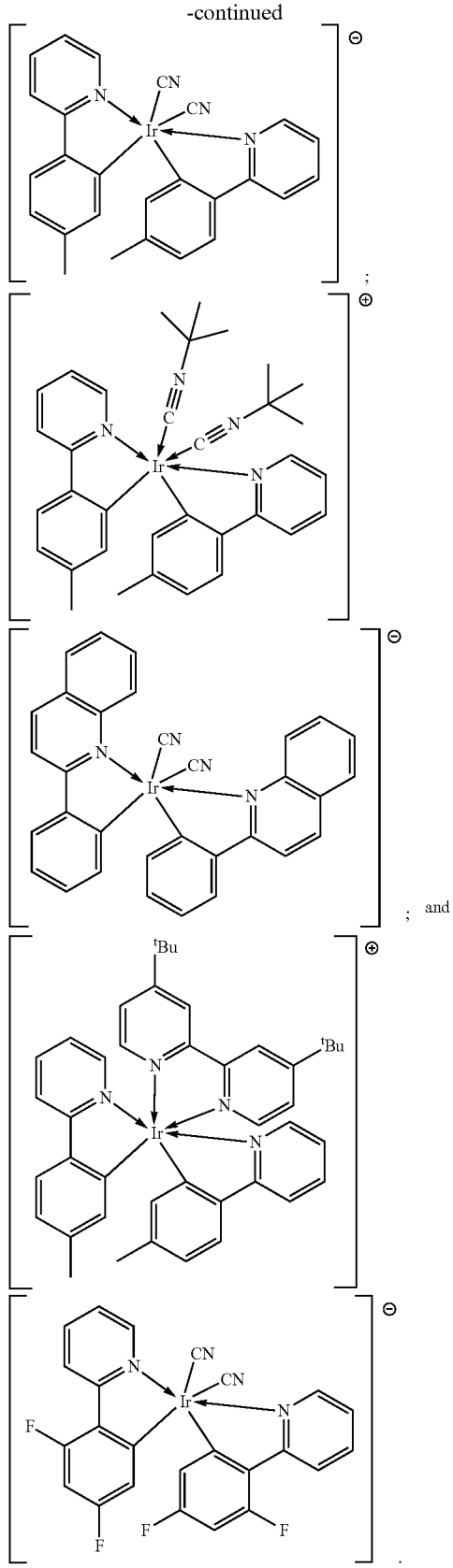

; and

.

Additionally, a first device comprising an organic light emitting device is provided. The organic light emitting device comprises an anode, a cathode, and an organic layer, disposed between the anode and the cathode. The organic layer further comprises a compound comprising the formula:

$$\sum_{i=1}^{m} C_i^{a_i+} \sum_{j=1}^{n} C_j^{b_j-}.$$

$C_i^{1i+}$ is an organometallic cation having formula $C_i$ with $a_i$ positive charge.

$C_j^{bj-}$ is an organometallic anion having formula $C_j$ with $b_j$ negative charge.

$C_i$ is $(L_i)_f M_i X_i$; formula $C_j$ is $(L_j)_g M_j X_j$. Each of $M_i$ and $M_j$ is independently a transition metal or a lanthanide. Each of $L_i$ and $L_j$ is independently a mono-, di-, tri- or polydentate ligand. Each of f and g may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

In one aspect, the compound has the formula $$\sum_{i=1}^{m} C_i^{a_i+} \sum_{j=1}^{n} C_j^{b_j-},$$

as described above.

In one aspect, each of $M_i$ and $M_j$; are Ir. In another aspect, each of $M_i$ and $M_j$ are Ir(III).

In one aspect, the organometallic cation has the formula:

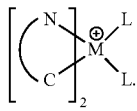

In another aspect, the organometallic anion has the formula:

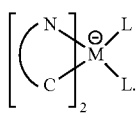

Each

independently represents a bonded pair of aromatic or heteroaromatic rings coordinated to the metal via a nitrogen atom and an $sp^2$ hybridized carbon atom.

In one aspect,

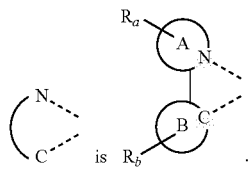

is $R_b$.

A and B are each independently a 5 or 6-membered aromatic or heteroaromatic ring. A-B represents a bonded pair of aromatic or heteroaromatic rings coordinated to the metal via a nitrogen atom on ring A and an sp² hybridized carbon atom on ring B. Each of $R_a$ and $R_b$ may represent mono, di, tri, or tetra substituents. Each of $R_a$ and $R_b$ substituent are independently selected from a group consisting of hydrogen, deuterium, alkyl, heteroalkyl, aryl, or heteroaryl. Two adjacent substituents may form into a ring.

Each

is independently selected from the group consisting of:

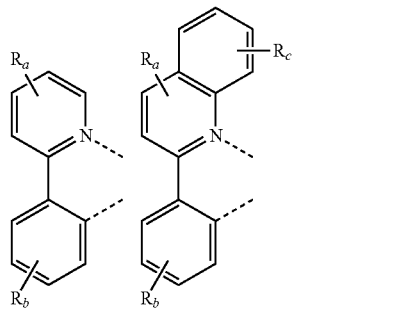

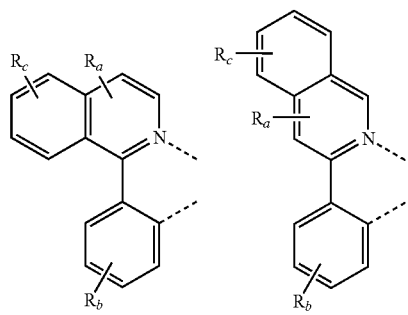

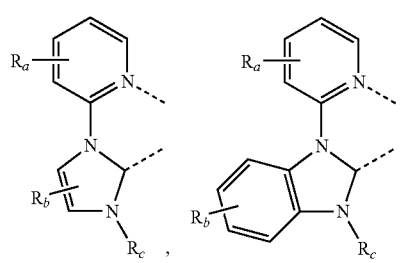

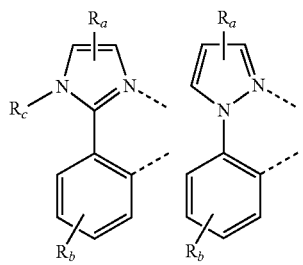

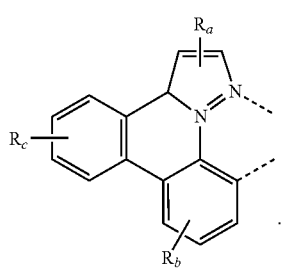

Each of $R_a$, $R_b$ and $R_c$ may represent mono, di, tri, or tetra substituents. Each of $R_a$, $R_b$ and $R_c$ substituent are independently selected from a group consisting of hydrogen, deuterium, alkyl, heteroalkyl, aryl, or heteroaryl. Two adjacent substituents may form into a ring.

Each of $L_i$ and $L_j$ are independently selected from the group consisting of:

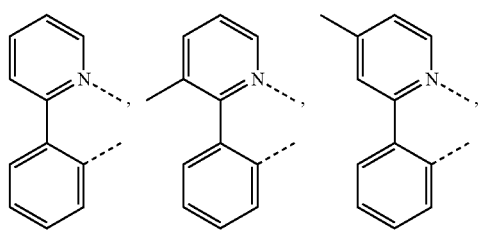

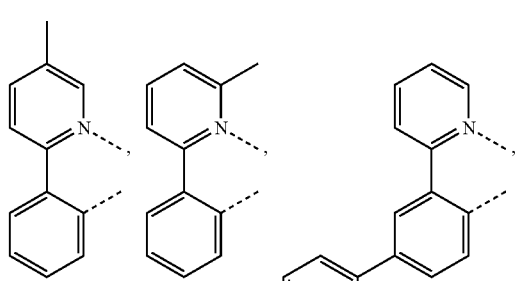

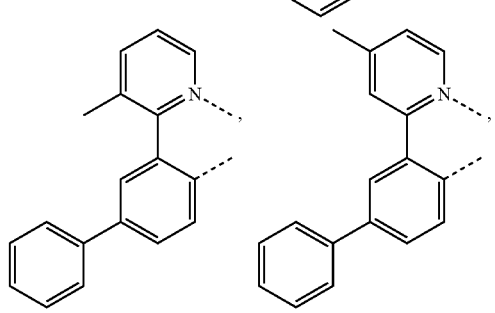

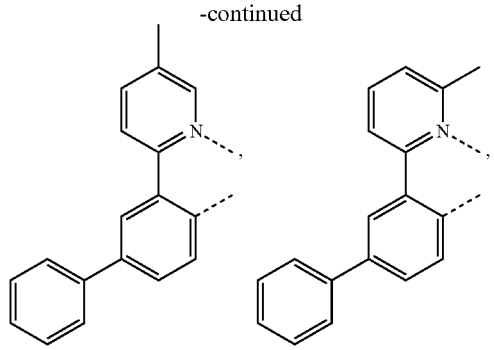
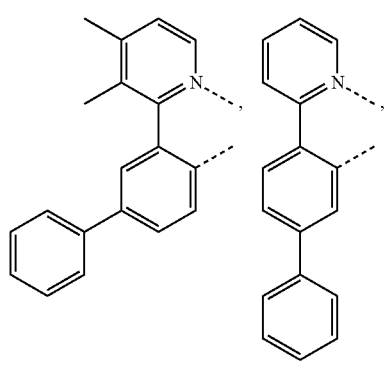
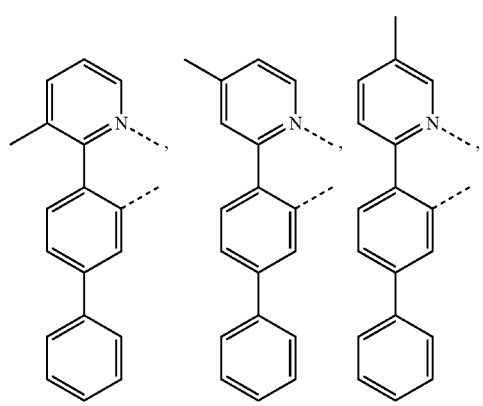
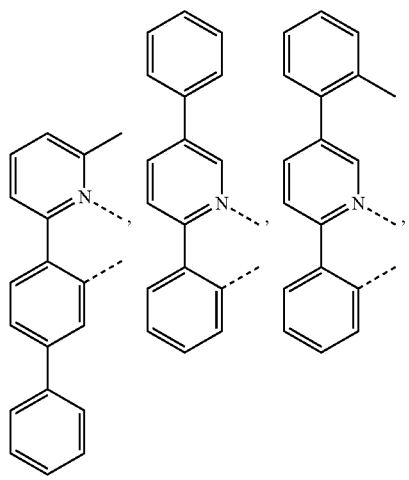
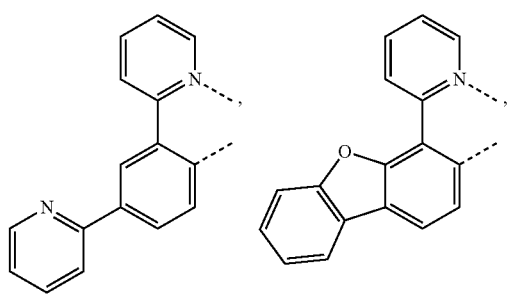
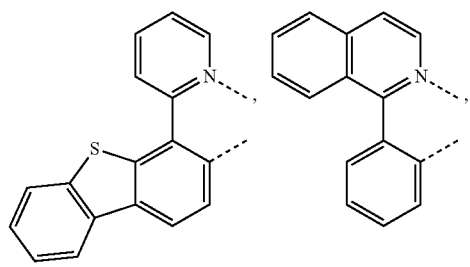
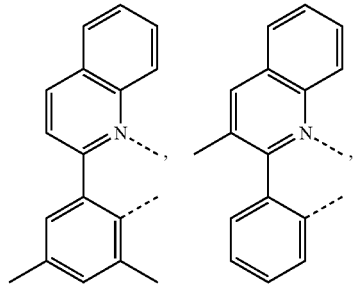
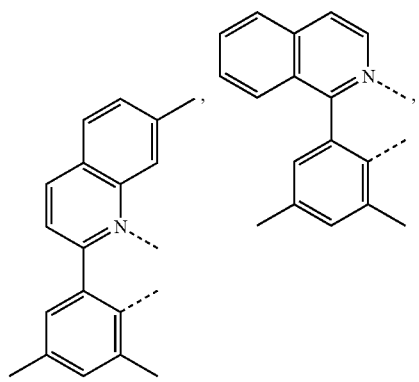

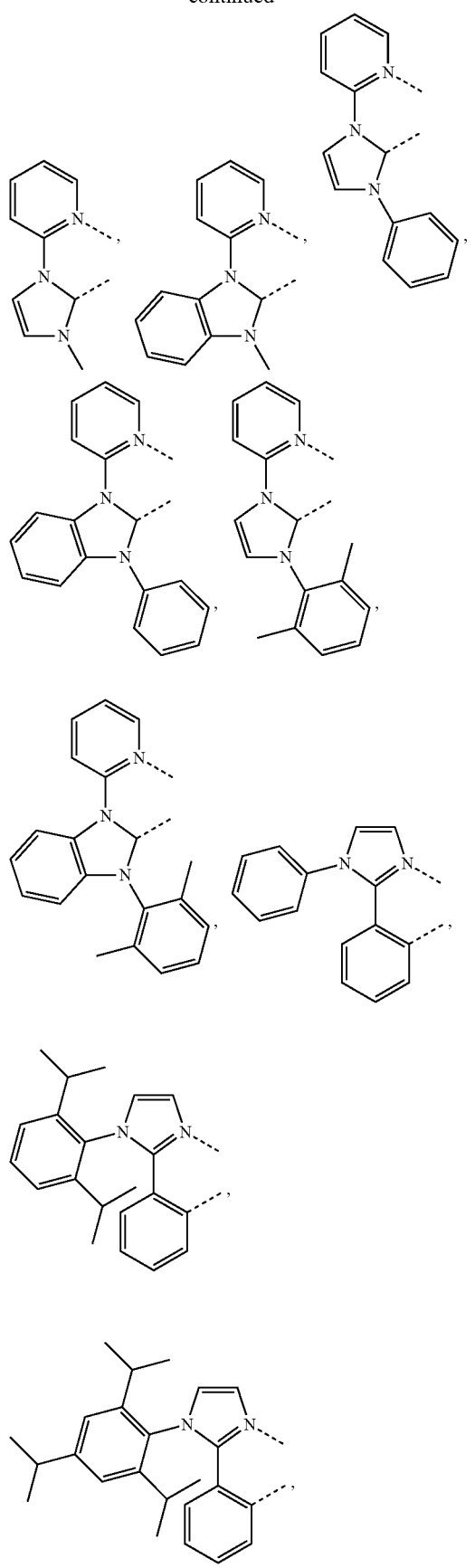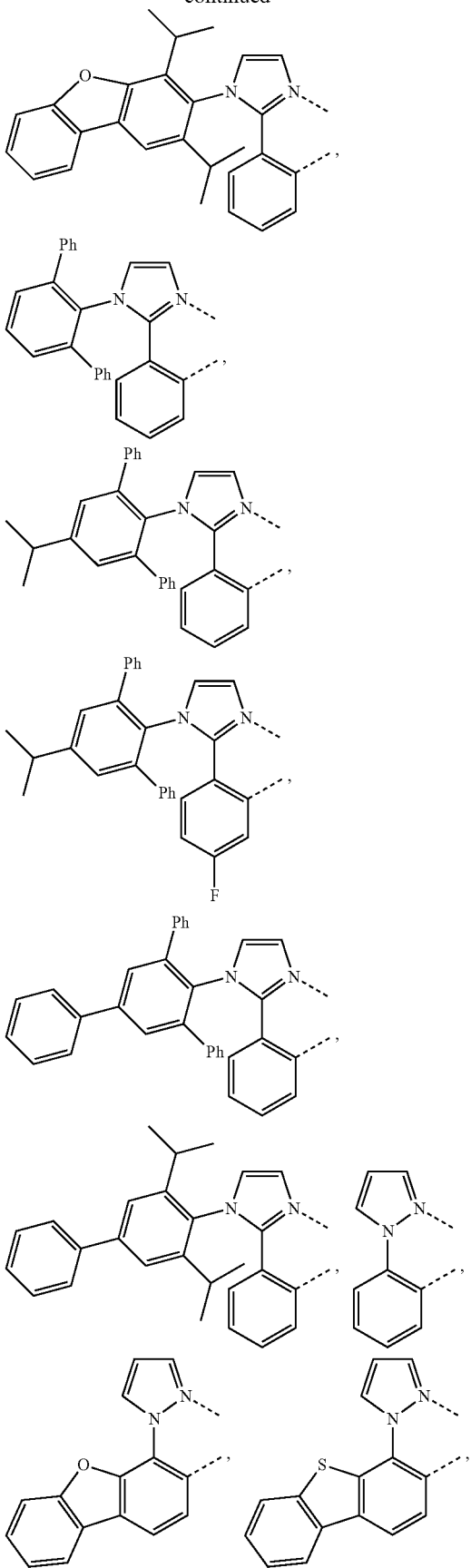

-continued
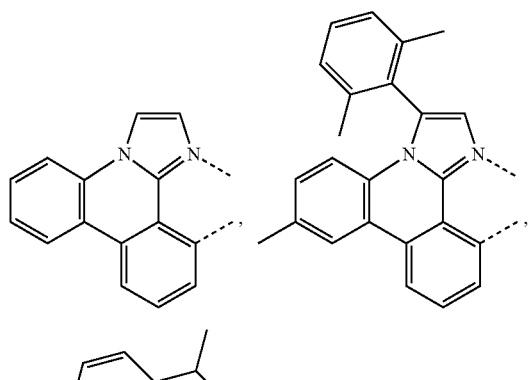
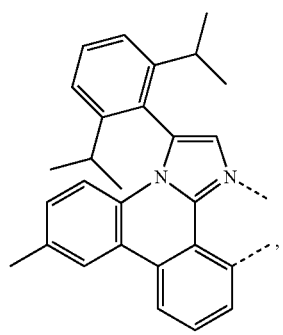
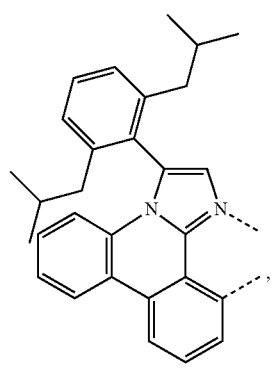
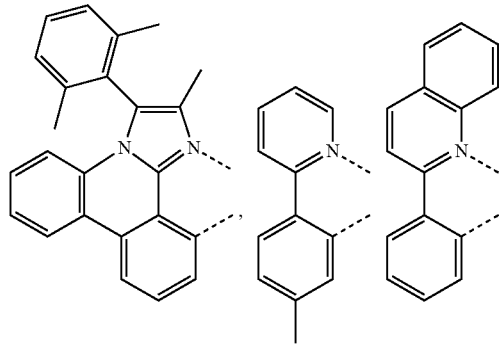
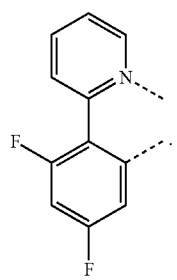
Preferably, each of $L_i$ and $L_j$ are independently selected from the group consisting of:
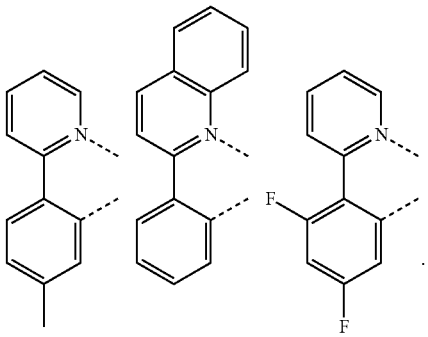
In one aspect, all of the organometallic cations and all of the organometallic anions in the complex are the same.
In yet another aspect, the organometallic anion is selected from the group consisting of:
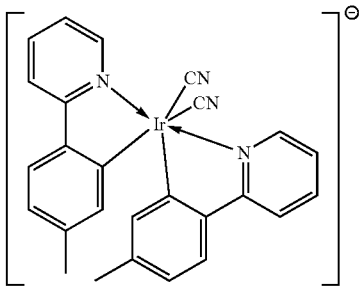
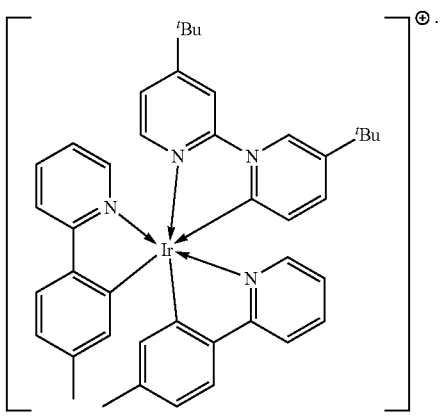

In a further aspect, organometallic cation is selected from the group consisting of:
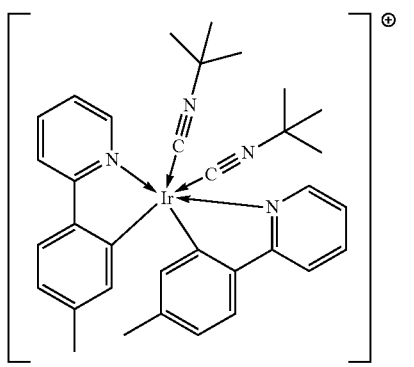
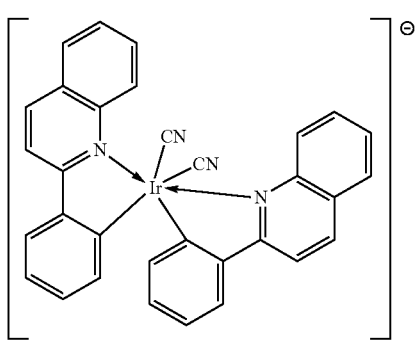
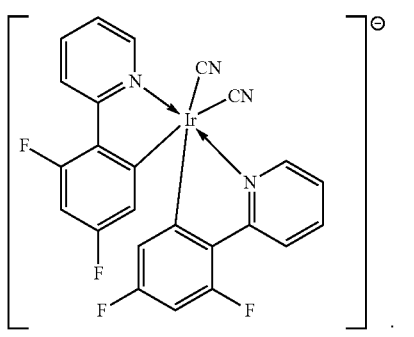
Specific examples of the devices are provided. In one aspect, the compound is selected from the group consisting of:
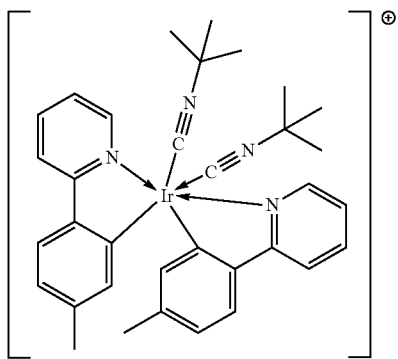
-continued
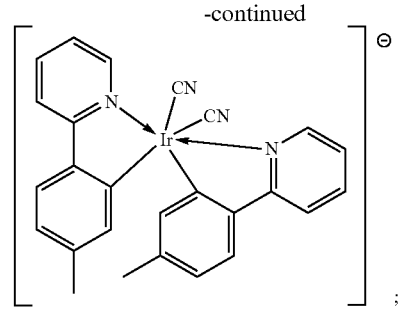
;
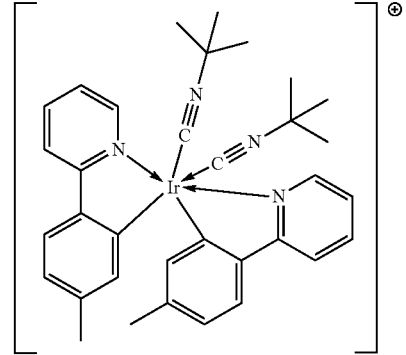
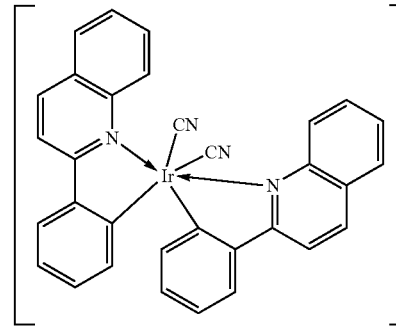
; and
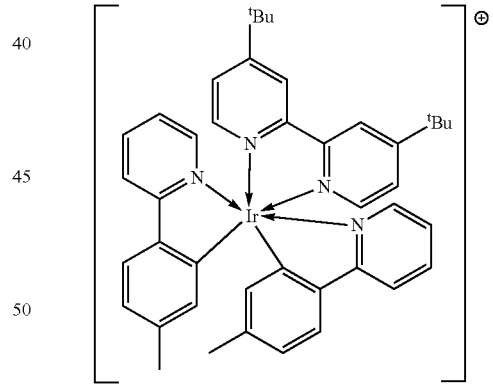
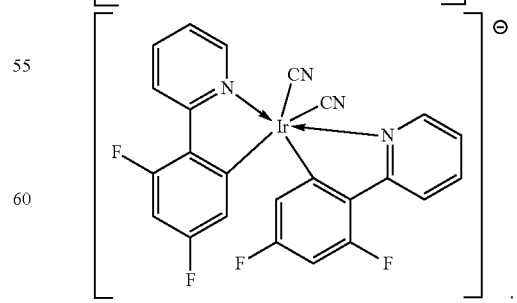
.
In one aspect, the organic layer is deposited using vapor disposition.

In another aspect, one of the organometallic anion and the organometallic cation has both a lower oxidation potential and a less negative reduction potential than the other. In other words, one of the ions of the soft salt, either the cation or anion, traps and carries both the hole and the electron.

In yet another aspect, PVK is mixed with dichlorobenzene and deposited prior to depositing the organic layer.

In a further aspect, a film comprising BCP is deposited over the organic layer.

In one aspect, the first device is an organic light emitting device. In another aspect, the first device is an organic light emitting cell.

A method of making the organometallic soft salt compounds is also provided. The method comprises obtaining an organometallic complex having the formula:

$$\sum_{i=1}^{m} C_i^{ai+} \sum_{j=1}^{n} C_j^{bj-},$$

by reacting an organometallic cation having the formula:
$C_i^{ai+}$ with $a_i$ positive charge, with an organometallic anion has the formula.
$C_j^{bj-}$ with $b_j$ negative charge.

$C_i$ is $(L_i)_f M_i X_i$ formula $C_j$ is $(L_j)_g M_j X_j$. Each of $M_i$ and $M_j$ is independently a transition metal or a lanthanide. Each of $L_i$ and $L_j$ is independently a mono-, di-, tri- or polydentate ligand. Each of $f$ and $g$ may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

In one aspect, the organometallic cation and the organometallic anion are obtained by: reacting

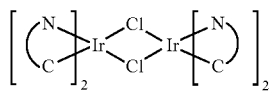

with a neutral ancillary ligand and an anionic ancillary ligand.

In another aspect, the organometallic cation and the organometallic anion are oxidized and reduced to form neutral metallated complexes before reaction to obtain the organometallic complex.

In yet another aspect, the neutral metallated complexes are thermally vacuum deposited in combination onto a substrate wherein the reaction is completed to obtain the organometallic complex.

In a further aspect, the method further comprises providing a first electrode, depositing the organometallic cation and the organometallic anion over the first electrode, and depositing a second electrode.

In one aspect, the first electrode is an anode and the second electrode is a cathode.

Another method of making the organometallic soft salt compounds is also provided. The method comprises reducing an organometallic cation having the formula:

$C_i^{ai+}$ to be neutral, oxidizing an organometallic anion having the formula:
$C_j^{bj-}$ to be neutral, and reacting the two neutral species to form an organometallic complex comprising the formula:

$$\sum_{i=1}^{m} C_i^{ai+} \sum_{j=1}^{n} C_j^{bj-}.$$

$C_i$ is $(L_i)_f M_i X_i$ and formula is $(L_j)_g M_j X_j$. Each of $M_i$ and $M_j$ is independently a transition metal or a lanthanide. Each of $L_i$ and $L_j$ is independently a mono-, di-, tri- or polydentate ligand. Each of $f$ and $g$ may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
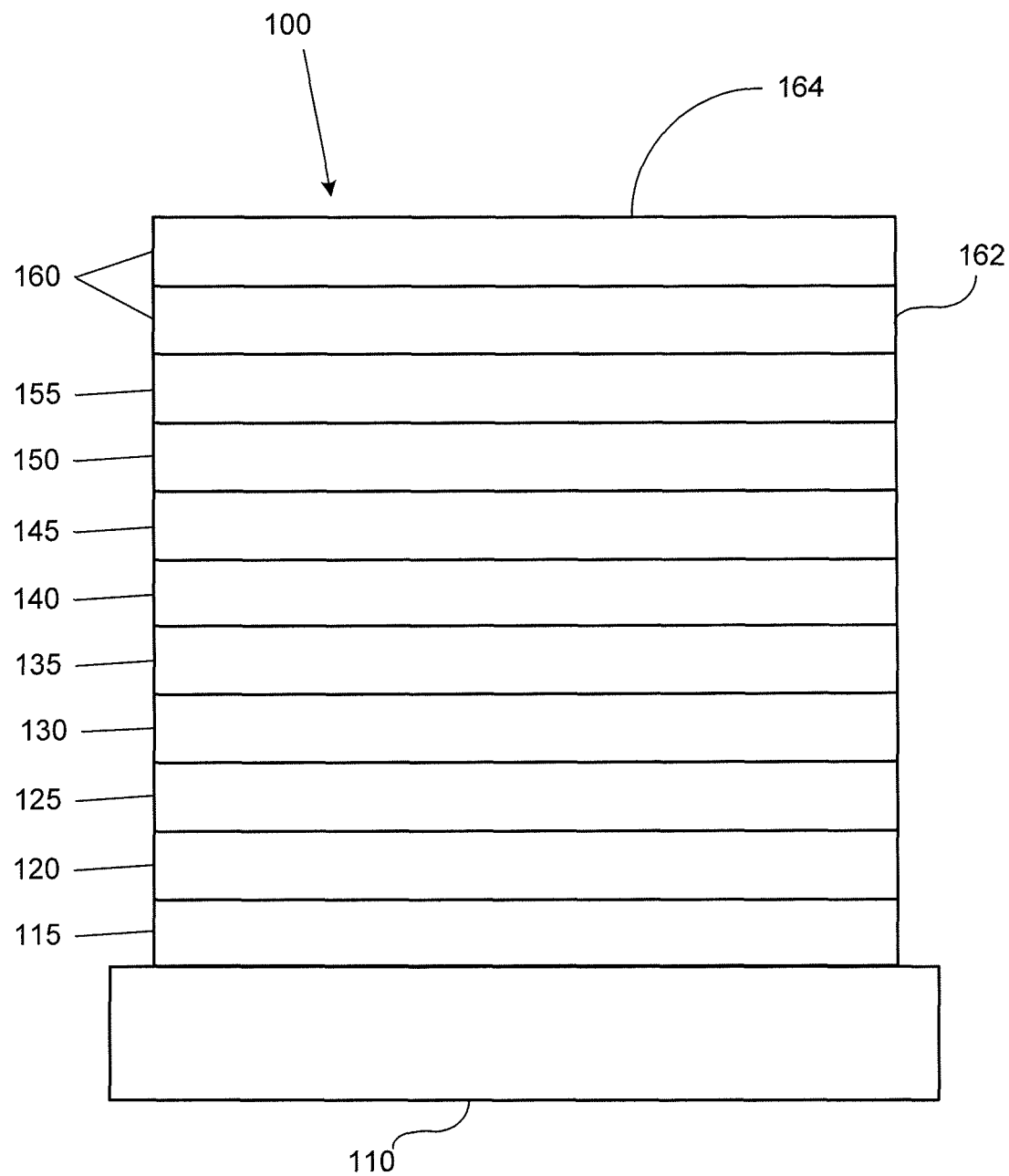
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F.sub.4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
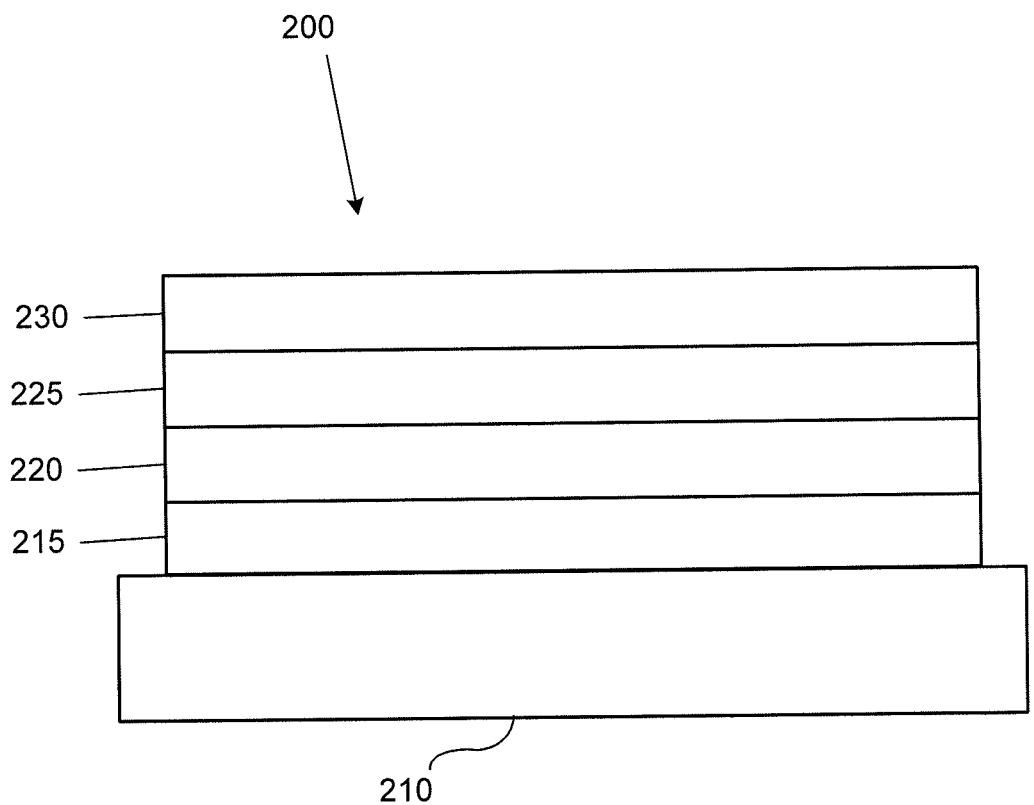
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Application of Soft Salts in Organic Electronic Devices

The complexes described herein are a new class of materials which can be used in organic light emitting diodes (OLED) and light emitting cells (LEC). The potential ways of applying them include neat layer as emissive layer, as dopant and host.

The basic structure of the metal-complex-based soft salts is:

Among the most successful phosphorescent emitters are cyclometallated Ir complexes, due to a number of useful features, including strong spin-orbit coupling, which leads to phosphorescent lifetimes in the 1-10 μsec range (Baldo, M. A. et al., Very High Efficiency Green Organic Light-Emitting Devices Based on Electrophosphorescence. Appl. Phys. Lett. 1999, 75 (1), 4-6), high phosphorescent efficiencies at room temperature (Sajoto, T. et al., Temperature Dependence of Blue Phosphorescent Cyclometallated Ir(III) Complexes. Journal of the American Chemical Society 2009, 131 (28), 9813-9822) and good color tunability of the emission energy, spanning the visible spectrum (Sajoto, T. et al., Blue and Near-UV Phosphorescence from Iridium Complexes with Cyclometallated Pyrazolyl or N-Heterocyclic Carbene Ligands. Inorg. Chem. 200S, 44 (22), 7992-8003; Lamansky, S. et al., Highly Phosphorescent Bis-Cyclometallated Iridium Complexes: Synthesis, Photophysical Characterization, and Use in Organic Light Emitting Diodes. J. Am. Chem. Soc. 2001, 123 (18), 4304-4312.) Both neutral and ionic Ir-based complexes have these photophysical properties. (Lowry, M. S. et al., Accelerated luminophore discovery through combinatorial synthesis. Journal Of The American Chemical Society 2004, 126 (43), 14129-14135; Lo, K. K. W. et al., Novel luminescent cyclometallated iridium(III)diimine complexes that contain a biotin moiety. Organometallics 2004, 23 (13), 3108-3116.) Neutral Ir-based complexes have been used in OLED structures, consisting of distinct carrier transporting/blocking and emitting layers. (Tang, C. W. et al., Electroluminescence of doped organic thin films. J. Appl. Phys.

Formula I

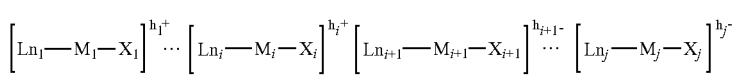

M can be either a transition metal or a lanthanide, L represents any number of mono-, di-, tri- or polydentate ligands and n represents bis or tris ligand coordination. X represents any number of chelated or auxiliary ligands. The sum of $h_1$ to $h_i$ is equal to the sum of $h_{i+1}$ to $h_j$.

Since the report of heterojunction organic light-emitting diodes (OLED), an extensive amount of research interest has been drawn to this field. (Tang, et al., Organic electroluminescent diodes. Appl. Phys. Lett. 1987, 51 (12), 913-915). A marked advance was made in OLED efficiencies when phosphorescent dopants were introduced. See, e.g., Kwong, R. et al., Efficient saturated red organic light emitting devices based on phosphorescent platinum(II) porphyrins. Chemistry Of Materials 1999, 11 (12), 3709-3713; Adachi, C. et al., High-Efficiency Organic Electrophosphorescent Devices with Tris(2-phenylpyridine)iridium Doped into Electron Transporting Materials. Appl. Phys. Lett. 2000, 77 (6), 904-906; Baldo, M. A. et al., Highly Efficient Phosphorescent Emission from Organic Electroluminescent Devices. Nature 1998, 395, 151-154; Baldo, M. A. et al., Very High Efficiency Green Organic Light-Emitting Devices Based on Electrophosphorescence. Appl. Phys. Lett. 1999, 75 (1), 4-6; Adachi, C. et al., Nearly 100% internal phosphorescence efficiency in an organic light emitting device. J. Appl. Phys. 2001, 90 (10), 5048-5051; Ikai, M. et al., Highly efficient phosphorescence from organic light-emitting devices with an exciton-block layer. Applied Physics Letters 2001, 79 (2), 156-158; Markham, J. P. J. et al., High-efficiency green phosphorescence from spin-coated single-layer dendrimer light-emitting diodes. Applied Physics Letters 2002, 80 (15), 2645-2647.

1989, 65 (9), 3610-3616.) Cationic Ir complexes have been used to light-emitting electrochemical cells (LEC), which typically consist of a single active layer, responsible for both carrier transport and light emission, while the studies of anionic Ir complexes have been mainly focused on their photophysics. (Slinker, J. D. et al., Green electroluminescence from an ionic iridium complex. Applied Physics Letters 200S, 86 (17), 173506; Tamayo, A. B. et al., Cationic Bis-cyclometallated Iridium(III) Diimine Complexes and Their Use in Efficient Blue, Green, and Red Electroluminescent Devices. Inorg. Chem. 200S, 44 (24), 8723-8732; Graber, S. et al., A Supramolecularly-Caged Ionic Iridium(III) Complex Yielding Bright and Very Stable Solid-State Light-Emitting Electrochemical Cells. Journal of the American Chemical Society 2008, 130 (4S), 14944-14945; Su, U. C. et al., Decreased Turn-On Times of Single Component Light-Emitting Electrochemical Cells by Tethering an Ionic Iridium Complex with Imidazolium Moieties. Chemistry-an Asian Journal 2008, 3 (11), 1922-1928).

"Soft salt" is a term introduced to describe ionic materials that are composed of only organometallic components, lacking halide, alkali metal or other ions commonly present as counterions for these materials. (Green, M. L. H. et al., New Organometallic solids—synthesis and solid-state properties of salts of redoxactive organometallic clusters, J. Chem. Soc. Chem. Commun. 1987, (24), 1811-1814.) These salts are considered "soft", because their component ions are of significantly larger radii than simple ions so that the lattice energies are expected to be lower and the ions are bonded mainly through van der Waals force. Soft salts can be readily obtained in crystalline form (Basolo, F., Stabilization of metal complexes by large counter-ions, Coord. Chern. Rev. 1968, 3 (2), 213-223; Braga, D.; Grepioni, F., Crystal construction and molecular interplay in solid ferrocene, nickelocene, and ruthenocene. Organometallics 1992, 11 (2), 711-718) and various cluster ions and soft salts with different metals, such as Fe26, Cr27, Mo28, Os29 and Ru29, have been studied. The crystal structure of an Ir-based soft salt, related to one of the compounds discussed herein, was also recently reported. (De Cola, L. et. al., private communication, manuscript submitted.)

It may also be desirable to use soft salts that have some smaller ions, e.g., $Na^+$ or $Cl^-$, or ions that are not organometallic, e.g., large organic molecules with a charge. This is concept is described herein by using the term "comprising" to describe the formula of the inventive compounds disclosed herein.

These compounds may also contain organometallic cations and sufficient anions to balance the charge. Similarly, these compounds may contain organometallic anions and sufficient cations to balance the charge.

Mononuclear Ir-based soft salts have not been examined and are interesting alternatives in OLEDs to the neutral materials that have been explored extensively in this application. These soft salts can be easily synthesized through metathesis reactions and show dual emission in solution, ambipolar charge conduction and good flexibility in setting the HOMO and LUMO energy levels, due to the two independent functional components in oppositely-charged ions. Herein, we present the synthesis, characterization and OLED studies for three soft salts. We show that the alignment of the energy levels within the soft salt can be adjusted by the ligand choice for each of the ions and this energy alignment is a useful parameter controlling the performance of the OLED.

Figure 3:
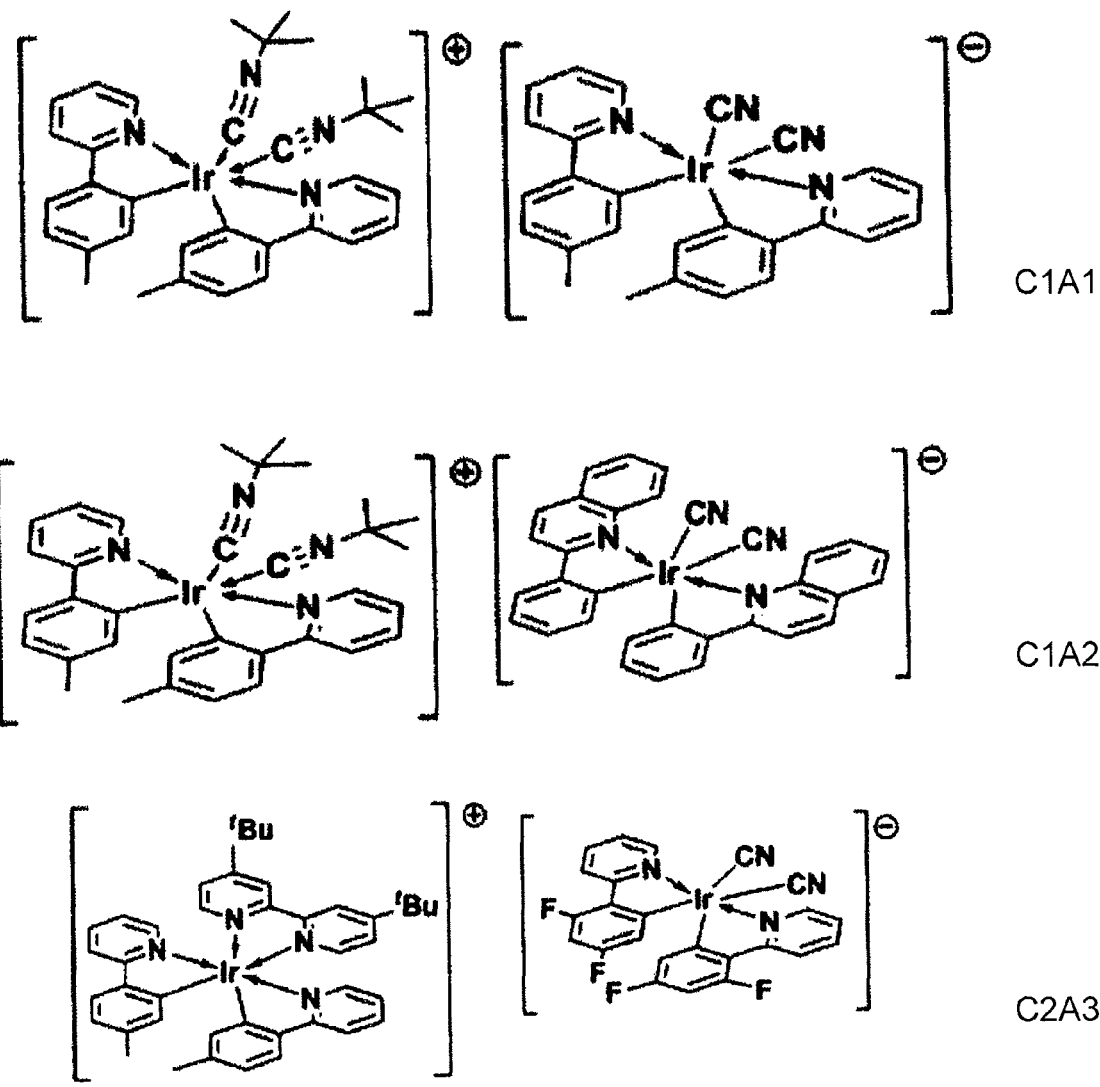
FIG. 3 shows structures of exemplary soft salts.

Ionic Ir complexes were synthesized from the dichloro-bridged Ir(III) dimer and excessive ligand in refluxing solvent. The net charge of the resulting Ir complex depends on the auxiliary ligand selected. For example, when cyanide ions are present, two anions coordinate with Ir to generate stable anionic Ir complexes. On the other hand, when neutral ligands, such as diimines and isocynides, are used, cationic complexes can be obtained. By mixing two oppositely charged Ir complexes in water, the soft salts were obtained through the metathesis reaction, in moderate yield. The three soft salts studied in this paper are composed of two different cations and three different anions. These five ions are abbreviated based on their charge, namely C for cations and A for anions, followed by a number to differentiate different ions. The structure of the ions and soft salts and their corresponding acronym are illustrated in FIG. 3.

Solvent-Free Deposition Technique for Soft Salts.

The component ions, namely cations and anions, of the soft salts can be oxidized and reduced before the metathesis reaction to form potentially stable and sublimable neutral metallated complexes. When these neutral complexes are thermally deposited under vacuum together, they will react on the substrate, returning to their original valence, thus forming the soft salts. This vapor deposition method is equivalent to vapor depositing the unsublimable soft salts. By controlling the amount of each component in the film, films can be obtained with different type of charges. A 1:1 ratio may give a pure soft salt film. It is also possible to use an excess of one compound or the other to make a film that is a combined soft salt and neutral dopant film. One advantage of this technique is the exclusion of the solvents during the whole process, which is useful to obtaining quality devices, because soft salts tend to create porous lattice where solvent molecules can be trapped and hard to remove. The deposition under vacuum forms pure soft salts in-situ also ensuring the quality of the film.

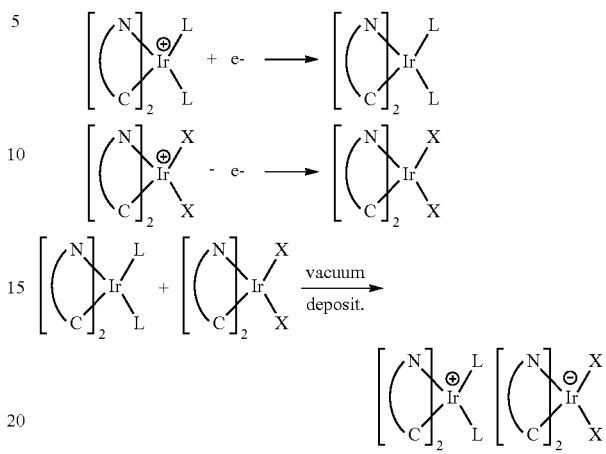

Several Ir-based materials were synthesized through metathesis reaction between halide and alkali metal salts of two cationic and three anionic Ir complexes, respectively. The resulting "soft salt" complexes are composed of an organometallic cation and an organometallic anion. The electrochemical and photophysical characterization of these compounds is also provided herein. The redox potentials of the soft salts may be determined by the lowest energy potentials of the two ions. Energy transfer between the ions in solution is observed, and found to take place at diffusion controlled rates. Additionally, organic LEDs were prepared with different soft salts, using the simple structure of anode/PVK/soft salt/BCP/cathode. The soft salts perform differently in devices, yielding from 0.2% to 4.7% in maximal external quantum efficiencies (EQE). The internal energy alignment between two ions in the soft salts may be responsible for the disparate EQE results. Sajoto, T. et al., Temperature Dependence of Blue Phosphorescent Cyclometallated Ir(III) Complexes. Journal of the American Chemical Society 2009, 131 (28), 9813-9822 Without being bound by theory, it is believed that the HOMO and LUMO values of one of the ions should fall between those of the other ion, i.e., one ion has both the lowest oxidation potential and the least negative reduction potential, in order to achieve a high EQE.

Photophysics and Quenching Study.

Figure 4:
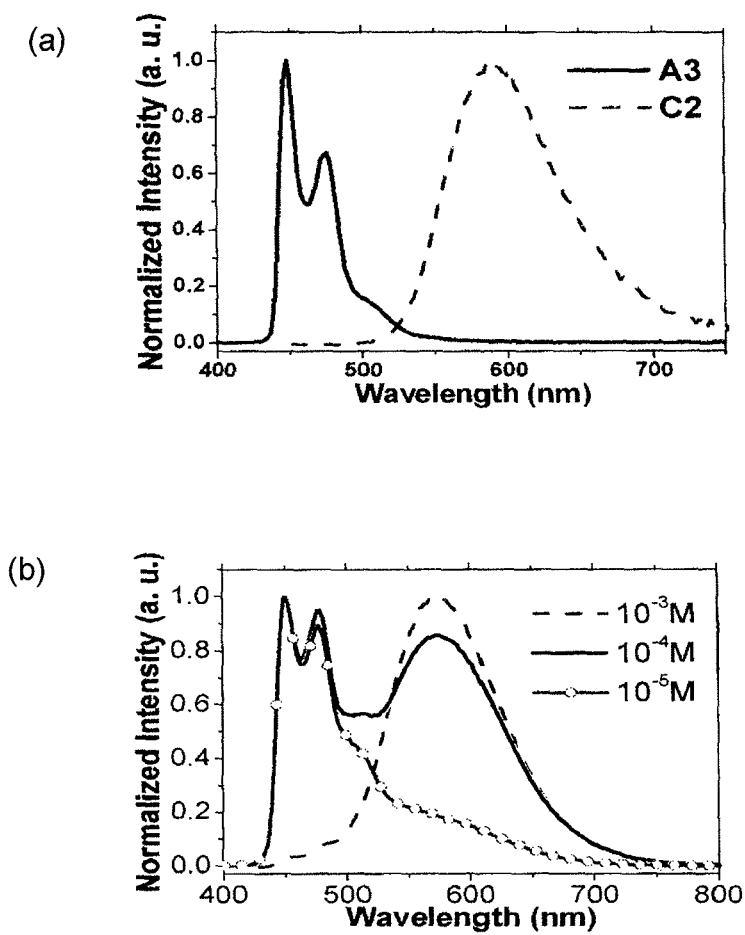
FIG. 4 shows photoluminescence spectrum of (a) C2C1 and A3Na; (b) C2A3 at different concentrations (all in degassed acetonitrile).

The emission data of the ions and soft salts is summarized in Table 1. The photoluminescent (PL) spectra of the ion C2 and A3 in degassed acetonitrile solution are presented in FIG. 4(a) as an example. The emission of A3, which peaks at around 450 nm, is blue-shifted by the electron-withdrawing fluorines in the chelating ligand with well-resolved vibronic structure. The structured emission is the result of a triplet ligand-centered CLC) transition on the cyclometallating ligands. (Li, J. et al., Synthetic control of excited-state properties in cyclometallated Ir(III) complexes using ancillary ligands. Inorganic Chemistry 2005, 44 (6), 1713-1727.) The rest of the ions exhibit a broad and featureless spectrum, exampled by C2. Single-ligand complexes C1, A1 and A2, are all expected to emit from metal-to-ligand charge-transfer (MLCT) states, while the difference in CAN ligand is responsible for the shift in peak position. (Colombo, M. G. et al., Facial Tris Cyclometallated Rh3+ And Ir3+ Complexes—Their Synthesis, Structure, And Optical Spectroscopic Properties. Inorganic Chemistry 1994, 33 (3), 545-550; Lamansky, S. et al., Synthesis and Characterization of Phosphorescent Cyclometallated Iridium Complexes. Inorg. Chem. 2001, 40 (7), 1704-1711). The mixed-ligand complex C2 showed a significantly red-shifted emission compared to C1 and At, because Ir→bipyridine CT transition, instead of Ir→tolylpyridine, becomes the lowest-energy one in this case. (Colombo, M. G. et al., Competition Between Ligand Centered And Charge-Transfer Lowest Excited-States In Bis Cyclometallated Rh3+ And Ir3+ Complexes. Electronic And Vibronic Spectra Of Transition Metal Complexes I, 1994; Vol. 171, pp 143-171).

The PL of the soft salts shows interesting concentration dependence, a result of the energy transfer between ions. C2A3 serves as a good example with the distinct spectrum from two ions, and three PL spectra measured at different concentrations are compared in FIG. 4(b). All three spectra were obtained with an excitation wavelength of 370 nm, which corresponds to the absorption of the A3. Based on the spectra, the ratio of two peaks varies greatly depending on the concentration, indicating that the degree of the energy transfer between the ions is different. At the relatively low concentration of $10^{-5}$M, the emission is mainly from the anion. This high-energy blue emission diminishes, when the solution gets more concentrated with cations serving as a quencher of A3 emission, giving exclusive C2 emission at concentrations of $10^{-3}$M and above.

TABLE 1

Energy levels and quantum yields of soft salts and their component ions.

| | Energy Levels (eV) | | | Quantum Yield (%) | | | $\lambda_{max}$ |
|---|---|---|---|---|---|---|---|
| | HOMO | LUMO | ΔE | In air[b] | Degassed[b] | Film[c] | (nm)[b] |
| C1[a] | −6.32 | −1.94 | 4.38 | 2.0 | 38 | 3.7 | 458 |
| C2[a] | −5.72 | −2.54 | 3.18 | 3.2 | 21 | 16 | 586 |
| A1[a] | −5.44 | −1.66 | 3.78 | 0.9 | 70 | 4.8[d] | 472 |
| A2[a] | −5.33 | −2.08 | 3.25 | 3.8 | 78 | 3.2[d] | 572 |
| A3[a] | −5.90 | −1.67 | 4.23 | 1.5 | 70 | 7.8[d] | 448 |
| C1A1 | −5.31 | −1.96 | 3.35 | 1.2 | 87 | 7.0 | 470 |
| C1A2 | −5.43 | −2.03 | 3.40 | 5.9 | 74 | 13 | 456[e], 572[f] |
| C2A3 | −5.73 | −2.57 | 3.16 | 3.2 | 24 | 18 | 448[e], 586[f] |

[a]The counterion for C1 is OTf, Cl⁻ for C2 and Na⁺ for all three anions.
[b]Measured in acetonitrile.
[c]Spin-coated from acetonitrile solution at 3000 rpm for 40 seconds followed by baking under vacuum at 90° C. for 2 h. Measured under nitrogen.
[d]The same as (c) except dissolved in acetonitrile/DMF mixture solution (20:1).
[e]At the concentration below $10^{-2}$M.
[f]At the concentration larger than 1M.

Figure 5:
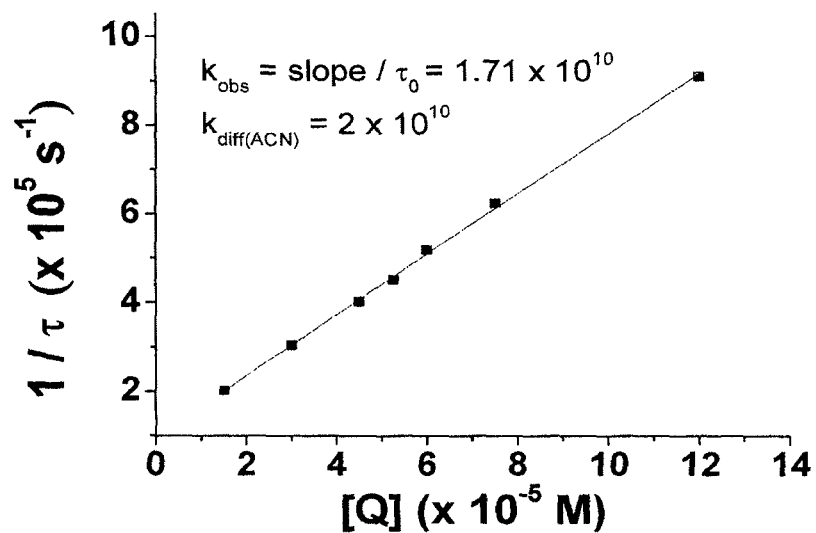
FIG. 5 shows a Stern-Volmer plot of the quenching study and the numerical fitting of $K_q$.

To study the energy transfer between two ions in C2A3, Stem-Volmer quenching analysis was carried out. The lifetime of A3 in degassed acetonitrile solution with various amounts of the quencher, C2, was recorded. The concentration of the A3 was kept at 0.67 μM in all samples and that of the quencher varied from 0 to 120 μM. Based on a bimolecular quenching model, the reciprocal of the lifetime is linearly correlated to the concentration of the quencher ([Q]), as observed for the C2 and A3 in FIG. 5. The quenching rate constant ($K_q$) can be extracted by dividing the slope of the fitted straight line by $\tau_0$ (the lifetime with no quencher present). The calculation yields a $K_q$ value of $1.71 \times 10^{10} M^{-1} s^{-1}$, close to the diffusion limit in acetonitrile ($2 \times 10^{10} M^{-1} s^{-1}$). (Turro, N. J., Modern Molecular Photochemistry. Benjamin/Cummings: Menlo Park, Calif., 1978). The data suggests this quenching process is effective in short range, leaving triplet-triplet energy transfer and electron transfer quenching as two possible mechanisms. (Ma, B.; Djurovich, P. I.; Thompson, M. E., Excimer and electron transfer quenching studies of a cyclometallated platinum complex. Coord. Chem. Rev. 2005, 249, 1501-1510). However, the PL and the HOMO/LUMO energy levels of both ions indicate that the energy transfer is the more likely explanation. This is because, first of all, A3 has a higher triplet energy than C2 does so that it is energetically favorable for energy transfer quenching to happen. Secondly, A3 also possesses the higher LUMO and deeper HOMO compared to C2. When A3 is excited, the energy alignment between two ions favors the electron exchange, instead of one-way electron transfer. The process essentially equates the energy transfer from A3 to C2 through the Dexter mechanism. When the concentration of C2 reaches a certain level, the average distance between A3 ions and surrounding C2 ions is within the effective range of triplet energy transfer. This inter-ion interaction leads to the elimination of most of the emission from A3, exampled by the spectrum at $10^{-3}$M in FIG. 4(b).

Quantum Yield.

The quantum yields (QY) of the soft salts and their component ions were measured in solution and as neat films (Table 1). In solution, the QY s increased significantly after degassing, consistent with the efficient oxygen quenching of phosphorescence from the complexes. The QYs of degassed solutions of C1A2 and C2A3 match the values of the ion with lower energy in the pair, consistent with the efficient energy transfer in soft salts. In films, the QY s are generally lower compared to the values observed in degassed solutions, as expected due to self quenching. It is interesting to see that the QY values are also sensitive to the size of the ligand and the counter ion. For example, soft salts generally possess higher QYs than their component ions in neat film, because the ions of the soft salts are markedly larger than halide or alkali metal ions, leading to larger intermolecular spacing in the soft salts. Similarly, a bulkier ligand can improve the QY by spacing the ions farther apart in the ionic solids, which explains why C2Cl has a higher QY than C1Cl in film samples even though their QYs are quite similar in solution.

HOMO and LUMO Energies.

The electrochemical properties of the soft salts and individual ions were examined by cyclic voltemmetry (CV). The measurements were performed in acetonitrile and ferrocene was used as the internal reference. HOMO/LUMO levels which were obtained from redox potentials based on the previously published correlations are summarized in Table 1. (D'Andrade, B. W. et al., Relationship between the ionization and oxidation potentials of molecular organic semiconductors. Organic Electronics 2005, 6 (1), 11-20; Djurovich, P. I. et al., Measurement of the lowest unoccupied molecular orbital energies of molecular organic semiconductors. Organic Electronics, 2009, 10 (3), 515-520.) The energy levels are also plotted in FIG. 6 for comparison purposes. According to the data, the HOMO/LUMO values of the ions are affected by both the net electrical charge and the chelating ligand. For example, C1A1 contains two ionic Ir complexes that have the same C^N chelating ligand, leading to very similar emission and absorption energies, while their HOMO and LUMO energy levels differ significantly. An anionic Ir complex (A1) is easier to be oxidized and harder to be reduced, which translates into a higher HOMO and LUMO than an analogous cationic complex (C1).

The HOMO and the LUMO energy of the soft salts are determined by the lowest energy potential of the pair of Ir complexes. This provides a simple solution to tuning the energy levels of the soft salts by changing the chelating ligands of the individual ions. The idea is seen in comparing C1A1 and C1A2. C1A2 is obtained by replacing the tolylpyridyl (tpy) group of A1 with phenylquinoline (PQ) groups, namely A2. In C1A2, the extended π-conjugation of the PQ ligand lowers the reduction potential more than the positive charge raises it. As a result, C1A2 has both of its lowest energy potentials on the anion, in contrast to C1A1 having the lowest energy oxidation and reduction from HOMO of the anion and LUMO of the cation, respectively. Using a similar strategy, the energy levels of C2A3 were tailored such that oxidation and reduction both took place on the cation. The ability to adjust the energy levels independently allows us to probe the role of carrier trapping on the cationic and anionic component of the soft salt on OLED properties.

OLED Studies.

Soft salts were tested in both single layer LEC and heterostructured OLEO devices. Typical LECs show delayed luminescence, which is a result of gradual charge accumulation at electrode/organic interface, facilitating charge injection. When soft salts were used in an LEC structure (anode/soft salt/cathode), characteristic LEC behavior was not observed. The soft salt LEC devices remained as an open circuit and failed to turn on under various voltages ranging from 2.5V to 7V after several hours. This can be explained by the absence of the small ions found in LECs which migrate in the applied electric field, facilitating the charge injection in functional LECs. Charge injection in these soft salt-based LECs is difficult and imbalanced without the Ohmic contact created by migrating mobile ions to establish a recombination zone in the middle of the soft salt layer. Addition of an ionic liquid to the soft salt layer, which has been shown to markedly lower the turn on times for LECs, does not improve the soft salt LEC properties in this case. (Pei, Q. et al., Polymer Light-Emitting Electrochemical-Cells. Science 1995, 269 (5227), 1086-1088; Pei, Q. B. et al., Polymer light-emitting electrochemical cells: In situ formation of a light-emitting p-n junction. Journal Of The American Chemical Society 1996, 118 (16), 3922-3929). While this simple device structure does not give efficient charge injection into the soft salt materials, carrier transport in the soft salt layer is expected to rely on redox reactions of charged iridium complexes, similar to LECs. Being a mixture of cation and anion themselves, soft salts are ambipolar and expected to transport both holes and electrons.

Figure 6:
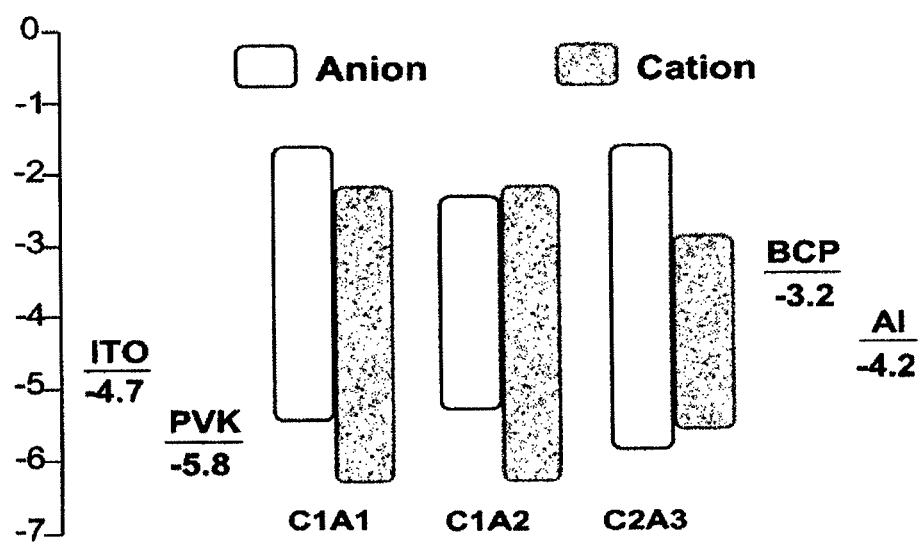
FIG. 6 shows energy levels of the materials used in the OLEDs.

To lower the hole injection barriers in soft-salt-based devices, a PVK layer was spin-coated on the ITO. This PVK layer also prevents agglomeration or crystallization of the soft salt layer. The PVK/soft salt layers were capped with a thin film of BCP to improve energy alignment between the cathode and the soft salts. The energy diagrams for these three soft-salt-based OLEDs are shown in FIG. 6. At the interface of PVK and soft salt, the holes are injected by oxidizing the anions and hop between anionic complexes inside the soft salt layer. The charge localization in soft salt layers is quite different from that of the neutral materials typically used in OLEDs. In contrast to the typical OLEDs, where the hole is present as a positive polaron, the hole in the soft salt film forms a neutral species (oxidation of the anion) and the positive charge is delocalized over the lattice, as it is represented by an excess of cations over what is needed for the number of anions. The same is true for the electron, which corresponds to an excess of anions over what is needed to compensate the number of cations in the lattice, after the electron is injected. Conduction of charges through the soft salt is expected to be higher than an analogous neutral lattice, due to the higher dielectric of the highly-charged soft salt lattice. When a hole and an electron are localized on adjacent molecules, the excess positive and negative lattice charge associated with each carrier are neutralized and the two carriers are expected to be bound, just as positive and negative polarons can be electrostatically attracted and bound in a neutral lattice.

Figure 7:
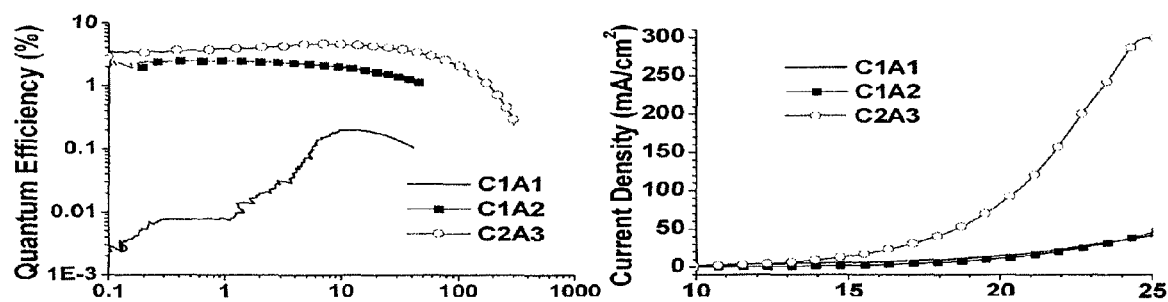
FIG. 7 shows EQE (left panel) and J-V characteristics (right panel) of the devices using different soft salts.

The relative position of the energy levels between two ions in the soft salt is crucial to device performance. The component ions of C1A1 consist of the same cyclometallating ligand, but different ancillary ligands, the latter imparting the charge to the complex. The two ions have similar HOMO/LUMO gaps, but the molecular charges markedly shift the HOMO and LUMO energies. Because the energy barriers between two HOMOs and two LUMOs are both relatively high, it is difficult for carriers to be exchanged between the reduced cation (the electron) and the oxidized anion (the hole), which hinders exciton formation. As a result, there is no obvious preference for recombination to take place on one ionic complex over the other. Although C1A1 has the lowest PL QY in neat film among three soft salts, the 0.2% EQE of the C1A1-based device is far lower than would be expected based on the PL efficiency alone. This suggests that poor matching of the HOMO/LUMO is the principal reason why C1A1 demonstrates the poorest performance among all three soft salts (FIG. 7 and Table 2). In contrast to C1A1, C1A2 and C2A3 have a close energy match between one of the frontier orbitals, close LUMO match for C1A3 and close HOMO match for C2A3. Moreover, in these two soft salts, the energy levels of one ion are bracketed by those of the other, suggesting that one of the ions may carry both the hole and electron. Thus, there is a preference energetically to generate excitons on the ion with the smaller energy gap. The anion of C1A2 and the cation of C2A3 serve as a trap for both holes and electrons, which improves the efficiency of exciton formation. The advantage of this energetic configuration is reflected in the markedly higher EQE values for C1A2 and C2A3, i.e. 2.6 and 4.7%, respectively (FIG. 7, left panel). Compared to the QY data of the films in Table 1, the maximum EQE value of the devices made using C1A2 and C2A3 (Table 2) is comparable to the theoretical maximum (the internal efficiency is expected to be 3-5 times higher than EQE). (Hung, L. S.; Chen, C. H., Recent progress of molecular organic electroluminescent materials and devices. Materials Science & Engineering R-Reports 2002, 39 (5-6), 143-222.)

Despite the good EQE, the device using C1A2 shows lower conductivity to the one using C2A3 (FIG. 7, right panel). A similar trend can be seen in the brightness and turn-on voltage data (Table 2). The difference likely stems from the energy barrier for electron injection. The LUMO of the cation of C1A2 (−1.94 eV) is 0.6 eV higher than that of the cation in C2A3 (−2.54 eV), creating a larger barrier for electron injection from BCP. In contrast, the effect on hole injection from the energy difference between HOMO of VK and the HOMO levels of two anions is comparable, based on the energy diagram (FIG. 6). Among the three soft salts, C2A3 offers the best HOMO/LUMO match-up with hole and electron injection layer, and the energy levels between its component ions also facilitate the charge recombination. The device data for C2A3-based OLEDs suggests that soft salts have the potential to prepare OLEDs with properties comparable to those made with neutral Ir phosphors.

TABLE 2

Performance of the OLEDs made using different salts.

| | $\lambda_{max, EL}$ (nm) | $V_{turn-on}$ (V) | $L_{max}$ (Cd/m$^2$) | $\eta_{ext, max}$ (%) |
|---|---|---|---|---|
| C1A1 | 510 | 4 | 160 (24 V) | 0.2 |
| C1A2 | 590 | 3 | 1971 (24 V) | 2.6 |
| C2A3 | 586 | 2.5 | 7428 (21 V) | 4.7 |

Ir-based soft salts have been synthesized and characterized. Because each soft salt is formed by a pair of ionic Ir complexes, through independently altering the ligands, the relative energetic properties, which have significant impact on the photophysical, electrochemical and device performance, are easily tuned. For example, C2A3 shows the dual emission in solution, with the ratio of two components in the spectrum dependent on the soft salt concentration. Quenching studies show that the energy transfer process from the blue to red emissive ion is at diffusion controlled limit. The internal match-up between the energy levels of two ions is key to achieving good OLEO performance. C2A3 gives the best overall device performance with the maximal EQE of 4.7%, comparable to the theoretical maximum based on the film PL efficiency. This result suggests that the soft-salt-based devices have the potential to reach efficiencies comparable to neutral Ir-based OLEDs. The key to achieving such high efficiencies is the preparation of soft salts with thin film PL efficiencies in the 0.5-1.0 range, which are readily achieved for Ir-phosphor-doped thin films.

Organometallic soft salt compounds are provided, the compounds comprising the formula:

$$\sum_{i=1}^{m} C_i^{ai+} \sum_{j=1}^{n} C_j^{bj-}.$$

$C_i^{ai+}$ is an organometallic cation having formula $C_i$ with $a_i$ positive charge.

$C_j^{bj-}$ is an organometallic anion having formula $C_j$ with $b^j$ negative charge.

$C_i$ is $(L_i)_f M_i X_i$; formula $C_j$ is $(L_j)_g M_j X_j$. Each of $M_i$ and $M_j$ is independently a transition metal or a lanthanide. Each of $L_i$ and $L_j$ is independently a mono-, di-, tri- or polydentate ligand. Each of f and g may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

This formula is another way of expressing the same soft salt compounds described by Formula I, above.

In one aspect, the compound has the formula $$\sum_{i=1}^{m} C_i^{ai+} \sum_{j=1}^{n} C_j^{bj-},$$

as described above.

In one aspect, each of $M_i$ and $M_j$ are Ir. However, it is possible to use Ir(I) or Ir(III) as the transition metal in the inventive compounds. In another aspect, each of $M_i$ and $M_j$ are Ir(III).

In one aspect, the organometallic cation has the formula:

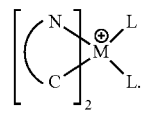

In another aspect, the organometallic anion has the formula:

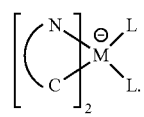

Each

independently represents a bonded pair of aromatic or heteroaromatic rings coordinated to the metal via a nitrogen atom and an sp² hybridized carbon atom.

In one aspect,

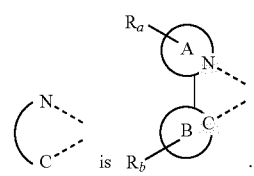

A and B are each independently a 5 or 6-membered aromatic or heteroaromatic ring. A-B represents a bonded pair of aromatic or heteroaromatic rings coordinated to the metal via a nitrogen atom on ring A and an sp² hybridized carbon atom on ring B. Each of $R_a$ and $R_b$ may represent mono, di, tri, or tetra substituents. Each of $R_a$ and $R_b$ substituent are independently selected from a group consisting of hydrogen, deuterium, alkyl, heteroalkyl, aryl, or heteroaryl. Two adjacent substituents may form a ring.

Each

is independently selected from the group consisting of:

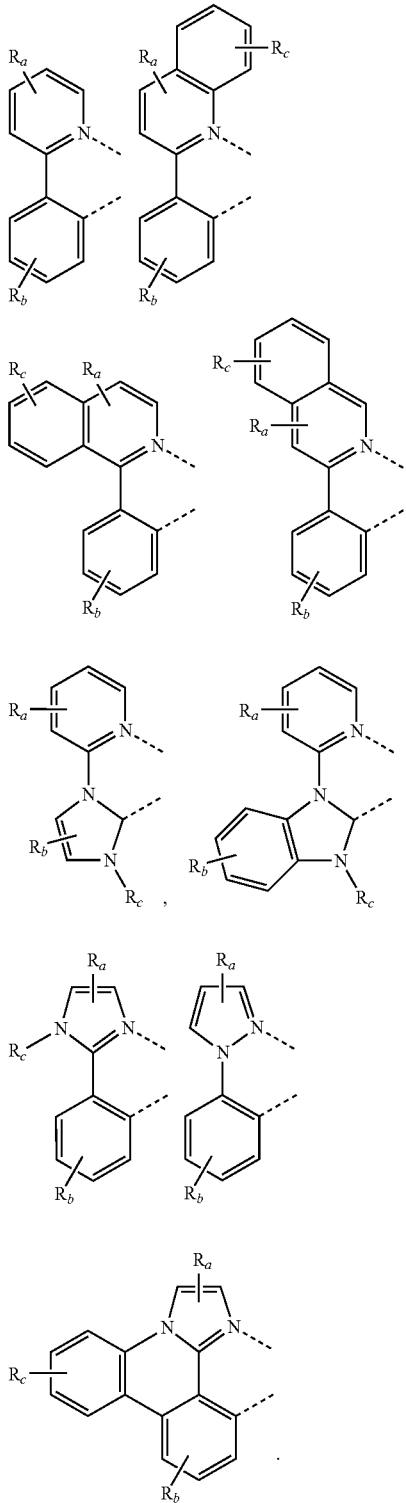

Each of $R_a$, $R_b$ and $R_c$ may represent mono, di, tri, or tetra substituents. Each of $R_a$, $R_b$ and $R_c$ substituent are independently selected from a group consisting of hydrogen, deuterium, alkyl, heteroalkyl, aryl, or heteroaryl. Two adjacent substituents may form into a ring.

Each of $L_i$ and $L_j$ are independently selected from the group consisting of:

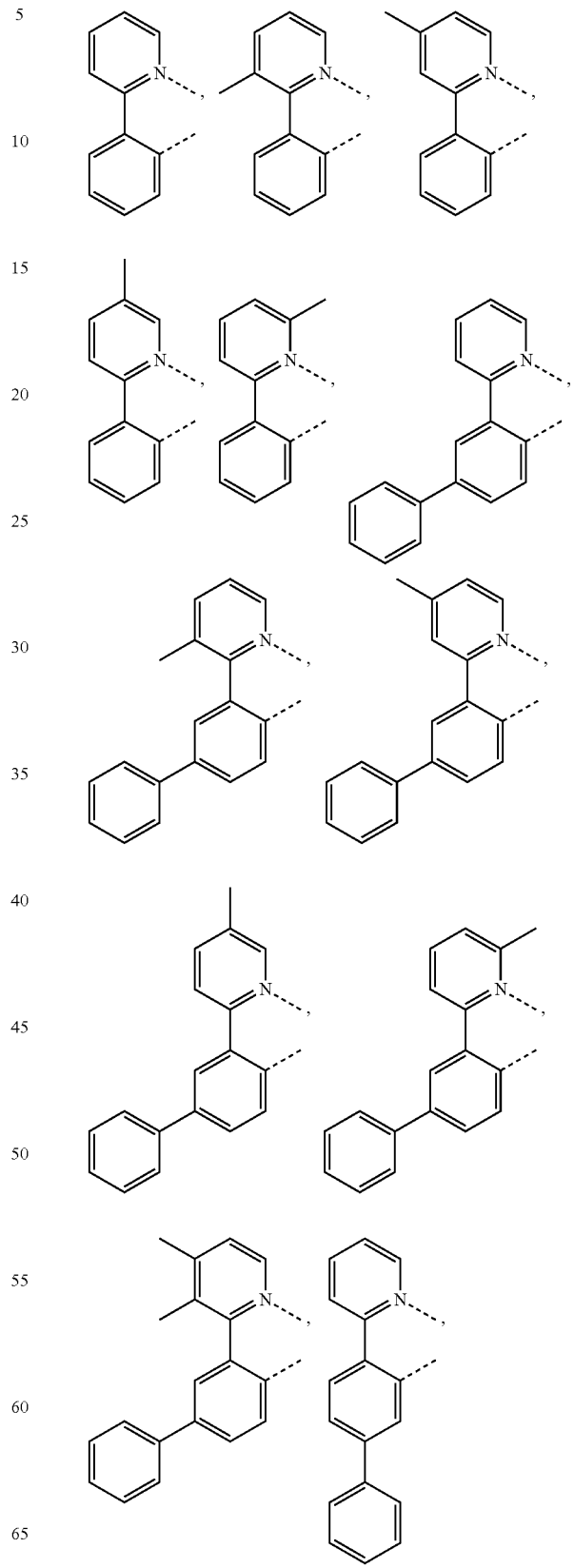

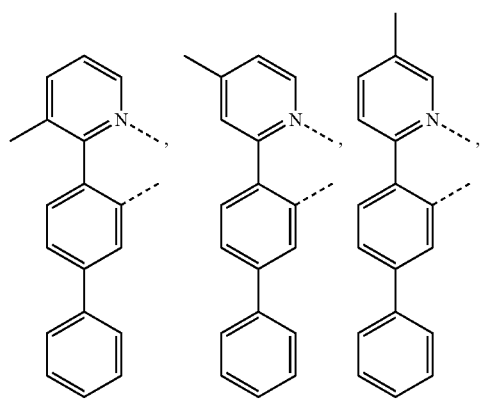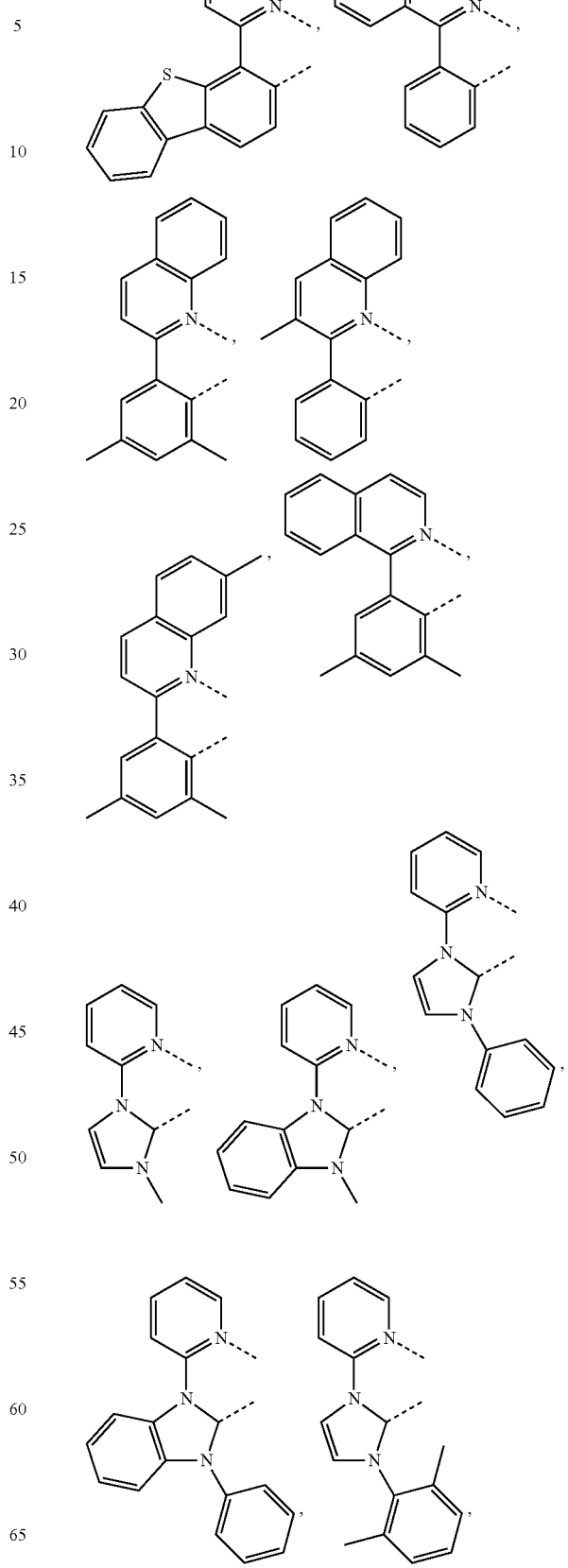

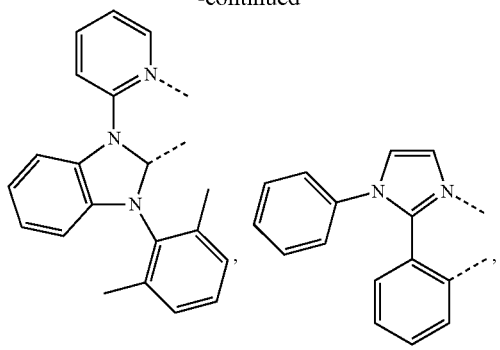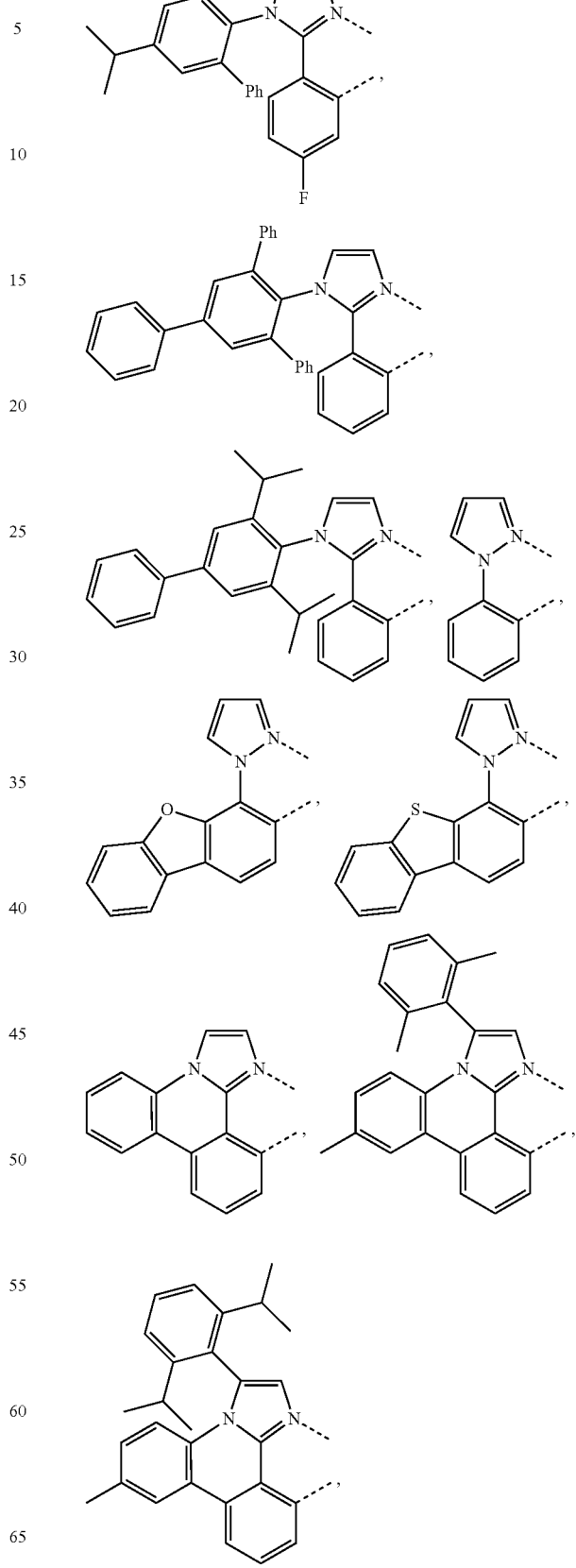

-continued

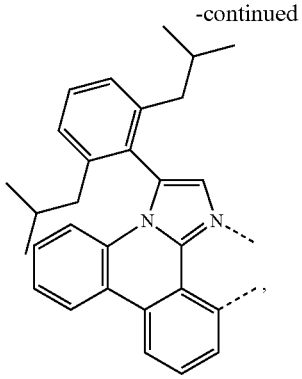

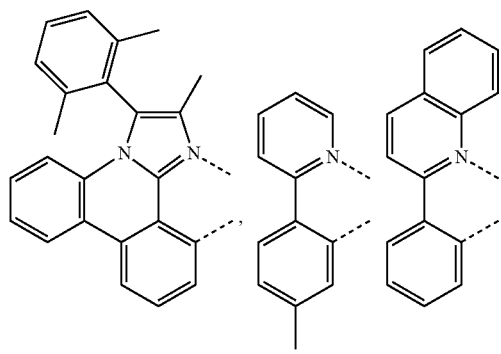

Preferably, each of $L_i$ and $L_j$ are independently selected from the group consisting of:

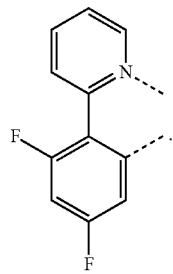

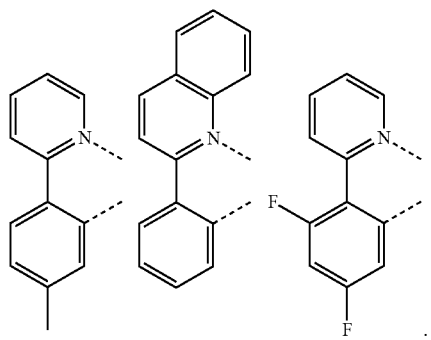

In one aspect, each of the organometallic cations in the compound are the same and each of the organometallic anions in the compound are the same.

In yet another aspect, the organometallic anion is selected from the group consisting of:

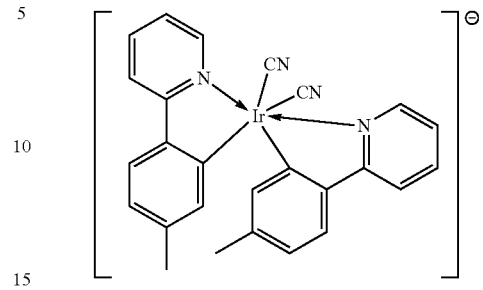

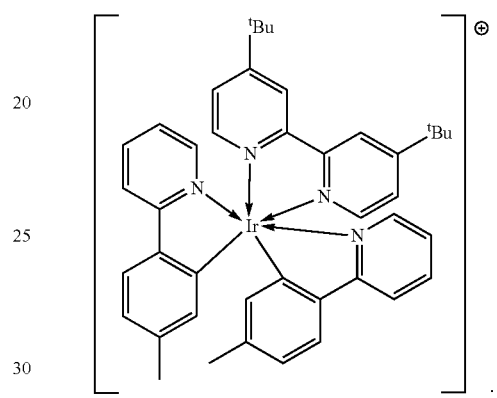

In a further aspect, organometallic cation is selected from the group consisting of:

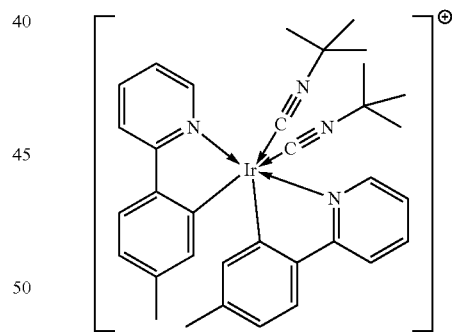

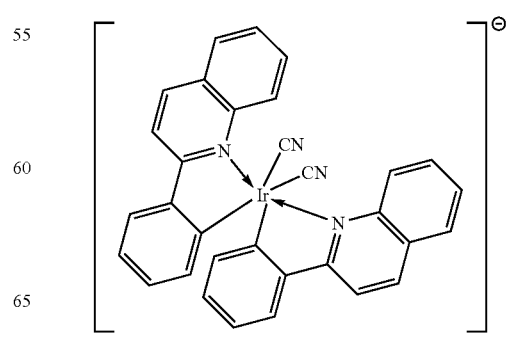

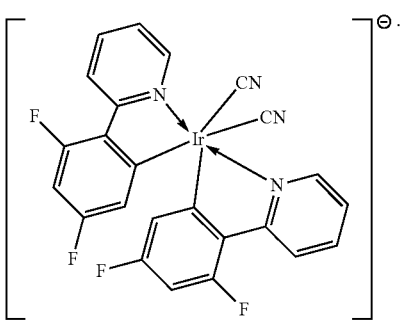

Specific examples of the compounds are provided. In one aspect, the compound is selected from the group consisting of:

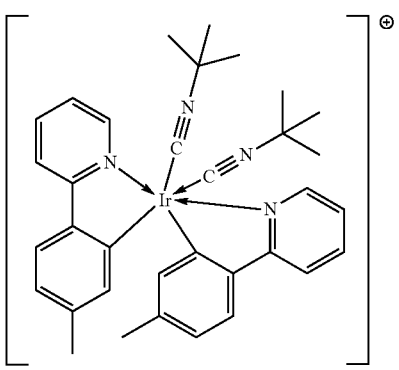

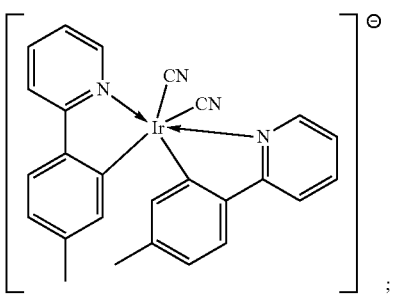

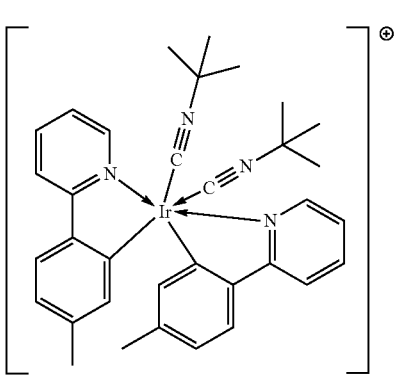

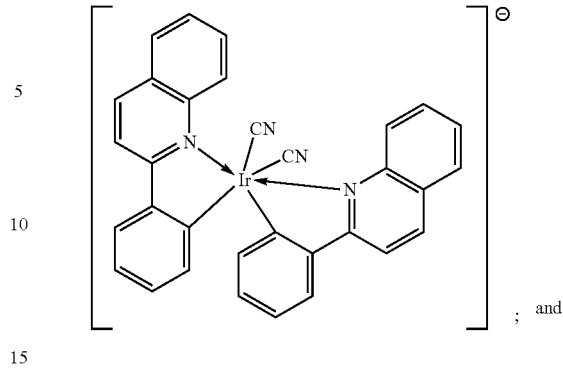

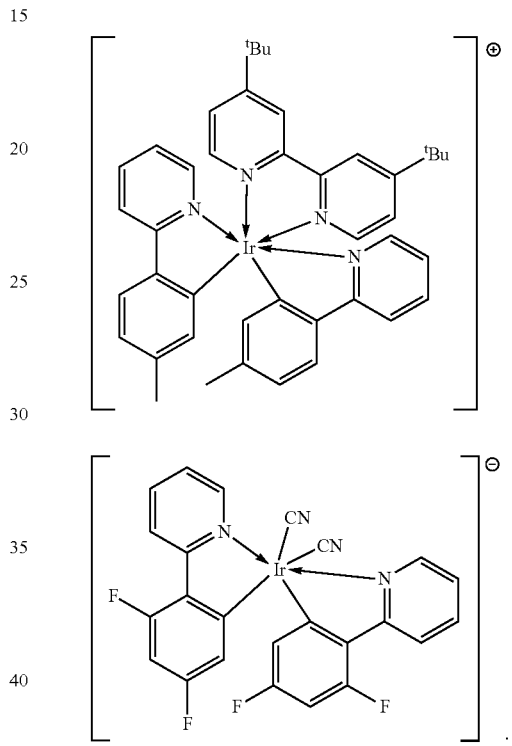

Additionally, a first device comprising an organic light emitting device is provided. The organic light emitting device comprises an anode, a cathode, and an organic layer, disposed between the anode and the cathode. The organic layer further comprises a compound having the formula:

$$\sum_{i=1}^{m} C_i^{a_i+} \sum_{j=1}^{n} C_j^{b_j-}.$$

$C_i^{a_i+}$ is an organometallic cation having formula $C_i$ with $a_i$ positive charge.

$C_j^{b_j-}$ is an organometallic anion having formula $C_j$ with $b_j$ negative charge.

$C_i$ is $(L_i)_f M_i X_i$; formula $C_j$ is $(L_j)_g M_j X_j$. Each of $M_i$ and $M_j$ is independently a transition metal or a lanthanide. Preferably, each of $M_i$ and $M_j$ are Ir. Each of $L_i$ and $L_j$ is independently a mono-, di-, tri- or polydentate ligand. Each of f and g may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

In one aspect, the organometallic cation has the formula:

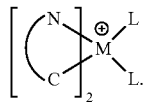

In another aspect, the organometallic anion has the formula:

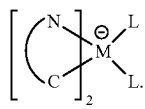

Each

independently represents a bonded pair of aromatic or heteroaromatic rings coordinated to the metal via a nitrogen atom and an sp² hybridized carbon atom.

In one aspect,

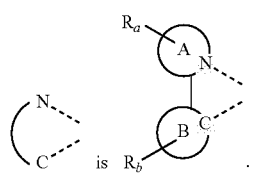

A and B are each independently a 5 or 6-membered aromatic or heteroaromatic ring. A-B represents a bonded pair of aromatic or heteroaromatic rings coordinated to the metal via a nitrogen atom on ring A and an sp² hybridized carbon atom on ring B. Each of $R_a$ and $R_b$ may represent mono, di, tri, or tetra substituents. Each of $R_a$ and $R_b$ substituent are independently selected from a group consisting of hydrogen, deuterium, alkyl, heteroalkyl, aryl, or heteroaryl. Two adjacent substituents may form into a ring.

Each

is independently selected from the group consisting of:

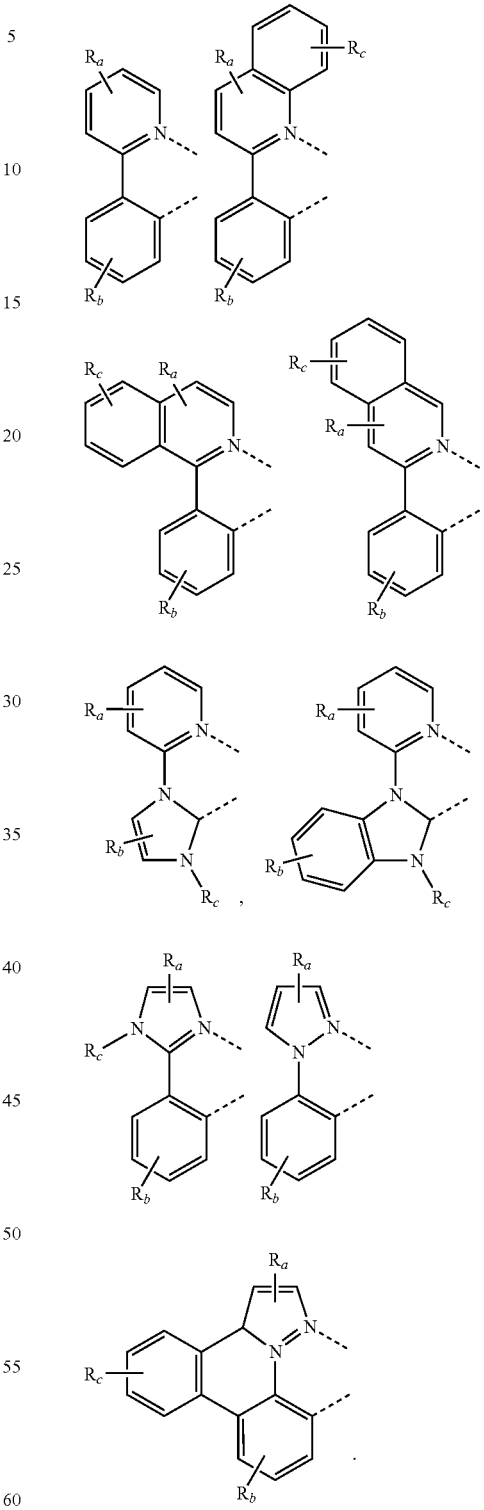

Each of $R_a$, $R_b$ and $R_c$ may represent mono, di, tri, or tetra substituents. Each of $R_a$, $R_b$ and $R_c$ substituent are independently selected from a group consisting of hydrogen, deuterium, alkyl, heteroalkyl, aryl, or heteroaryl. Two adjacent substituents may form into a ring.

Each of $L_i$ and $L_j$ are independently selected from the group consisting of:
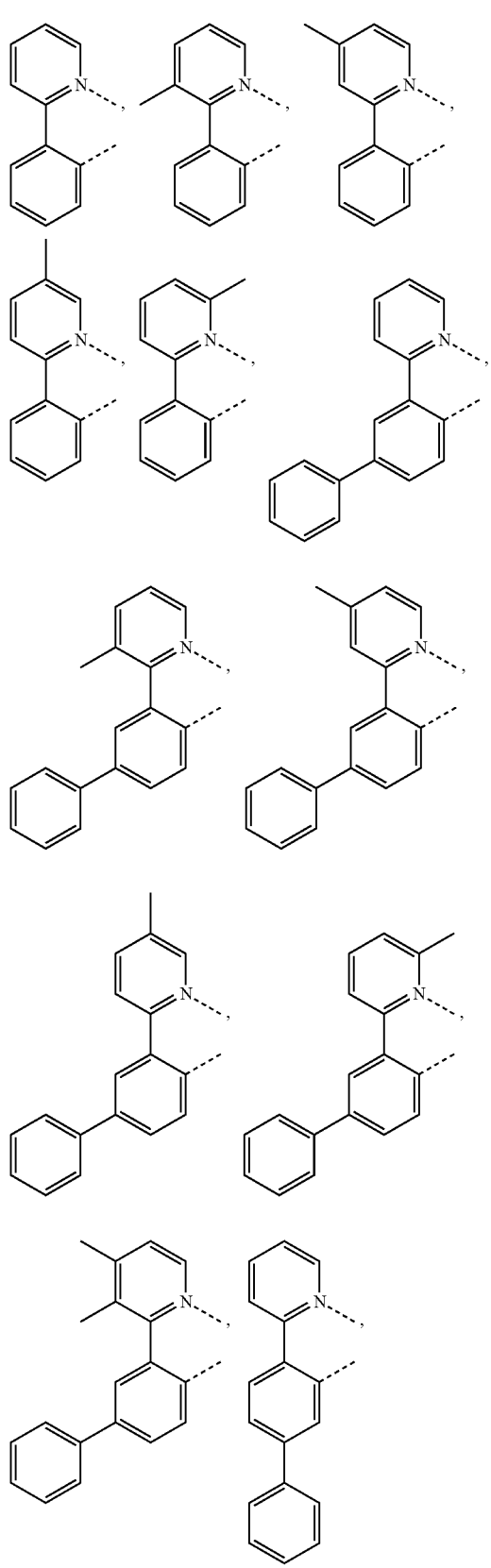
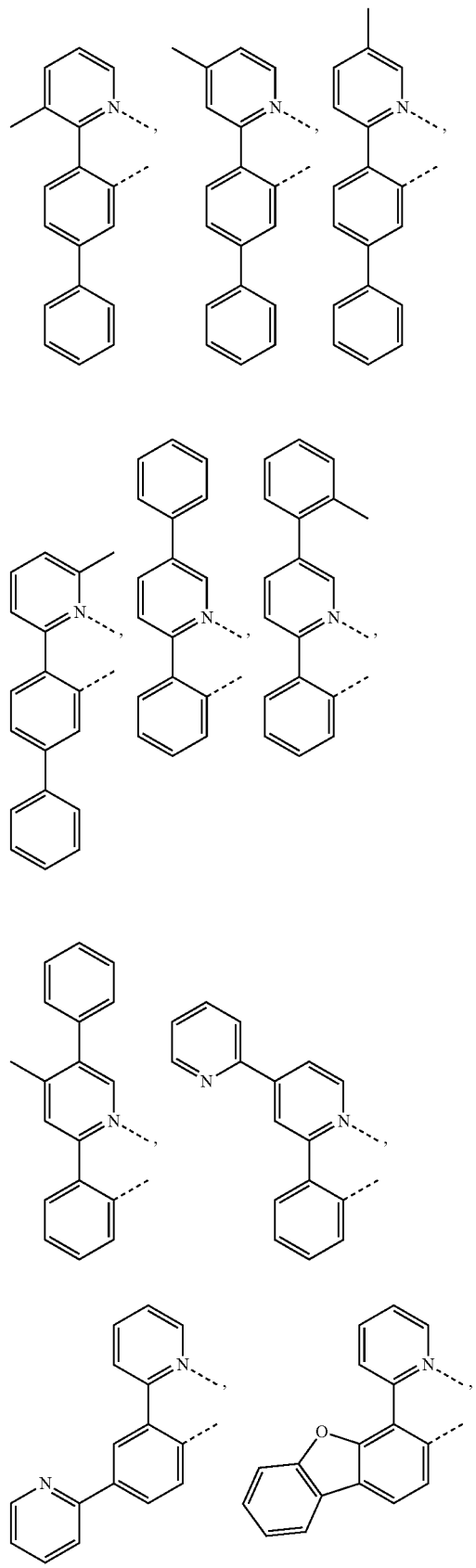

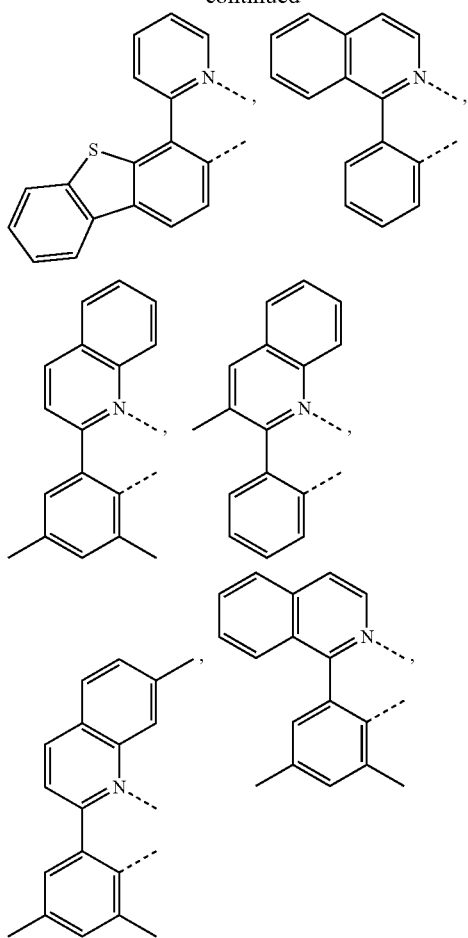
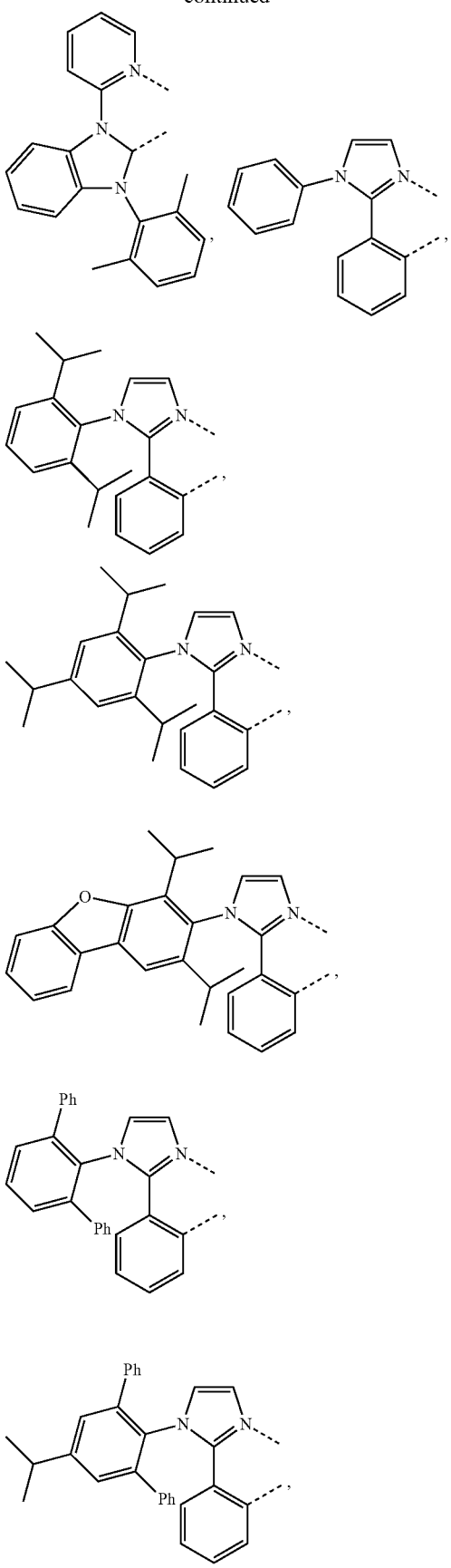

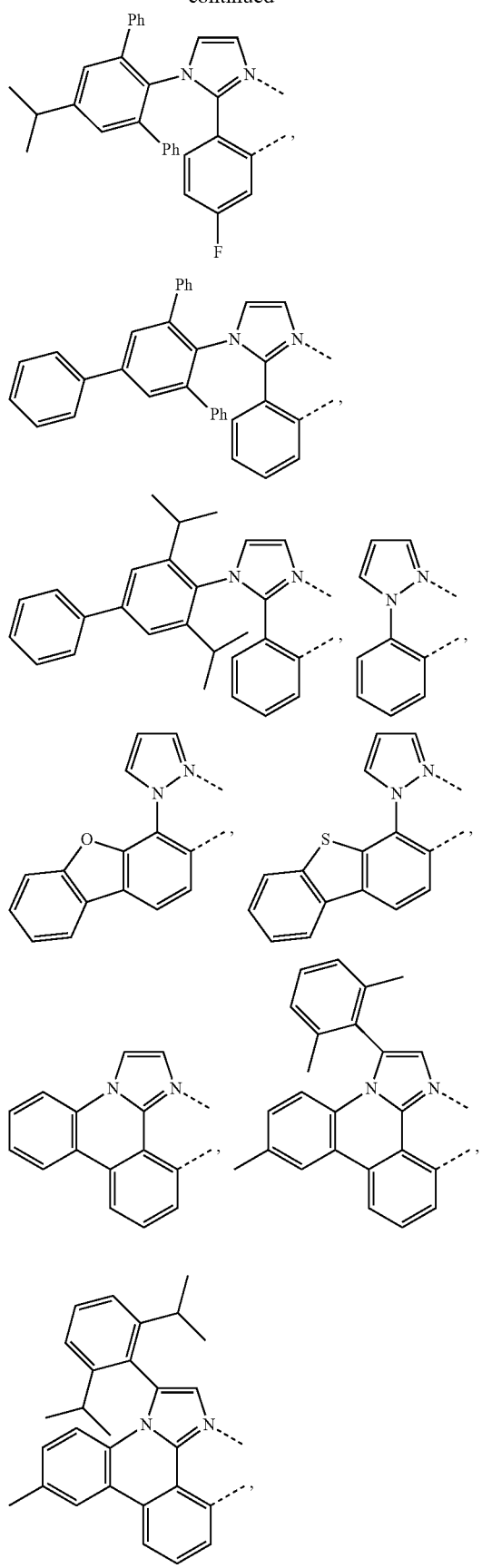
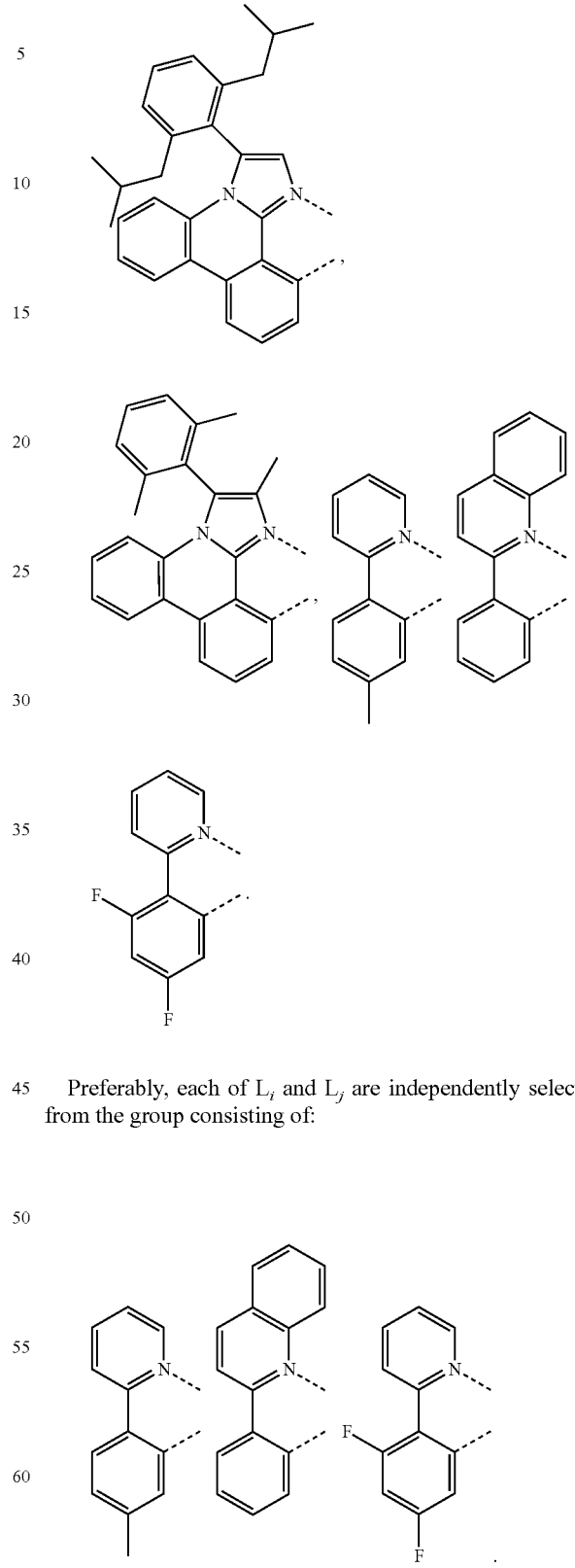
Preferably, each of $L_i$ and $L_j$ are independently selected from the group consisting of:
In yet another aspect, the organometallic anion is selected from the group consisting of:

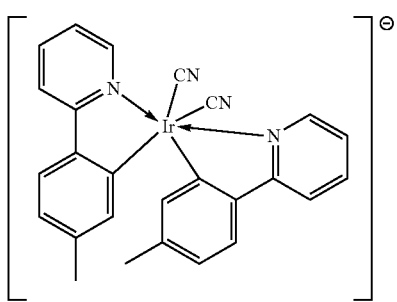
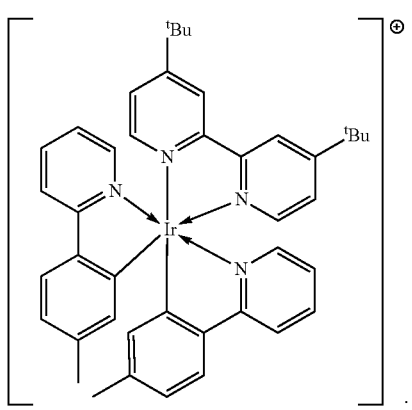
In a further aspect, organometallic cation is selected from the group consisting of:
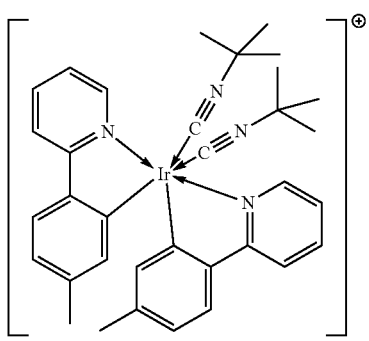
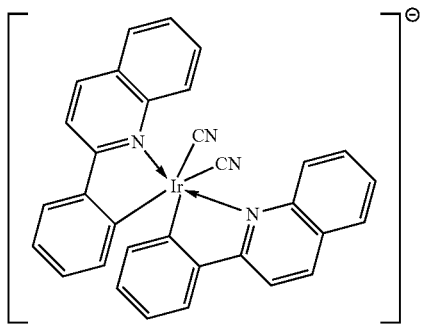
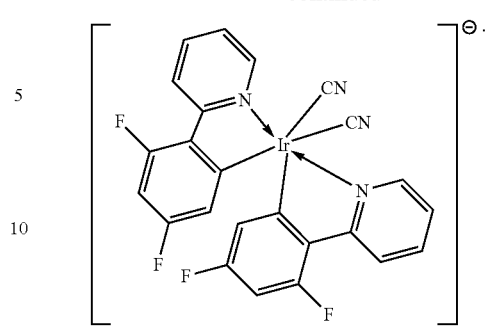
Specific examples of the devices are provided. In one aspect, the compound is selected from the group consisting of:
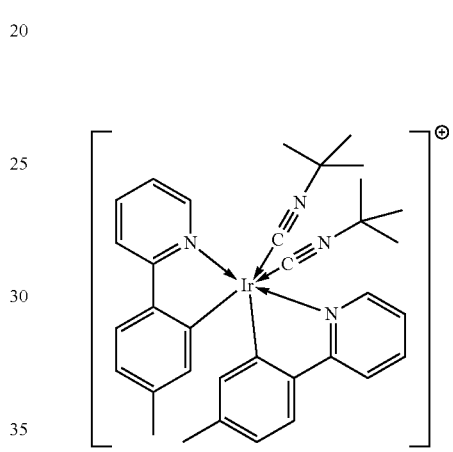
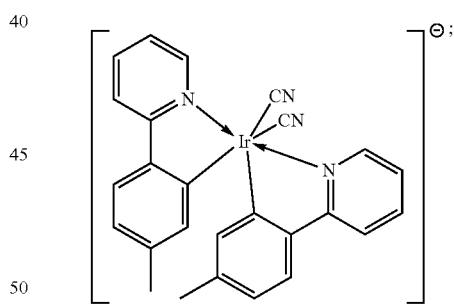
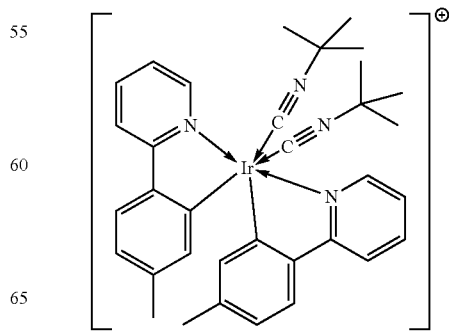

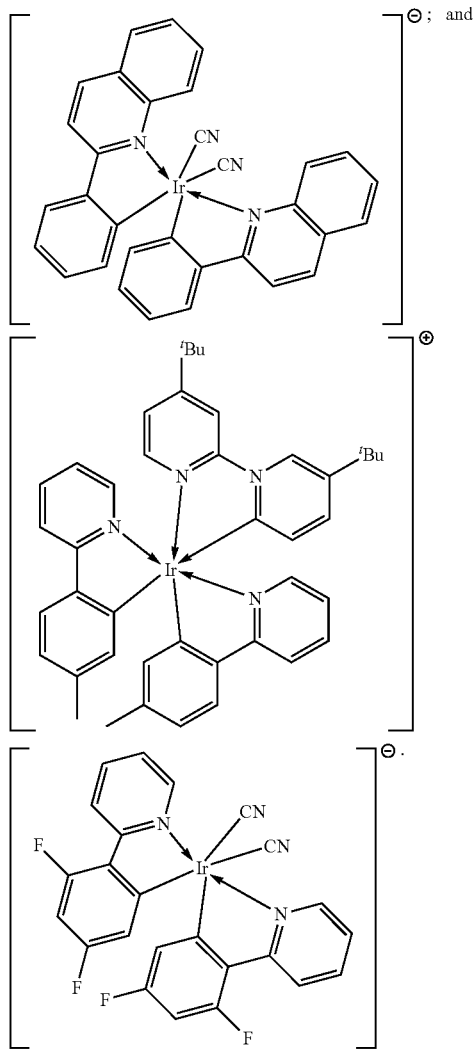

In one aspect, the organic layer is deposited using vapor disposition.

In another aspect, one of the organometallic anion and the organometallic cation has both the lower oxidation potential and a less negative reduction potential than the other. In other words, one of the ions of the soft salt, either the cation or anion, traps and carries both the hole and the electron.

In yet another aspect, PVK is mixed with dichlorobenzene and deposited prior to depositing the organic layer.

In a further aspect, a film comprising BCP is deposited over the organic layer.

In one aspect, the first device is an organic light emitting device. In another aspect, the first device is an organic light emitting cell.

A method of making the organometallic soft salt compounds is also provided. The method comprises obtaining an organometallic complex having the formula:

$$\sum_{i=1}^{m} C_i^{a_i+} \sum_{j=1}^{n} C_j^{b_j-},$$

by reacting an organometallic cation having the formula:
$C_i^{a_i+}$ with $a_i$ positive charge, with an organometallic anion has the formula:
$C_j^{b_j-}$ with $b_j$ negative charge.

$C_i$ is $(L_i)_f M_i X_i$; and formula $C_j$ is $(L_j)_g M_j X_j$. Each of $M_i$ and $M_j$ is independently a transition metal or a lanthanide. Each of $L_i$ and $L_j$ is independently a mono-, di-, tri- or polydentate ligand. Each of $_f$ and $_g$ may represent bis or tris ligand coordination. $X_i$ and $X_j$ represent any number of chelated or auxiliary ligands.

$$\sum_{i=1}^{m} a_i = \sum_{j=1}^{n} b_j.$$

m and n are integers of 1 to 20.

In one aspect, the organometallic cation and the organometallic anion are obtained by: reacting

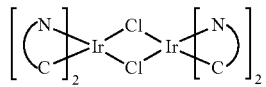

with a neutral ancillary ligand and an anionic ancillary ligand.

In another aspect, the organometallic cation and the organometallic anion are oxidized and reduced to form neutral metallated complexes before reaction to obtain the organometallic complex.

In yet another aspect, the neutral metallated complexes are thermally vacuum deposited in combination onto a substrate wherein the reaction is completed to obtain the organometallic complex.

In a further aspect, the method further comprises providing a first electrode, depositing the organometallic cation and the organometallic anion over the first electrode, and depositing a second electrode.

In one aspect, the first electrode is an anode and the second electrode is a cathode.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in embodiments of the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

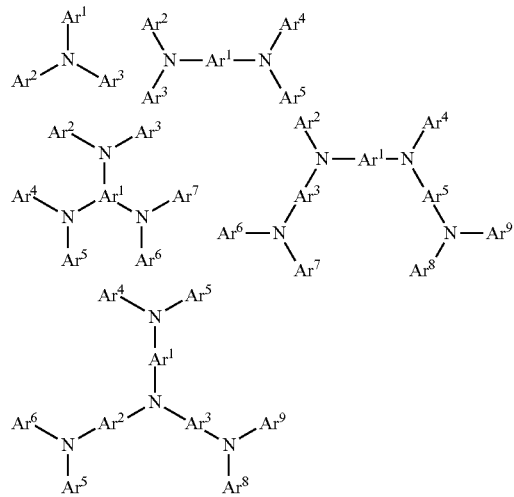

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, alkyl, alkoxy, amino, alkenyl, alkynyl, arylalkyl, heteroalkyl, aryl and heteroaryl.

In one aspect, $Ar^1$ to $Ar^9$ is independently selected from the group consisting of:

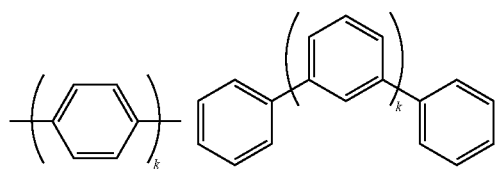

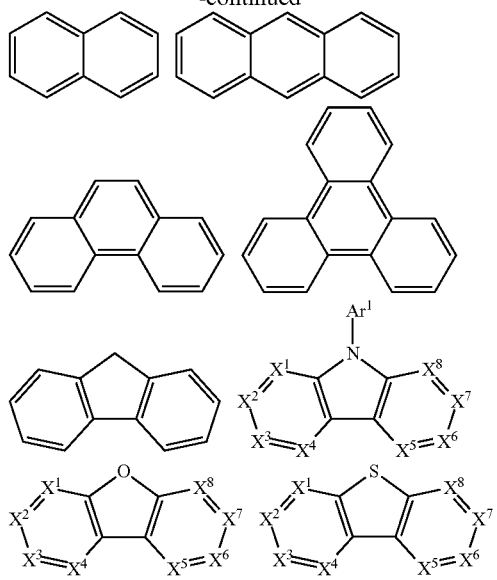

k is an integer from 1 to 20; $X^1$ to $X^8$ is CH or N; $Ar^1$ has the same group defined above.

Examples of metal complexes used in HIL or HTL include, but not limit to the following general formula:

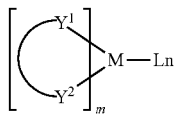

M is a metal, having an atomic weight greater than 40; $(Y^1-Y^2)$ is a bidentate ligand, Y1 and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

Host:

The light emitting layer of the organic EL device in embodiments of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

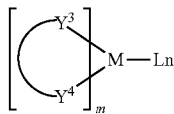

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

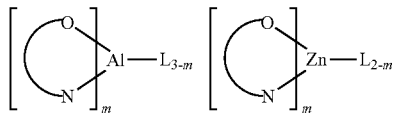

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, alkyl, alkoxy, amino, alkenyl, alkynyl, arylalkyl, heteroalkyl, aryl and heteroaryl.

In one aspect, host compound contains at least one of the following groups in the molecule:

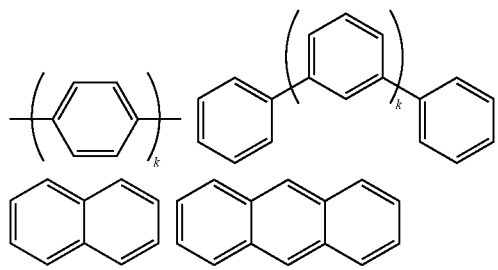

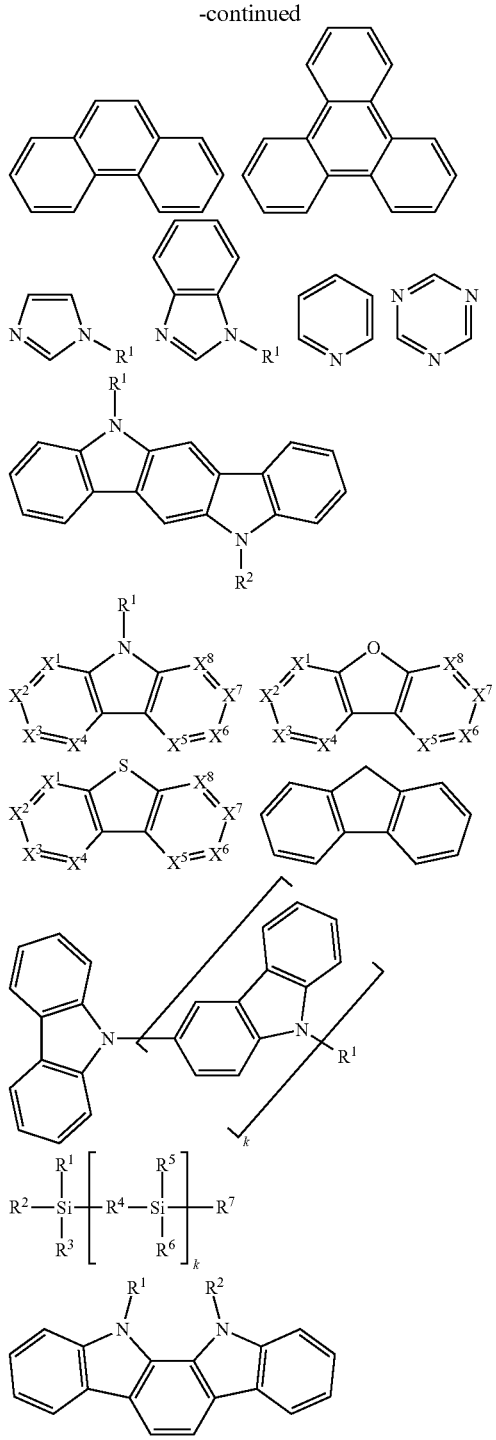

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from CH or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

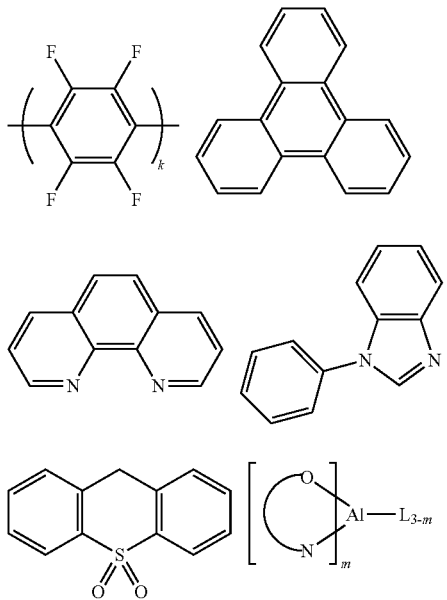

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

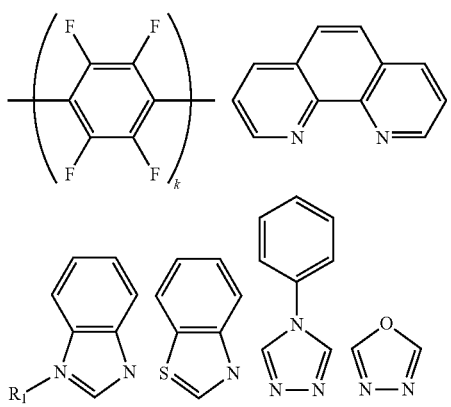

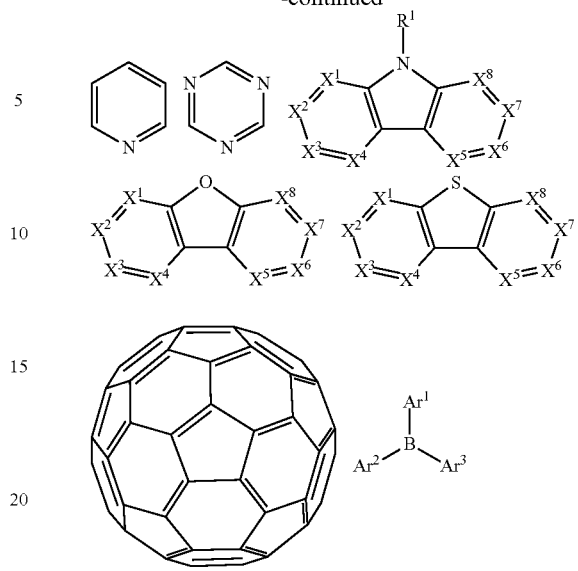

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from CH or N.

In another aspect, the metal complexes used in ETL contains, but not limit to the following general formula:

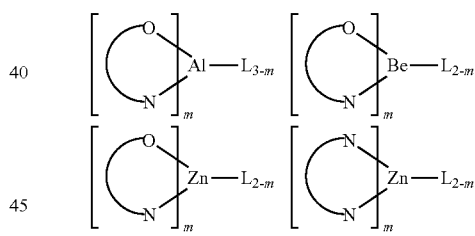

(O—N) or (N—N) is a bidentate ligand, having metal coordinated to atoms O, N or N, N; L is an ancillary ligand; m is an integer value from 1 to the maximum number of ligands that may be attached to the metal.

In any one of the above mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triaylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT: PSS, polyaniline, polypthiophene) | | Synth. Met. 87, 171 (1997) WO2007002683 |
| Phosphonic acid an sliane SAMs | | US20030162053 |

TABLE 3-continued
| MATERIAL | EXAMPLES OF MATERIAL | PUBLICATIONS |
|---|---|---|
| Triarylamine or polythiophene polymers with conductivity dopants | 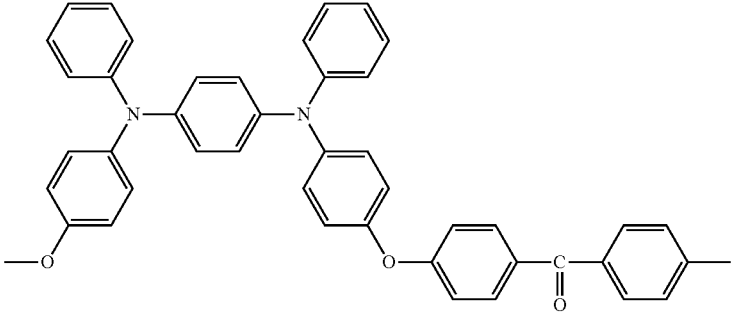 and 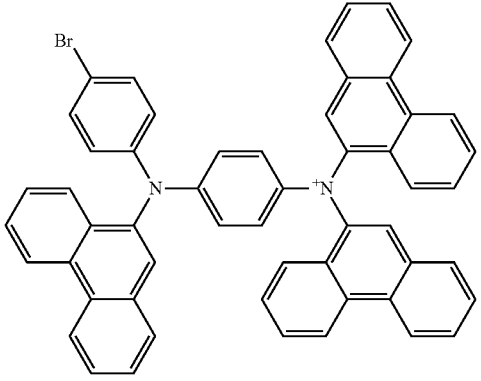 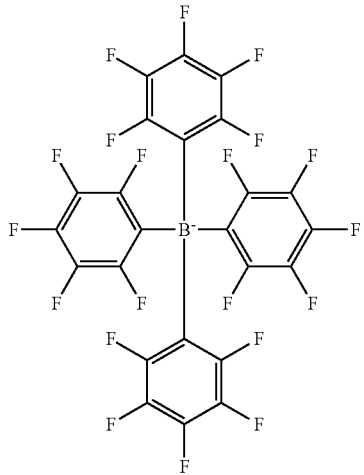 | EA01725079A1 |
| Arylamines complexed with metal oxides such as molybdenum and tungsten oxides | 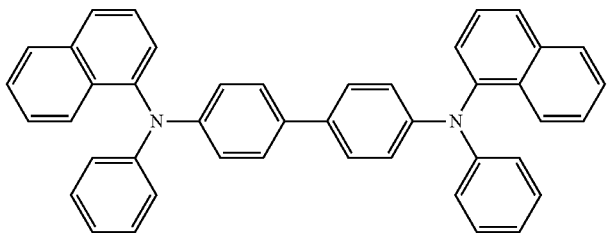 + $MoO_x$ | SID Symposium Digest, 37, 923 (2006) WO2009018009 |

TABLE 3-continued
| MATERIAL | EXAMPLES OF MATERIAL | PUBLICATIONS |
|---|---|---|
| p-type semiconducting organic complexes | 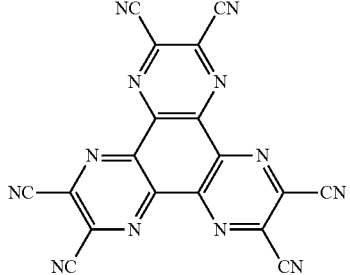 [SMILES: N#Cc1nc2c3nc(C#N)c(C#N)nc3c3nc(C#N)c(C#N)nc3c2nc1C#N] | US 20020158242 |
| Metal organometallic complexes | 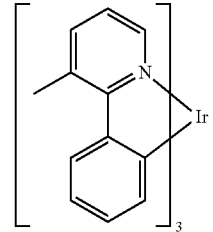 | US20060240279 |
| Cross-linkable compounds | 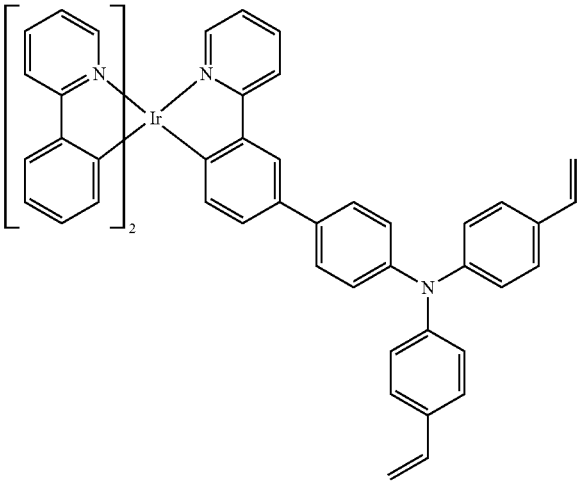 | US20080220265 |
| Hole transporting materials | | |
| Triarylamines (e.g., TPD, □-NPD) | 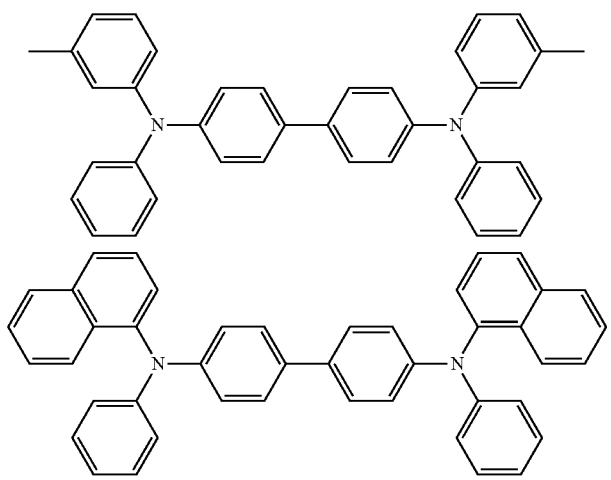 | Appl. Phys. Lett. 51, 913 (1987)<br><br>US5061569 |

TABLE 3-continued
| MATERIAL | EXAMPLES OF MATERIAL | PUBLICATIONS |
|---|---|---|
| | 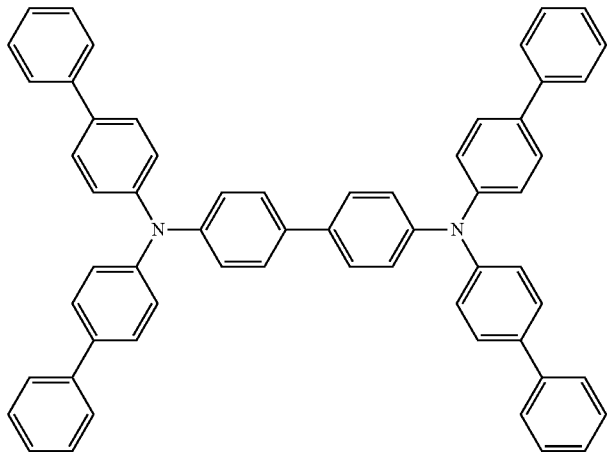 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 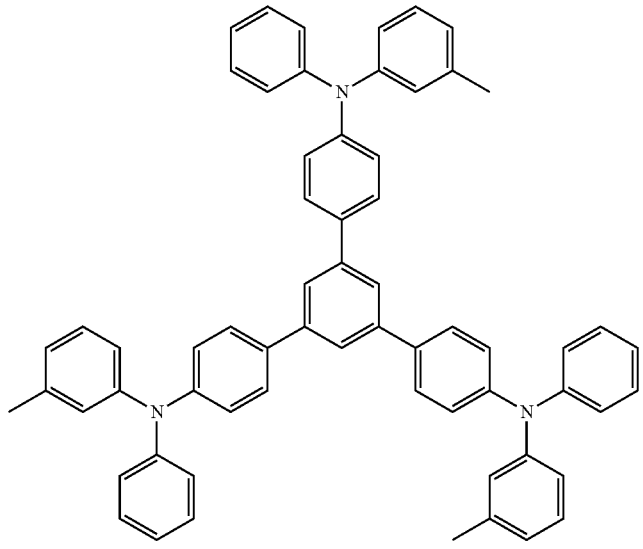 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 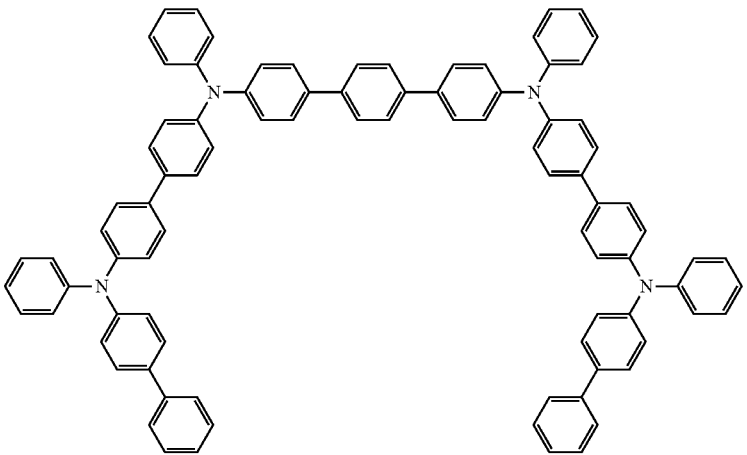 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 3-continued

| MATERIAL | EXAMPLES OF MATERIAL | PUBLICATIONS |
|---|---|---|
| | (structure) | Appl. Phys. Lett. 90, 183503 (2007) |
| Triaylamine on spirofluorene core | (structure) | Synth. Met. 91, 209 (1997) |
| Arylamine carbazole compounds | (structure) | Adv. Mater. 6, 677 (1994), US20080124572 |
| Triaylamine with (di) benzothiophene/ (di) benzofuran | (structure) | US20070278938 US20080106190 |

TABLE 3-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED hose materials

| Arylcarbazoles | | Appl. Phys. Lett. 78, 1622 (2001) |
| --- | --- | --- |
| Metal 8-hydroxyquinolates (e.g., Alq$_3$, BAlq) | | Nature 395, 151 (1998) |

TABLE 3-continued

| MATERIAL | EXAMPLES OF MATERIAL | PUBLICATIONS |
|---|---|---|
| | (structure) | US20060202194 |
| | (structure) | WO2005014551 |
| | (structure) | WO2006072002 |
| Metal phenoxy-benzothiazole compounds | (structure) | Appl. Phys. Lett. 90, 123509 (2007) |
| Conjugated oligomers and polymers (e.g., polyfluorene | (structure) | Org. Electron. 1, 15 (2000) |
| Aromatic fused rings | (structure) | WO2009066779, WO2009066778, WO2009063833, US20090045731, US20090045730, WO2009008311, US20090008605, US20090009065 |

TABLE 3-continued

| MATERIAL | EXAMPLES OF MATERIAL | PUBLICATIONS |
| --- | --- | --- |
| Zinc complexes | | WO2009062578 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 3-continued
| MATERIAL | EXAMPLES OF MATERIAL | PUBLICATIONS |
|---|---|---|
| | 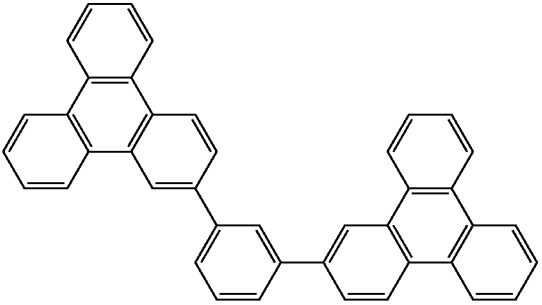 [SMILES: c1cc(-c2ccc3c4ccccc4c4ccccc4c3c2)cc(-c2ccc3c4ccccc4c4ccccc4c3c2)c1] | US20060280965 |
| | 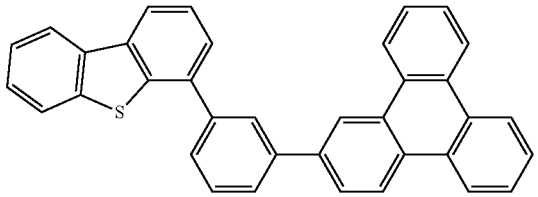 [SMILES: c1cc(-c2ccc3c4ccccc4c4ccccc4c3c2)cc(-c2cccc3c2sc2ccccc23)c1] | WO2009021126 |
| Donor acceptor type molecules | 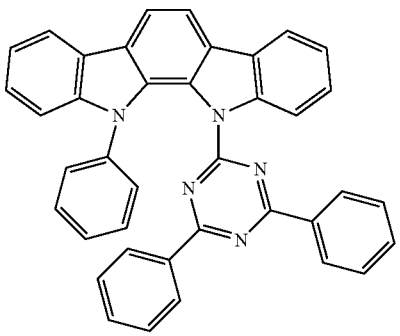 [SMILES: c1ccc(-c2nc(-c3ccccc3)nc(-n3c4ccccc4c4ccc5c6ccccc6n(-c6ccccc6)c5c43)n2)cc1] | WO2008056746 |
| Aza-carbazole/DBT/DBF | 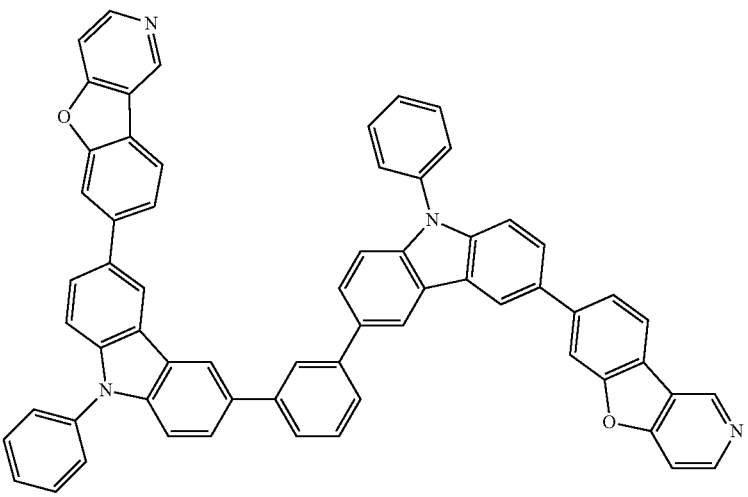 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| Polymers (e.g., PVK) | 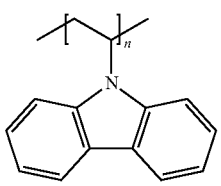 | Appl. Phys. Lett. 77, 2280 (2000) |

TABLE 3-continued
| MATERIAL | EXAMPLES OF MATERIAL | PUBLICATIONS |
|---|---|---|
| Spirofluorene compounds | 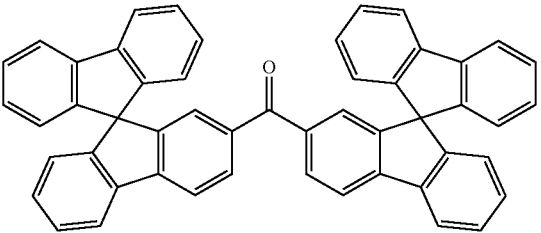 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzooxazole compounds | 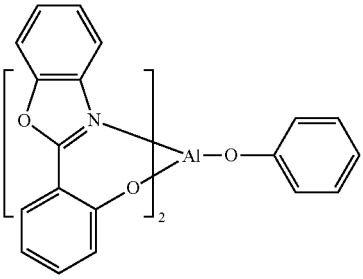 | WO2005089025 |
| | 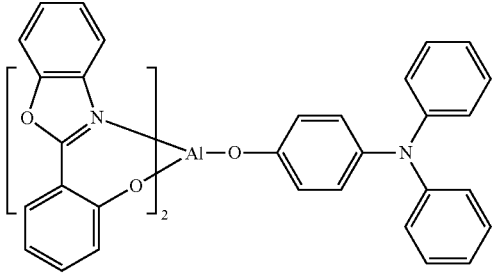 | WO2006132173 |
| | 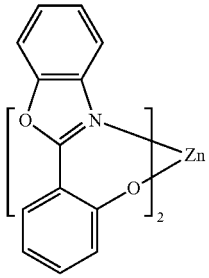 | JP200511610 |
| Spirofluorene-carbazole compounds | 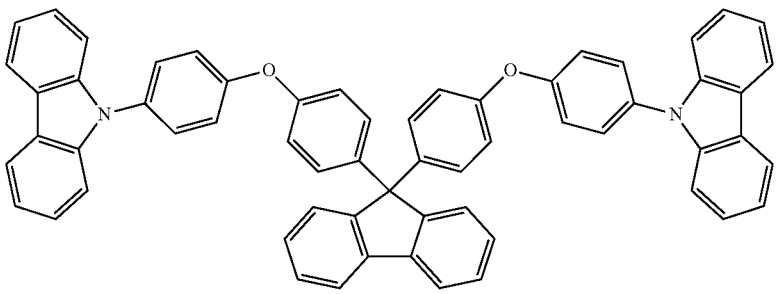 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |

TABLE 3-continued
| MATERIAL | EXAMPLES OF MATERIAL | PUBLICATIONS |
|---|---|---|
| | 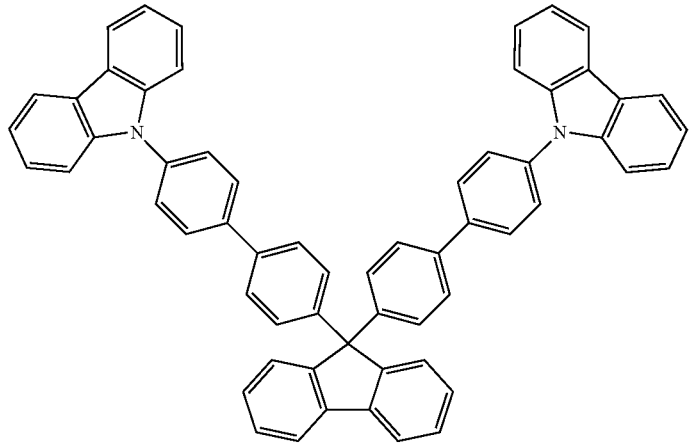 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocabazoles | 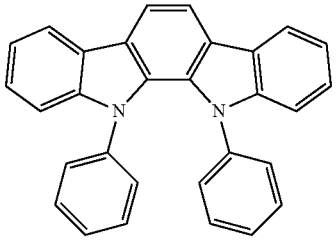 [SMILES: c1ccc(-n2c3ccccc3c3ccc4c5ccccc5n(-c5ccccc5)c4c32)cc1] | WO2007063796 |
| | 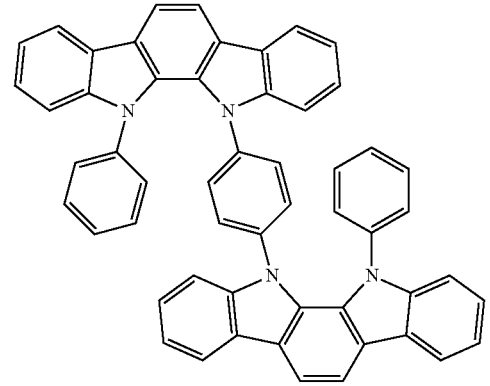 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole | 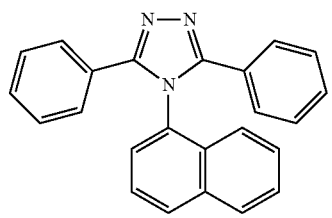 [SMILES: c1ccc(-c2nnc(-c3ccccc3)n2-c2cccc3ccccc23)cc1] | J. Appl. Phys. 90, 5048 (2001) |
| | 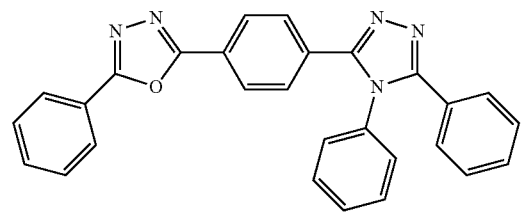 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
|---|---|---|
| Tetraphenylene complexes | 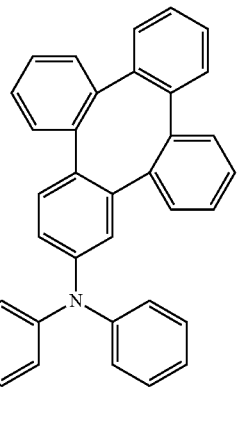 | US20050112407 |
| Metal phenoxypyridine compounds | 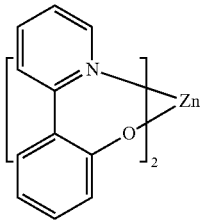 | WO2005030900 |
| Metal coordination complexes (e.g., Zn, Al with NN ligands) | 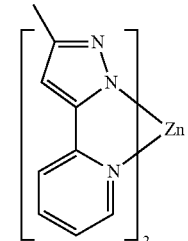 | US20040137268, US20040137267 |
| Blue hosts | | |
| Arylcarbazoles | 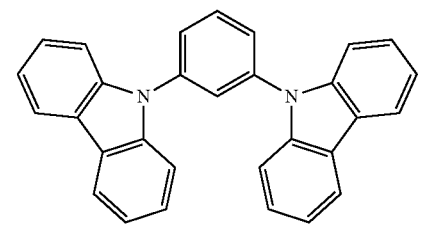 [SMILES: c1cc(-n2c3ccccc3c3ccccc32)cc(-n2c3ccccc3c3ccccc32)c1] | Appl. Phys. Lett. 82, 2422 (2003) |
| | 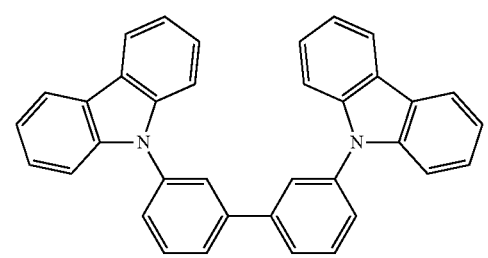 [SMILES: c1cc(-c2cccc(-n3c4ccccc4c4ccccc43)c2)cc(-n2c3ccccc3c3ccccc32)c1] | US20070190359 |

| MATERIAL | EXAMPLES OF MATERIAL | PUBLICATIONS |
|---|---|---|
| Dibenzothiophene/ Dibenzofuran-carbazole compounds | 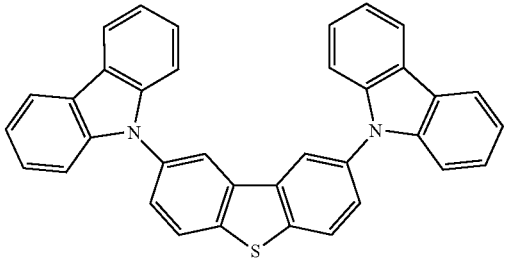 [SMILES: c1ccc2c(c1)c1ccccc1n2-c1ccc2sc3ccc(-n4c5ccccc5c5ccccc54)cc3c2c1] | WO2006114966, US20090167162 |
| | 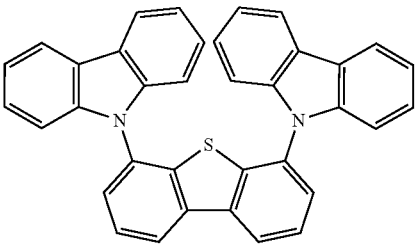 [SMILES: c1cc(-n2c3ccccc3c3ccccc32)c2sc3c(-n4c5ccccc5c5ccccc54)cccc3c2c1] | US20090167162 |
| | 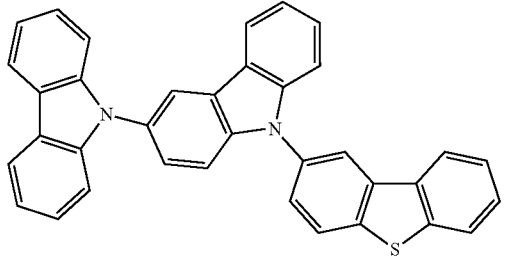 [SMILES: c1ccc2c(c1)sc1ccc(-n3c4ccccc4c4cc(-n5c6ccccc6c6ccccc65)ccc43)cc12] | WO2009086028 |
| | 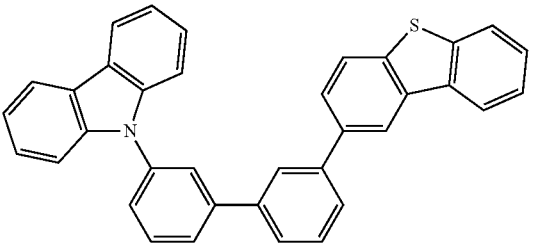 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 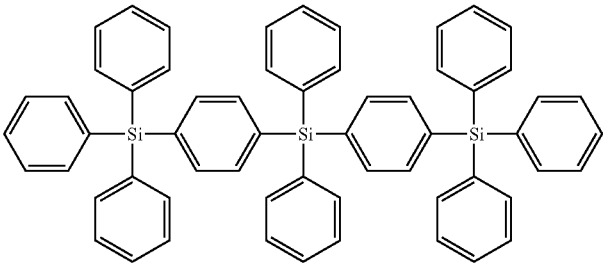 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US2005028919 |
| | 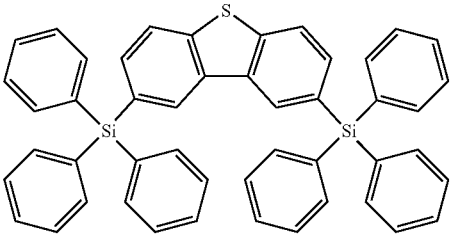 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| High triplet metal organometallic complex | | US7154114 |
| Phosphorescent dopants Red dopants | | |
| Heavy metal porphyrins (e.g., PtOEP) | | Nature 395, 151 (1998) |
| Iridium (III) organometallic complexes | | Appl. Phys. Lett. 78, 1622 (2001) |

TABLE 3-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 3-continued

| MATERIAL | EXAMPLES OF MATERIAL | PUBLICATIONS |
|---|---|---|
|  |  | US20070087321 |
|  |  | Adv. Mater. 19, 739 (2007) |
|  |  | WO2009100991 |
|  |  | WO2008101842 |
| Platinum (II) organometallic complexes |  | WO2003040257 |

TABLE 3-continued

| MATERIAL | EXAMPLES OF MATERIAL | PUBLICATIONS |
| --- | --- | --- |
| Osminum (III) complexes | | Chem. Mater. 17, 3532 (2005) |
| Ruthenium (II) complexes | | Adv. Mater. 17, 1059 (2005) |
| Rhenium (I), (II), and (III) complexes | | US20050244673 |
| Green dopants | | |
| Iridium (III) organometallic complexes | and its derivatiaves | Inorg. Chem. 40, 1704 (2001) |
| | | US20020034656 |

TABLE 3-continued
| MATERIAL | EXAMPLES OF MATERIAL | PUBLICATIONS |
|---|---|---|
| | 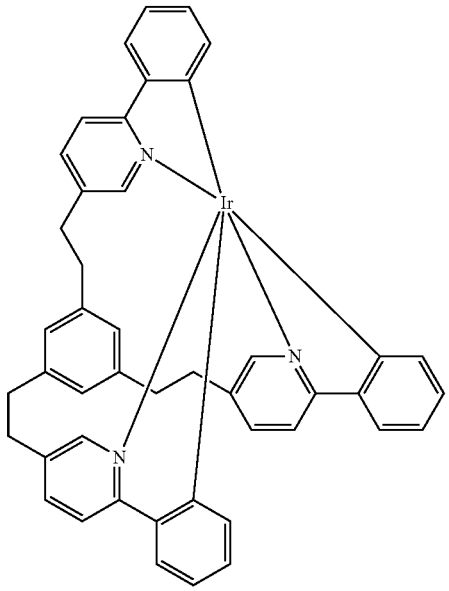 | US7332232 |
| | 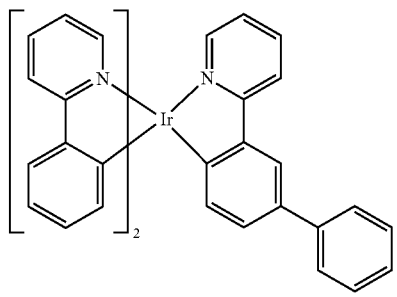 | US20090108737 |
| | 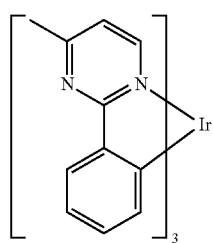 | US20090039776 |
| | 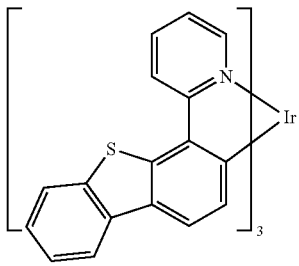 | US6921915 |

TABLE 3-continued

| MATERIAL | EXAMPLES OF MATERIAL | PUBLICATIONS |
|---|---|---|
| | | US6687266 |
| | | Chem. Mater. 16, 2480 (2004) |
| | | US20070190359 |
| | | US20060008670<br>JP2007123392 |
| | | Adv. Mater. 16, 2003 (2004) |

TABLE 3-continued
| MATERIAL | EXAMPLES OF MATERIAL | PUBLICATIONS |
|---|---|---|
|  | 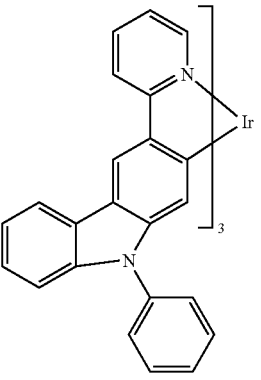 | Angew. Chem. Int. Ed. 2006, 45, 7800 |
|  | 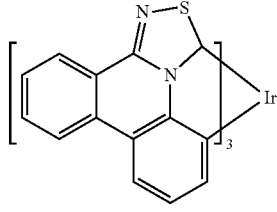 | WO2009050290 |
|  | 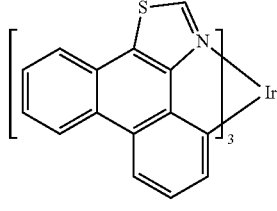 | US20090165846 |
|  | 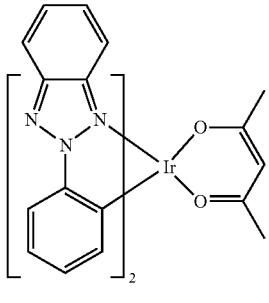 | US20080015355 |
| Monomer for polymeric metal organometallic compounds | 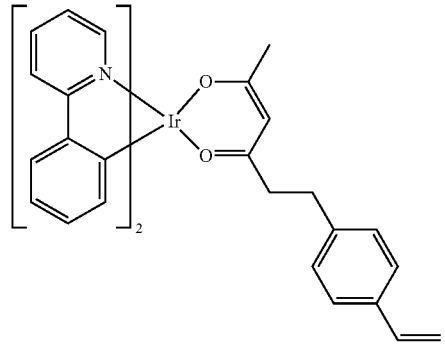 | US7250226, US7396598 |

TABLE 3-continued

| MATERIAL | EXAMPLES OF MATERIAL | PUBLICATIONS |
| --- | --- | --- |
| Pt (II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |
| | | US20060263635 |

TABLE 3-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium (III) complexes | | Inorg. Chem. 42, 1248 (2003) |
| Deuterated organometallic complexes | | US20030138657 |

TABLE 3-continued
| MATERIAL | EXAMPLES OF MATERIAL | PUBLICATIONS |
|---|---|---|
| Organometallic complexes with two or more metal centers | 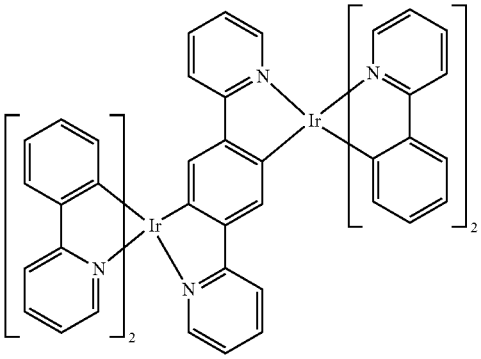 | US20030152802 |
| | 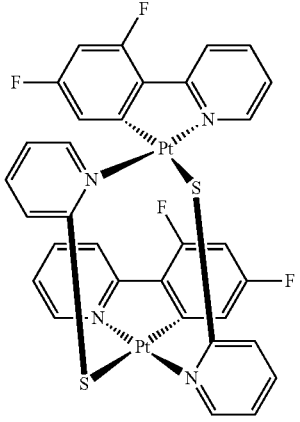 | US7090928 |
| Blue dopants | | |
| Iridium (III) organometallic complexes | 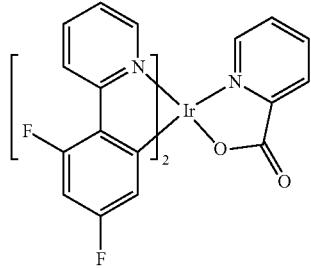 | WO2002002714 |
| | 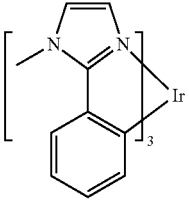 | WO2006009024 |
| | 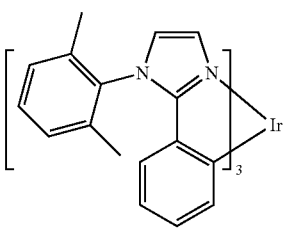 | US20060251923 |

TABLE 3-continued

| MATERIAL | EXAMPLES OF MATERIAL | PUBLICATIONS |
|---|---|---|
| | | US7393599, WO2006056418, US20050260441, WO2005019373 |
| | | US7534505 |
| | | US7445855 |
| | | US20070190359, US20080297033 |
| | | US7338722 |
| | | US20020134984 |

TABLE 3-continued
| MATERIAL | EXAMPLES OF MATERIAL | PUBLICATIONS |
|---|---|---|
| | 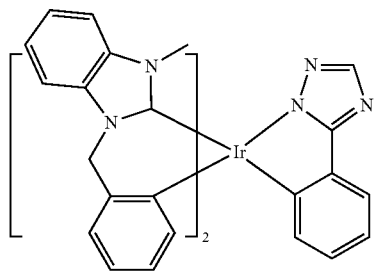 | Angew. Chem. Int. Ed. 47, 1 (2008) |
| | 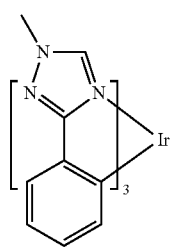 | Chem. Mater. 18, 5119 (2006) |
| | 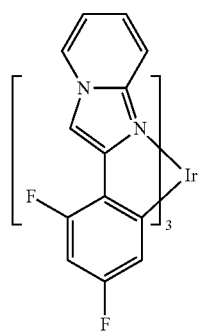 | Inorg. Chem. 46, 4308 (2007) |
| | 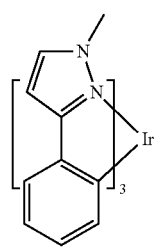 | WO2005123873 |
| | 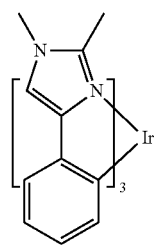 | WO2005123873 |
| | 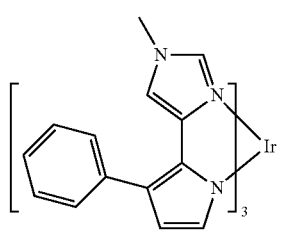 | WO2007004380 |

TABLE 3-continued

| MATERIAL | EXAMPLES OF MATERIAL | PUBLICATIONS |
|---|---|---|
| | | WO2006082742 |
| Osmium (II) complexes | | US7279704 |
| | | Organometallics 23, 3745 (2004) |
| Gold complexes | | Appl. Phys. Lett. 74, 1361 (1999) |
| Platinum (II) complexes | | WO2006098120, WO2006103874 |

Exciton/hole blocking layer materials

TABLE 3-continued
| MATERIAL | EXAMPLES OF MATERIAL | PUBLICATIONS |
|---|---|---|
| Bathocuprine compounds (e.g., BCP, BPhen) | 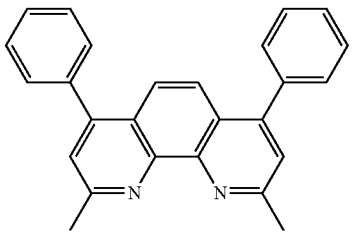 [SMILES: Cc1cc(-c2ccccc2)c2ccc3c(-c4ccccc4)cc(C)nc3c2n1] | Appl. Phys. Lett. 75, 4 (1999) |
| | 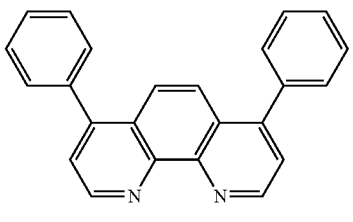 | Appl. Phys. Lett. 79, 449 (2001) |
| Metal 8-hydroxyquinolates (e.g., BAlq) | 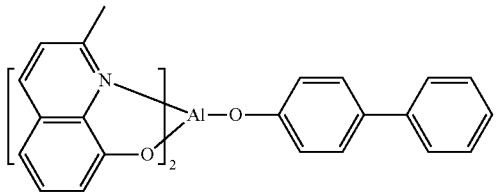 | Appl. Phys. Lett. 81, 162 (2002) |
| 5-member ring electron deficient heterocycles such as triazole, oxadiazole, imidazole, benzoimidazole | 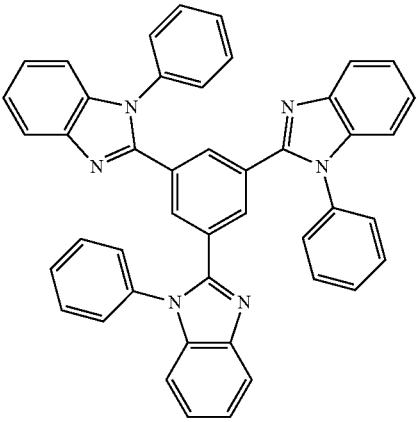 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 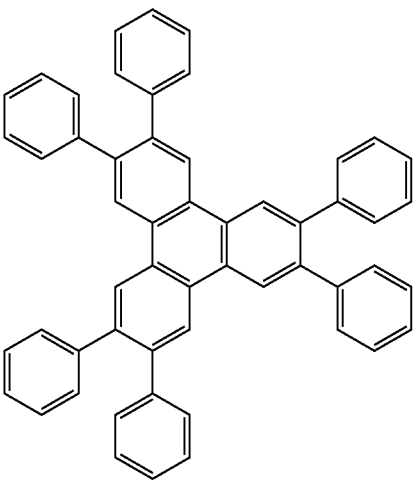 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 3-continued
| MATERIAL | EXAMPLES OF MATERIAL | PUBLICATIONS |
|---|---|---|
| Fluorinated aromatic compounds | 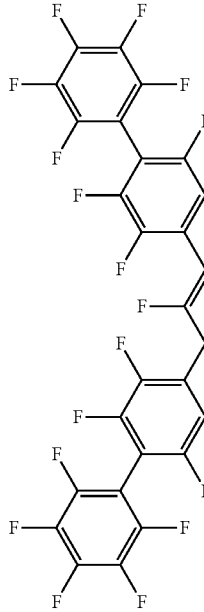 | Appl. Phys. Lett. 79, 156 (2001) |
| Phenothiazine-S-oxide | 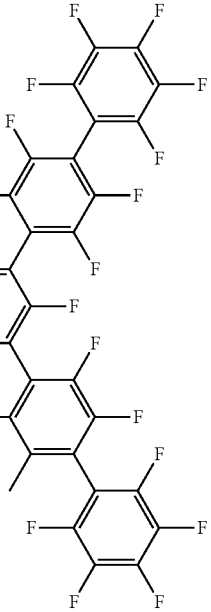 | WO2008132085 |
Electron transporting materials
| | | |
|---|---|---|
| Anthracene-benzoimidazole compounds | 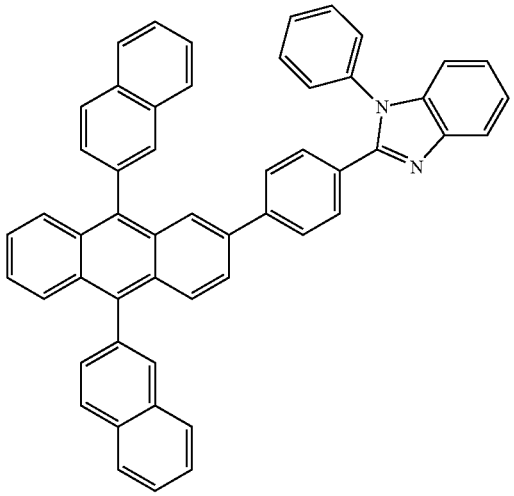 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 3-continued

| MATERIAL | EXAMPLES OF MATERIAL | PUBLICATIONS |
|---|---|---|
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987)<br>US7230107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |

| MATERIAL | EXAMPLES OF MATERIAL | PUBLICATIONS |
|---|---|---|
| | 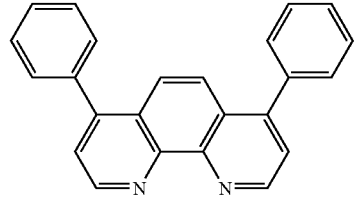 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole | 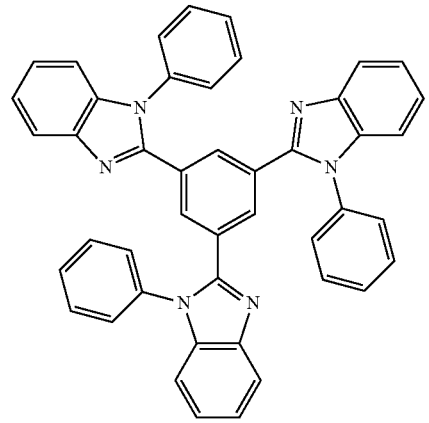 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 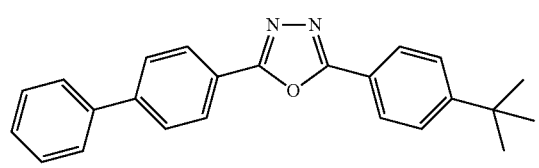 [SMILES: CC(C)(C)c1ccc(-c2nnc(-c3ccc(-c4ccccc4)cc3)o2)cc1] | Appl. Phys. Lett. 55, 1489 (1989) |
| | 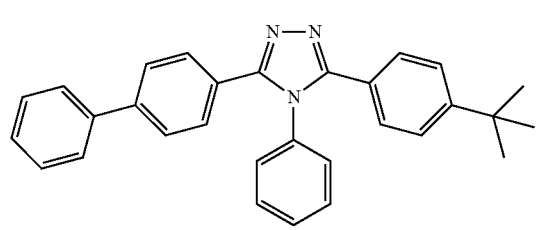 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 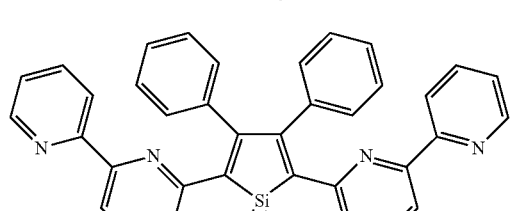 | Org. Electron. 4, 113 (2003) |
| Arylborane compounds | 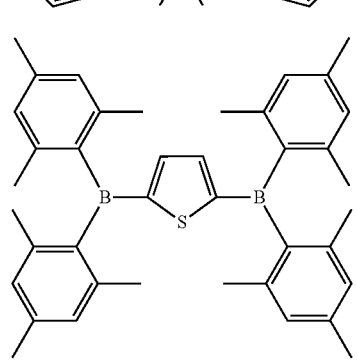 | J. Am. Chem. Soc. 120, 9714 (1998) |

TABLE 3-continued

| MATERIAL | EXAMPLES OF MATERIAL | PUBLICATIONS |
|---|---|---|
| Fluorinated aromatic compounds | | J. Am. Chem. Soc. 122, 1832 (2000) |
| Fullerene (e.g., C60) | | US20090101870 |
| Triazine complexes | | US20040036077 |
| Zn ÑN complexes | | US6528187 |

Experimental

Synthesis of Ionic Ir Complexes.

All ionic Ir complexes were synthesized with the general method goes as follows:

1 equivalent of bis-cyclometallated Ir(III) dichloro-bridged dimer and 2.2 equivalents of auxiliary ligand were refluxed in methanol overnight under $N_2$. Upon cooling, the reaction mixture was concentrated and the final products were purified by column chromatography.

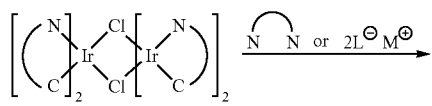

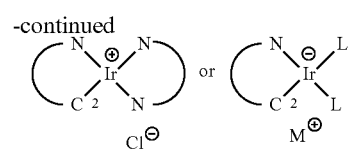

All the starting materials and solvents were purchased from commercial sources and used without further purification. The $^1H$ and $^{13}C$ NMR spectra were collected on a 400 MHz spectrometer at room temperature. Mass spectra were recorded on an Applied Biosystems Voyager-DE STR mass spectrometer. IR data was obtained from a Perkin Elmer Spectrum 2000 FT-IR spectrometer. Elemental analysis for the three soft salts was carried out in an Heraeus Vario EL III elemental analyzer at NSC Regional Adanved Instrument Center, national Taiwan University. Samples dried under vacuum at room temperature yielded elemental analyses with higher-than-expected percentage for carbon, consistent with solvent being trapped in the porous crystals. Heating the samples under vacuum overnight at 100° C. gave better CHN analyses (vide infra).

[Ir(tpy)$_2$(CN-t-Bu)$_2$]Cl, C1: The characterization was previously published. (See, Li, J. et al., Inorganic Chemistry 2005, 44(6), 1713-27.

[Ir(tpy)$_2$($^t$bpy)]Cl, C2. A mixture of iridium 2-(p-tolyl)pyridine dichloro-bridged dimer (150 mg, 0.13 mmol) and 4,4'-di-tert-butyl-2,2'-bipyridine (79 mg, 0.29 mmol) was dissolved in methanol (10 mL) and refluxed for 15 h. The solution was concentrated and washed with hexane to afford pure product (185 mg, 84%) as a yellow solid. $^1$H NMR (DMSO-d6, 400 MHz) δ 8.86 (s, 2H), 8.20 (d, J=8.0, 2H), 7.90 (td, J=7.5, 1.4, 2H), 7.80 (d, J=8.0, 2H), 7.76 (d, J=5.9, 2H), 7.72 (dd, J=5.9, 1.9, 2H), 7.55 (d, J=5.8, 2H), 7.13 (td, J=6.6, 1.4, 2H), 6.83 (dd, J=7.9, 1.1 2H), 5.98 (s, 2H), 2.06 (s, 6H), 1.38 (s, 18H); $^{13}$C NMR, (DMSO-d6, 100 MHz) δ 166.88, 163.43, 155.03, 151.36, 149.41, 148.59, 141.15, 139.52, 138.52, 131.61, 125.43, 124.94, 123.32, 123.10, 122.17, 119.60, 35.64, 29.95, 21.43; MS (MALDI) m/z 797 (M—Cl).

Na[Ir(tpy)$_2$(CN)$_2$], A1: Iridium 2-(p-tolyl)pyridine dichloro-bridged dimer (500 mg, 0.44 mmol) was combined with sodium cyanide (261 mg, 5.32 mmol) in methanol (50 mL) and refluxed with stirring for 15 h. The crude product was purified through column chromatography on silica gel (DMF) to yield pure product (470 mg, 88%) as a light yellow solid. $^1$H NMR (DMSO-d6, 400 MHz) δ 9.48 (d, J=6.0, 2H), 8.02 (d, J=8.0, 2H), 7.86 (td, J=8.0, 1.2, 2H), 7.55 (d, J=8.0, 2H), 7.26 (td, J=6.0, 1.2, 2H), 6.55 (dd, J=8.0, 1.2, 2H), 5.89 (s, 2H), 1.92 (s, 6H); $^{13}$C NMR, (DMSO-d6, 100 MHz) δ 167.84, 163.98, 153.07, 141.83, 137.00, 135.90, 131.55, 131.07, 123.52, 121.91, 120.95,] 18.51, 21.41; IR: 2102, 2088 cm$^{-1}$ (terminal C≡N stretch); MS (MALDI) m/z 581 (M-Na).

Na[Ir(pq)$_2$(CN)$_2$], A2: Iridium phenyl quinoline dichloro-bridged dimer (500 mg, 0.39 mmol) was combined with sodium cyanide (231 mg, 4.71 mmol) in methanol (50 mL) and refluxed with stirring for 15 h. The crude product was purified through column chromatography on silica gel (DMF) to yield pure product (521 mg, 94%) as a light yellow solid. $^1$H NMR (DMSO-d6, 400 MHz) δ 10.13 (d, J=8.0, 2H), 8.48 (d, J=8.0, 2H), 8.26 (d, J=8.0, 2H), 8.04 (dd, J=8.0, 1.6, 2H), 7.80 (d, J=8.0, 2H), 7.75 (td, J=8.0, 1.6, 2H), 7.68 (td, J=8.0, 1.6, 2H), 6.76 (td, J=8.0, 1.2, 2H), 6.54 (td, J=8.0, 1.2, 2H), 5.95 (dd, J=8.0, 1.2, 2H); $^{13}$C NMR, (DMSO-d6, 100 MHz) δ 171.46, 166.75, 148.75, 146.91, 138.25, 132.8, 131.52, 130.19, 129.80, 128.80, 127.85, 127.32, 126.17, 125.82, 120.00, 117.64; IR: 2107, 2087 cm$^{-1}$ (terminal C≡N stretch); MS (MALDI) m/z 653 (M-Na).

Na[Ir(dfppy)$_2$(CN)$_2$], A3: Iridium 2-(2,4-Difluorophenyl)pyridine dichloro-bridged dimer (300 mg, 0.25 mmol) was combined with sodium cyanide (145 mg, 2.96 mmol) in methanol (30 mL) and refluxed with stirring for 15 h. The crude product was purified through column chromatography on silica gel (DMF) to yield pure product (270 mg, 84%) as a light yellow solid. $^1$H NMR (DMSO-d6, 400 MHz) δ 9.55 (d, 0.1=6.0, 2H), 8.22 (d, 0.1=8.0, 2H), 8.03 (td, 0.1=8.0, 1.2, 2H), 7.44 (td, 0.1=6.0, 1.2, 2H), 6.63 (ddd, 0.1=12.8, 9.6, 2.4, 2H), 5.54 (dd, 0.1=8.0, 2.4, 2H); 13C NMR, (DMSO-d6, 100 MHz) δ 170.2, 163.42, 154.97, 145.83, 139.76, 137.44, 132.17, 129.64, 124.72, 123.36, 121.62, 120.11, 59.49, 24.77, 20.70, 13.93; IR: 2114, 2106 cm-1 (terminal C≡N stretch); MS (MALDI) m/z 625 (M-Na).

Synthesis of Ir-Based Soft Salts.

All the Ir-based soft salts were synthesized by general method goes as follows:

1 equivalent of cationic Ir complex and 1 equivalents of anionic Ir complex were stirred in water at room temperature for an hour. The reaction mixture was extracted with CH$_2$Cl$_2$. The organic layer was combined and dried over MgSO$_4$ before concentrated under vacuum. The resulting solid was washed with ethyl ether to afford final product.

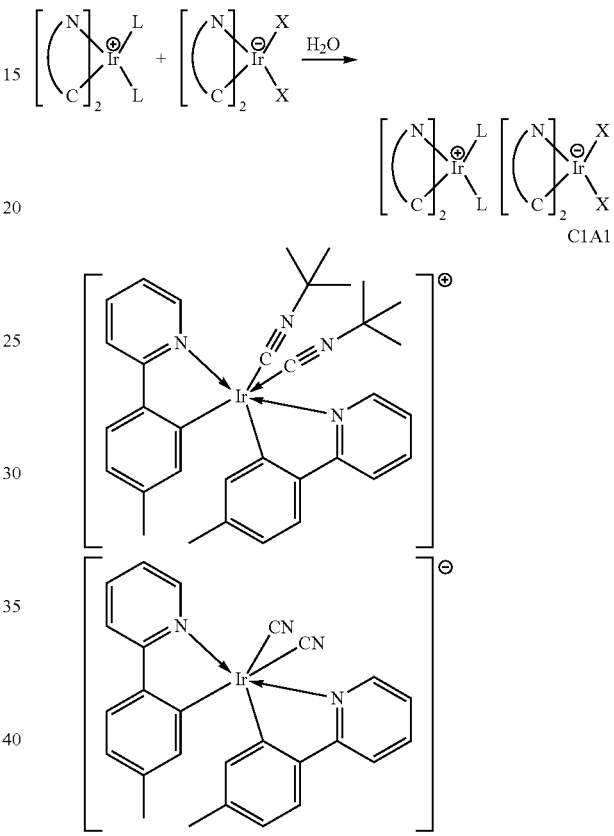

C1A1

C1A1: [Ir(tpy)$_2$(CN)$_2$]OTf (50 mg, 0.07 mmol) and Na[Ir(tpy)$_2$(CN)$_2$] (50 mg, 0.08 mmol) was added to water (10 mL). The reaction mixture was stirred for 1 h at room temperature and then extracted with CH$_2$Cl$_2$. The combined organic extracts were dried over MgSO$_4$ and concentrated by rotary evaporation. The resulting solid was washed with ethyl ether to afford soft salt 1 (49 mg, 65%) as a yellow solid. $^1$H NMR (DMSO-d6, 400 MHz) δ 9.48 (d, J=5.1, 2H), 8.98 (d, J=5.8, 2H), 8.29 (d, J=7.9, 2H), 8.17 (td, J=7.8, 1.4, 2H), 8.00 (d, J=7.8, 2H), 7.85 (td, J=7.8, 1.6, 2H), 7.78 (d, J=8.0, 2H), 7.55 (d, J=8.0, 4H), 7.51 (td, J=6.7, 1.5, 2H), 7.25 (td, J=6.6, 1.4, 2H), 6.80 (dd, J=7.9, 1.1, 2H), 6.55 6 (dd, J=8.4, 1.8, 2H), 5.89 (s, 2H), 5.83 (s, 2H), 1.98 (s, 6H), 1.92 (s, 6H), 1.31 (s, 18H); $^{13}$C NMR, (DMSO-d6, 100 MHz) δ is 167.85, 166.60, 164.05, 153.30, 153.13, 153.10, 141.85, 141.28, 139.50, 139.23, 136.99, 135.88, 131.57, 131.01, 130.35, 124.82, 124.52, 124.13, 123.51, 121.91, 120.94, 120.43, 118.50, 94.48, 58.52, 29.51, 21.42; IR: 2187, 2161, 2101, 2093 cm$^{-1}$ (terminal C≡N stretch); MS (MALDI) m/z 695 (M+), 581 (M−). Anal Calcd. for C$_{60}$H$_{58}$Ir$_2$N$_8$.2H$_2$O: C, 54.94; H, 4.76; N, 8.54. Found: C, 54.62, H, 4.75, N, 8.32.

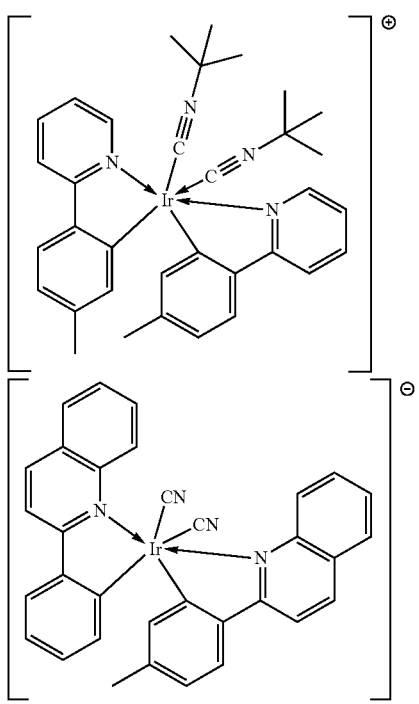

C1A2

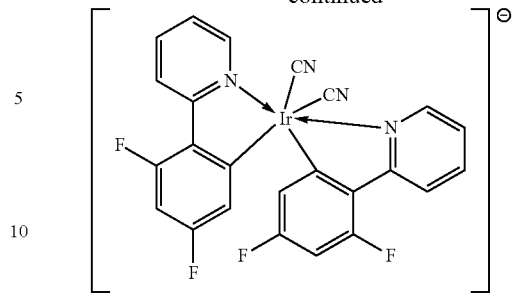

C1A2: [Ir(tpy)₂(CN)₂]OTf (80 mg, 0.09 mmol) and Na[Ir(pq)₂(CN)₂] (80 mg, 0.11 mmol) was added to water (15 mL). The reaction mixture was stirred for 1 h at room temperature and then extracted with CH₂Cl₂. The combined organic extracts were dried over MgSO₄ and concentrated by rotary evaporation. The resulting solid was washed with ethyl ether to afford soft salt 2 (85 mg, 67%) as a yellow solid. ¹H NMR (DMSO-d6, 400 MHz) δ is 10.13 (d, J=8.8, 2H), 8.98 (d, J=6.1, 2H), 8.46 (d, J=8.6, 2H), 8.28 (d, J=7.9, 2H), 8.24 (d, J=9.0, 2H), 8.17 (td, J=8.1, 1.5, 2H), 8.01 (dd, J=7.9, 1.6, 2H), 7.78 (d, J=8.0, 4H), 7.72 (td, J=7.8, 1.7, 2H), 7.66 (td, J=7.4, 1.1, 2H), 7.51 (td, J=6.6, 1.5, 2H), 6.80 (dd, J=7.9, 1.1, 2H), 6.73 (td, J=7.2, 1.3, 2H), 6.51 (t, J=7.3, 2H), 5.93 (d, J=7.6, 2H), 5.84 (s, 2H), 1.98 (s, 6H), 1.30 (s, 18H); ¹³C NMR, (DMSO-d6, 100 MHz) δ is 171.42, 166.79, 166.57, 153.20, 153.02, 148.74, 146.86, 141.21, 139.44, 139.11, 138.15, 132.81, 131.50, 130.31, 130.08, 129.69, 128.71, 127.75, 127.27, 126.08, 125.72, 124.72, 124.38, 124.05, 120.35, 119.92, 117.54, 58.43, 29.47, 21.33; IR: 2183, 2159, 2105, 2088 cm⁻¹ (terminal C≡N stretch); MS (MALDI) m/z 695 (M+), 653 (M} Anal Calcd. for C₆₆H₂₈Ir₂N₈.2H₂O: C, 57.29; H, 4.52; N, 8.10. Found: C, 57.29, H, 4.63, N, 8.04.

C2A3

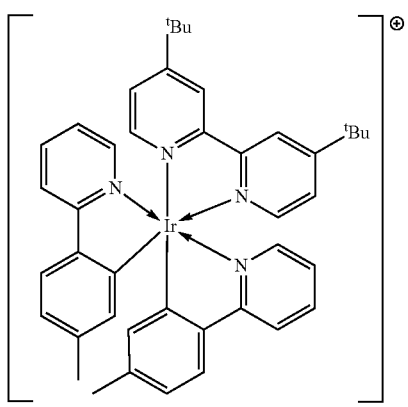

C2A3: [Ir(tpy)₂(¹bpy)]Cl (83 mg, 0.10 mmol) and Na[Ir(dfppy)₂(CN)₂] (80 mg, 0.12 mmol) was added to water (15 mL). The reaction mixture was stirred for 1 h at room temperature and then extracted with CH₂Cl₂. The combined organic extracts were dried over MgSO₄ and concentrated by rotary evaporation. The resulting solid was washed with ethyl ether to afford soft salt 3 (90 mg, 64%) as a yellow solid. ¹H NMR (DMSO-d6, 400 MHz) δ is 9.54 (dd, J=4.8, 1.0, 2H), 8.85 (s, 2H), 8.19 (d, J=7.5, 4H), 8.03 (td, J=8.3, 1.3, 2H), 7.90 (td, J=8.2, 1.5, 2H), 7.80 (d, J=8.0, 2H), 7.76 (d, J=5.9, 2H), 7.71 (dd, J=5.9, 1.9, 2H), 7.55 (d, J=5.8, 2H), 7.44 (td, J=6.6, 1.4, 2H), 7.12 (td, J=6.7, 1.4, 2H), 6.84 (dd, J=8.3, 1.3, 2H), 6.60 (ddd, J=13.0, 9.4, 2.5, 2H), 5.98 (s, 2H), 5.52 (dd, J=8.3, 2.5, 2H), 2.06 (s, 6H), 1.38 (s, 18H); ¹³C NMR, (DMSO-d6, 100 MHz) δ is 166.88, 163.43, 155.03, 151.36, 149.41, 148.59, 141.15, 139.52, 138.52, 131.61, 125.43, 124.94, 123.32, 123.10, 122.17, 119.60, 35.64, 29.95, 21.43; IR: 2113, 2106 cm⁻¹ (terminal C≡N stretch); MS (MALDI) m/z 797 (M+), 625 (M} Anal Calcd. for C₆₆H₅₆F₄Ir₂N₈.2H₂O: C, 55.06; H, 4.06; N, 7.78. Found: C, 55.06, H, 4.57, N, 7.65.

Characterization Methods.

Oxidation and reduction potentials were measured by cyclic voltammetry (CY) using an EG&G potentiostat model 283. CY scans were recorded at a scan rate of 100 mV/s in dry and degassed DMF with 0.1 M tetrabutylammonium hexafluorophosphate as electrolyte. Ferrocene/ferrocenium (Cp₂Fe/Cp₂Fe⁺) redox couple was used as an internal reference. A Pt wire and a glassy carbon rod worked as the counter and the working electrode, respectively. An Ag wire was also used as a pseudoreference electrode. The quenching study applied to determine the bimolecular quenching rate constants is calculated according to Equation 1.

$$\tau_0/\tau = 1 + K_q \tau_0 [Q] \quad (1)$$

τ and τ₀ are the excited state lifetime with and without the quencher, Kq is the experimental quenching rate constant and [Q] is the molar concentration of the quencher. All the sample solutions for the quenching study had the same concentration for the emitter, A3, at 0.67 μM. The concentration of the quencher, C2, ranged from 0 to 120 μM. Lifetime measurements were performed on an IBH lifetime system after all the solution samples were bubble-degassed with nitrogen for 5 minutes and excited at 380 nm. Both photoluminescence (PL) and electroluminescence (EL) emission spectra were obtained by a PTI QuantaMaster model C-60SE spectrofluorometer, equipped with a 928 PMT detector and corrected for detector response. Acetonitrile was used as solvent for solution PL. Films used for obtaining PL spectra and quantum yield were spin-coated on quartz substrates in air at room temperature from acetonitrile solutions. Quantum yield was measured by a Hamamatsu PL Quantum Yield Measurement System (C9920-01).

Device (OLED) Fabrication and Testing.

The OLEDs were grown on pre-cleaned indium tin oxide (ITO) coated glass substrates with sheet resistance of 20 Ω/sq. 20 mg PYK was dissolved in 1 mL dichlorobenzene and filtered before being spin-coated onto ITO at a rate of 3000 rpm for 40 seconds, followed by baking at 90° C. for 1 h under vacuum. The soft salts were then spin-coated from the acetonitrile solution (30 mg/ml) before the baking under the same conditions. Thereafter, the substrates were transferred to the vacuum chamber where the BCP layer was deposited by thermal evaporation from a resistively heated tantalum boat at a rate of around 2 Å/s. A shadow mask was placed on the substrates and the cathode consisting of 10 Å of LiF and 1200 Å of Al was subsequently deposited. The devices were tested in air within 1 h after fabrication. Light coming out from the front surface was collected by a UV –818 Si photocathode leading to a Keithley 2400 SourceMeter/2000 multimeter coupled to a Newport 1835-C optical meter. Device current-voltage and light-intensity characteristics were measured using the LabVIEW program by National Instruments.

The three soft salts were used in the OLED devices with structure of ITO/PVK/soft salt/BCP/LiF/Al. The external quantum efficiency (EQE) and J-V data are presented in FIG. 7.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A compound comprising the formula:

$$\sum_{i=1}^{m} C_i^{ai+} + \sum_{j=1}^{n} C_j^{bj-},$$

wherein $C_i^{ai+}$ is an organometallic cation having formula $C_i$ with $a_i$ positive charge;
wherein $C_j^{bj+}$ is an organometallic anion having formula $C_j$ with $b_j$ negative charge;
wherein formula $C_i$ is $(L_i)_f M_i X_i$; formula $C_j$ is $(L_j)_g M_j X_j$;
wherein each of $M_i$ and $M_j$ is independently a transition metal or a lanthanide;
wherein each of $L_i$ and $L_j$ is independently a mono-, di-, tri- or polydentate ligand;
wherein each of f and g may represent 2 or 3;
wherein $X_i$ and $X_j$ represent any number of chelated or auxiliary ligands;
wherein $$\sum_{i=1}^{m} a_i = \sum_{j=1}^{n} b_j;$$

and
wherein m and n are integers of 1 to 20;
wherein the organometallic anion is selected from the group consisting of:

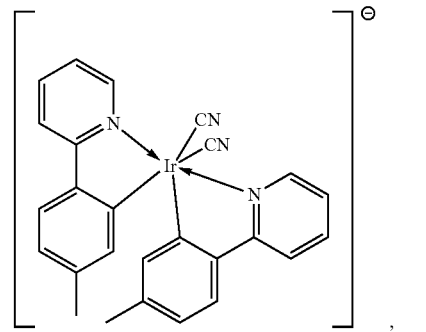
,

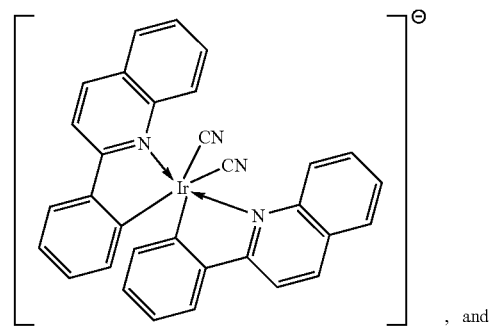
, and

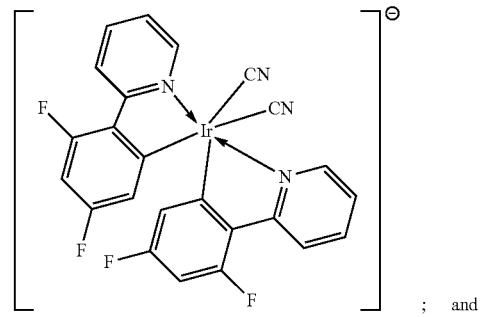
; and wherein the organometallic cation is selected from the group consisting of:

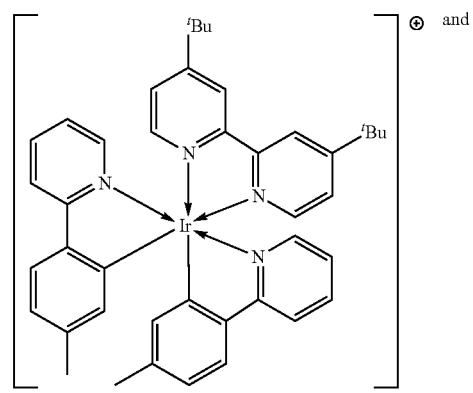
and

-continued

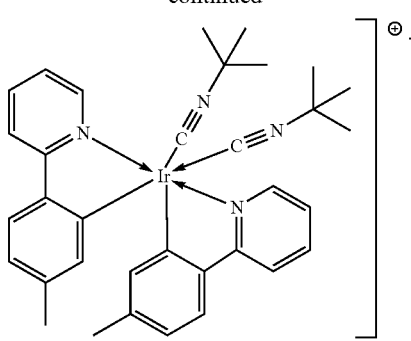

2. The compound of claim 1, wherein the compound is selected from the group consisting of:

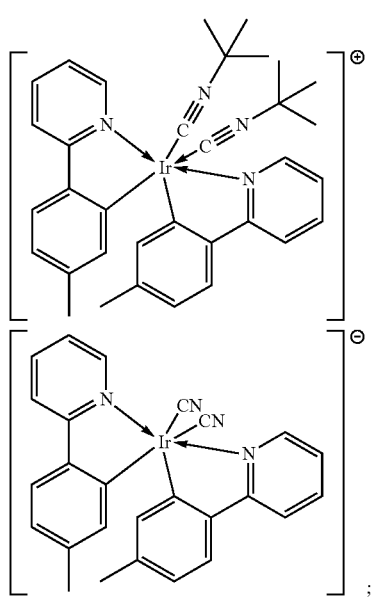

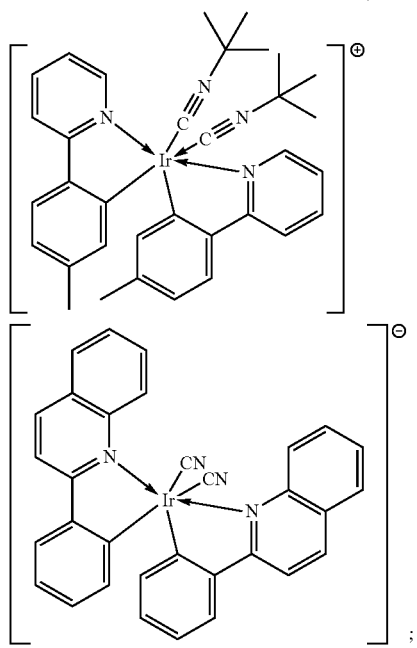

; and

-continued

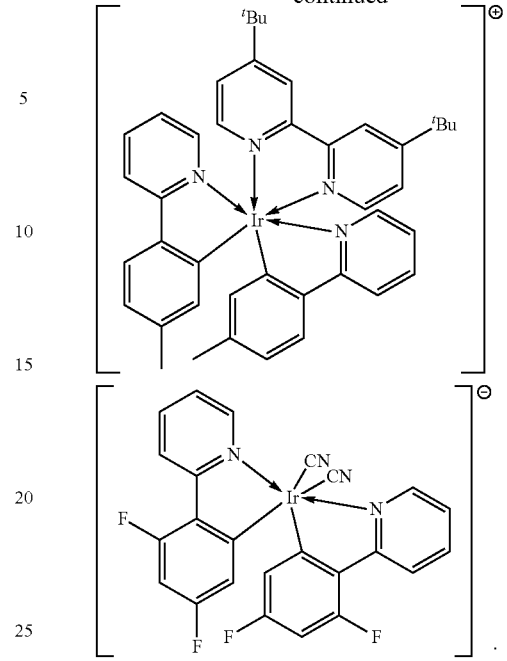

3. An organic light emitting device comprising:
an anode;
a cathode; and
an organic layer, disposed between the anode and the cathode, further comprising a compound comprising the formula:

$$\sum_{i=1}^{m} C_i^{ai+} \sum_{j=1}^{n} C_j^{bj-};$$

wherein $C_i^{ai+}$ is an organometallic cation having formula $C_i$ with $a_i$ positive charge;
wherein $C_j^{bj+}$ is an organometallic anion having formula $C_j$ with $b_j$ negative charge;
wherein formula $C_i$ is $(L_i)_f M_i X_i$; formula $C_j$ is $(L_j)_g M_j X_j$;
wherein each of $M_i$ and $M_j$ is independently a transition metal or a lanthanide;
wherein each of $L_i$ and $L_j$ is independently a mono-, di-, tri- or polydentate ligand;
wherein each of f and g may represent 2 or 3;
wherein $X_i$ and $X_j$ represent any number of chelated or auxiliary ligands;
wherein $$\sum_{i=1}^{m} a_i = \sum_{j=1}^{n} b_j;$$

and
wherein m and n are integers of 1 to 20;
wherein the organometallic anion is selected from the group consisting of:

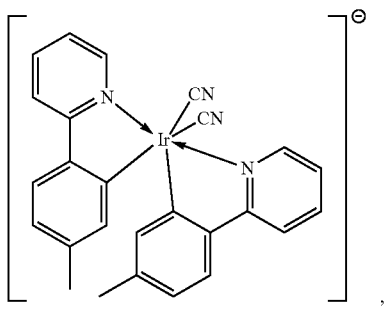
,
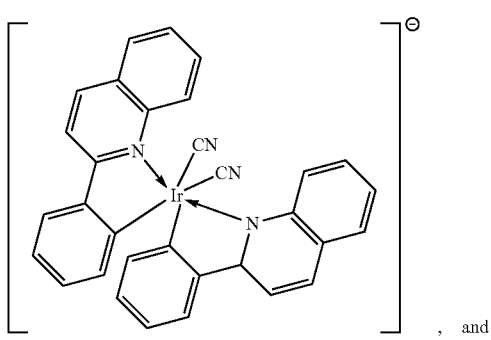
, and
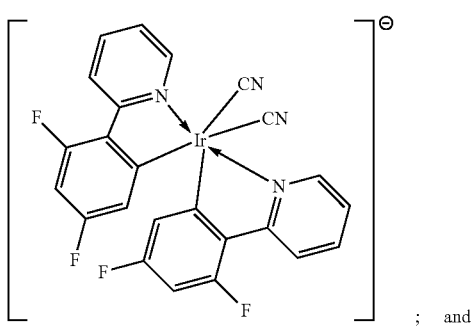
; and
wherein the organometallic cation is selected from the group consisting of:
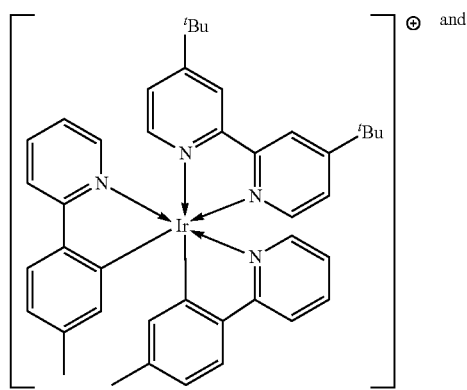
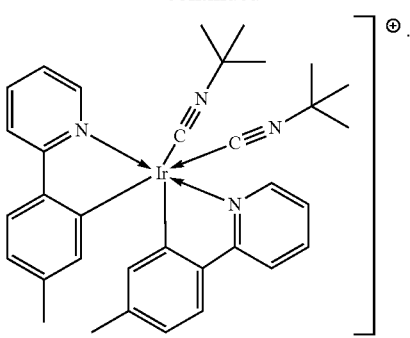
.
4. The device of claim 3, wherein the compound is selected from the group consisting of:
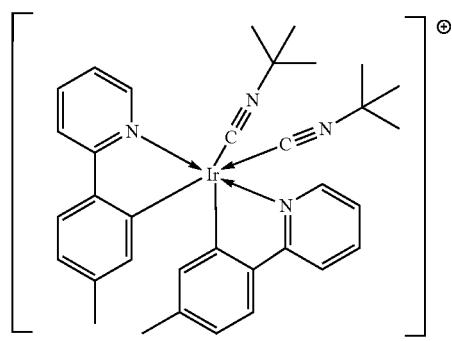
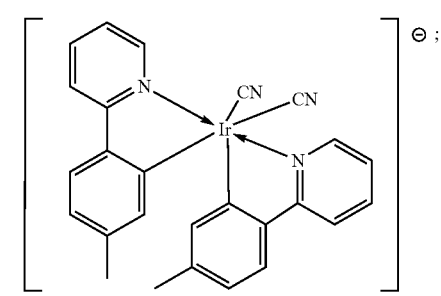
;
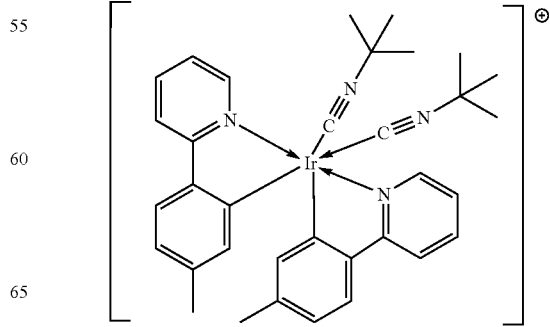

-continued

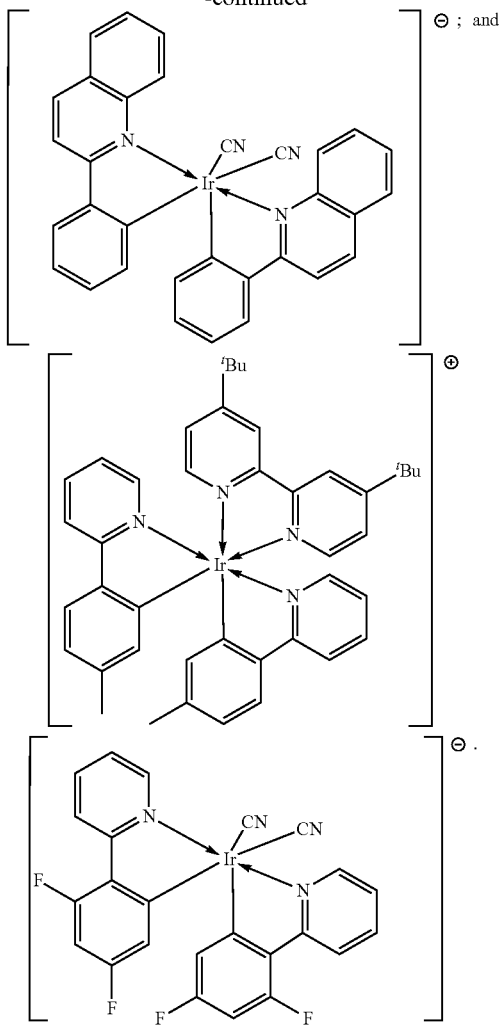

5. The device of claim 3, wherein one of the organometallic anion and the organometallic cation has both a lower oxidation potential and a less negative reduction potential than the other.

6. A method, comprising:
reducing an organometallic cation having the formula: $C_i^{ai+}$ be neutral,
oxidizing an organometallic anion having the formula: $C_j^{bj+}$ to be neutral, and
reacting the two neutral species to form an organometallic complex comprising the formula:

$$\sum_{i=1}^{m} C_i^{ai+} \sum_{j=1}^{n} C_j^{bj-},$$

wherein formula $C_i$ is $(L_i)_f M_i X_i$ and formula $C_j$ is $(L_j)_g M_j X_j$;
wherein each of $M_i$ and $M_j$ is independently a transition metal or a lanthanide;
wherein each of $L_i$ and $L_j$ is independently a mono-, di-, tri- or polydentate ligand;
wherein each of f and g may represent 2 or 3;
wherein $X_i$ and $X_j$ represent any number of chelated or auxiliary ligands;
wherein $$\sum_{i=1}^{m} a_i = \sum_{j=1}^{n} b_j;$$

and
wherein m and n are integers of 1 to 20.

7. The method of claim 6, wherein the neutral metallated complexes are thermally vacuum deposited in combination onto a substrate wherein the reaction is completed to obtain the organometallic complex.

8. The method of claim 6, further comprising:
providing a first electrode;
depositing the organometallic cation and the organometallic anion over the first electrode; and
depositing a second electrode.

9. The method of claim 8, wherein the first electrode is an anode and the second electrode is a cathode.

* * * * *